(12) United States Patent
Carter et al.

(10) Patent No.: US 9,685,297 B2
(45) Date of Patent: *Jun. 20, 2017

(54) SYSTEMS AND METHODS FOR MONITORING FAULTS, ANOMALIES, AND OTHER CHARACTERISTICS OF A SWITCHED MODE ION ENERGY DISTRIBUTION SYSTEM

(75) Inventors: Daniel Carter, Fort Collins, CO (US); Victor Brouk, Fort Collins, CO (US); Daniel J. Hoffman, Fort Collins, CO (US)

(73) Assignee: ADVANCED ENERGY INDUSTRIES, INC., Fort Collins, CO (US)

( * ) Notice: Subject to any disclaimer, the term of this patent is extended or adjusted under 35 U.S.C. 154(b) by 734 days.

This patent is subject to a terminal disclaimer.

(21) Appl. No.: 13/597,093

(22) Filed: Aug. 28, 2012

(65) Prior Publication Data

US 2014/0062495 A1    Mar. 6, 2014

(51) Int. Cl.
| | |
|---|---|
| C23C 14/34 | (2006.01) |
| H01J 37/08 | (2006.01) |
| G01N 27/06 | (2006.01) |
| H01J 37/32 | (2006.01) |

(52) U.S. Cl.
CPC .............. *H01J 37/08* (2013.01); *G01N 27/06* (2013.01); *H01J 37/3299* (2013.01); *H01J 37/32944* (2013.01)

(58) Field of Classification Search
CPC ... H01J 37/08; H01J 37/32944; H01J 37/3299
See application file for complete search history.

(56) References Cited

U.S. PATENT DOCUMENTS

| | | |
|---|---|---|
| 4,622,094 A | 11/1986 | Otsubo |
| 4,693,805 A | 9/1987 | Quazi |
| 4,963,239 A | 10/1990 | Fujita et al. |
| (Continued) | | |

FOREIGN PATENT DOCUMENTS

| | | |
|---|---|---|
| EP | 0383570 A2 | 8/1990 |
| EP | 1978542 A1 | 10/2008 |
| (Continued) | | |

OTHER PUBLICATIONS

Masaaki Awano, "Japanese Office Action re Application No. 2012-508593", Apr. 19, 2013, p. 11, Published in: JP.

(Continued)

*Primary Examiner* — John Brayton
(74) *Attorney, Agent, or Firm* — Neugeboren O'Dowd PC

(57) ABSTRACT

Systems, methods and apparatus for regulating ion energies in a plasma chamber and chucking a substrate to a substrate support are disclosed. An exemplary method includes placing a substrate in a plasma chamber, forming a plasma in the plasma chamber, controllably switching power to the substrate so as to apply a periodic voltage function (or a modified periodic voltage function) to the substrate, and modulating, over multiple cycles of the periodic voltage function, the periodic voltage function responsive to a defined distribution of energies of ions at the surface of the substrate so as to effectuate the defined distribution of ion energies on a time-averaged basis.

19 Claims, 44 Drawing Sheets

(56) References Cited

U.S. PATENT DOCUMENTS

| | | |
|---|---|---|
| 5,057,185 A | 10/1991 | Singh et al. |
| 5,156,703 A | 10/1992 | Oechsner |
| 5,160,397 A | 11/1992 | Doki et al. |
| 5,242,561 A | 9/1993 | Sato |
| 5,247,669 A | 9/1993 | Abraham et al. |
| 5,415,718 A | 5/1995 | Ohmi et al. |
| 5,487,785 A | 1/1996 | Horiike et al. |
| 5,535,906 A | 7/1996 | Drummond |
| 5,770,972 A | 6/1998 | Collier et al. |
| 5,859,428 A | 1/1999 | Fruchtman |
| 5,983,828 A | 11/1999 | Savas |
| 6,030,667 A | 2/2000 | Nakagawa et al. |
| 6,051,114 A | 4/2000 | Yao et al. |
| 6,110,287 A | 8/2000 | Arai et al. |
| 6,156,667 A | 12/2000 | Jewett |
| 6,201,208 B1 | 3/2001 | Wendt et al. |
| 6,291,938 B1 | 9/2001 | Jewett et al. |
| 6,313,583 B1 | 11/2001 | Arita et al. |
| 6,326,584 B1 | 12/2001 | Jewett et al. |
| 6,392,210 B1 | 5/2002 | Jewett et al. |
| 6,544,895 B1 | 4/2003 | Donohoe |
| 6,707,051 B2 | 3/2004 | Shun'ko |
| 6,714,033 B1 | 3/2004 | Makhratchev et al. |
| 6,724,148 B1 | 4/2004 | Gonzalez et al. |
| 6,777,037 B2 | 8/2004 | Sumiya et al. |
| 6,794,301 B2 | 9/2004 | Savas |
| 6,819,096 B2 | 11/2004 | Gonzalez et al. |
| 6,822,396 B2 | 11/2004 | Gonzalez et al. |
| 6,863,018 B2 | 3/2005 | Koizumi et al. |
| 6,872,289 B2 | 3/2005 | Mizuno et al. |
| 6,885,153 B2 | 4/2005 | Quon |
| 6,913,938 B2 | 7/2005 | Shanmugasundram et al. |
| 6,920,312 B1 | 7/2005 | Benjamin |
| 6,927,358 B2 | 8/2005 | Gonzalez et al. |
| 6,946,063 B1 | 9/2005 | Gonzalez et al. |
| 6,984,198 B2 | 1/2006 | Krishnamurthy et al. |
| 7,005,845 B1 | 2/2006 | Gonzalez et al. |
| 7,046,524 B2 | 5/2006 | Hoffman et al. |
| 7,059,267 B2 | 6/2006 | Hedberg et al. |
| 7,201,936 B2 | 4/2007 | Schwarm et al. |
| 7,245,084 B1 | 7/2007 | Gonzalez et al. |
| 7,253,117 B2 | 8/2007 | Donohoe |
| 7,297,637 B2 | 11/2007 | Hedberg et al. |
| 7,373,899 B2 | 5/2008 | Sumiya et al. |
| 7,468,494 B2 | 12/2008 | Gonzalez et al. |
| 7,520,956 B2 | 4/2009 | Samukawa et al. |
| 7,528,386 B2 | 5/2009 | Ruzic et al. |
| 7,725,208 B2 | 5/2010 | Shanmugasundram et al. |
| 7,737,702 B2 | 6/2010 | Pipitone |
| 7,764,140 B2 | 7/2010 | Nagarkatti et al. |
| 7,777,179 B2 | 8/2010 | Chen et al. |
| 7,783,375 B2 | 8/2010 | Shanmugasundram et al. |
| 7,847,247 B2 | 12/2010 | Denpoh |
| 8,140,292 B2 | 3/2012 | Wendt |
| 9,287,086 B2 * | 3/2016 | Brouk .................. C23C 14/345 |
| 2001/0014540 A1 | 8/2001 | Shan et al. |
| 2002/0038631 A1 | 4/2002 | Sumiya et al. |
| 2003/0033116 A1 | 2/2003 | Brcka et al. |
| 2004/0094402 A1 | 5/2004 | Gopalraja et al. |
| 2006/0088655 A1 | 4/2006 | Collins et al. |
| 2006/0130971 A1 | 6/2006 | Chang et al. |
| 2006/0226786 A1 | 10/2006 | Lin et al. |
| 2007/0186856 A1 | 8/2007 | Yasui et al. |
| 2007/0193975 A1 | 8/2007 | Wilson |
| 2007/0246163 A1 | 10/2007 | Paterson et al. |
| 2009/0077150 A1 | 3/2009 | Wendt |
| 2009/0255800 A1 | 10/2009 | Koshimizu |
| 2010/0072172 A1 | 3/2010 | Ui et al. |
| 2010/0154994 A1 * | 6/2010 | Fischer ............. H01J 37/32623 156/345.24 |
| 2010/0208409 A1 | 8/2010 | Bluck et al. |
| 2010/0276273 A1 | 11/2010 | Heckman et al. |
| 2011/0089023 A1 | 4/2011 | Tanaka et al. |
| 2011/0095689 A1 | 4/2011 | Gilbert |
| 2011/0226617 A1 | 9/2011 | Hofmann et al. |
| 2011/0259851 A1 | 10/2011 | Brouk et al. |
| 2012/0052599 A1 | 3/2012 | Brouk et al. |
| 2012/0187844 A1 | 7/2012 | Brouk et al. |
| 2012/0217221 A1 | 8/2012 | Hoffman et al. |
| 2012/0318456 A1 | 12/2012 | Brouk et al. |
| 2012/0319584 A1 | 12/2012 | Brouk et al. |
| 2014/0062495 A1 | 3/2014 | Carter et al. |

FOREIGN PATENT DOCUMENTS

| | | | |
|---|---|---|---|
| EP | 1129481 B1 | | 2/2012 |
| GB | 2382459 A | | 5/2003 |
| GB | 2400613 A | | 10/2004 |
| JP | 60-126832 | | 7/1985 |
| JP | 0214572 A | | 5/1990 |
| JP | 04-193329 A | | 7/1992 |
| JP | 09293600 | | 11/1997 |
| JP | 2003133404 A | | 5/2003 |
| JP | 2004193564 | | 7/2004 |
| JP | 200971133 | | 4/2009 |
| JP | 2011222292 A | * | 11/2011 |
| TW | 200811905 A | | 3/2008 |
| WO | 0215222 A2 | | 2/2002 |
| WO | 2010013476 A1 | | 2/2010 |
| WO | 2010126893 A2 | | 11/2010 |
| WO | 2012030500 A1 | | 3/2012 |
| WO | 2012103101 A1 | | 8/2012 |
| WO | 2013016619 | | 1/2013 |

OTHER PUBLICATIONS

Yamamoto, Shusaku, "Response to Japanese Office Action re Application No. 2012-508593", Aug. 16, 2013, p. 9, Published in: JP.

Duk Yeul Baek, "Korean Office Action re Applcation No. 10-2011-7009075", Mar. 25, 2013, p. 2, Published in: KR.

Brayton, John Joseph, "Office Action re U.S. Appl. No. 12/870,837", Mar. 22, 2013, p. 46, Published in: US.

Abraham, Ibrahime A., "Office Action re U.S. Appl. No. 12/767,775", Apr. 25, 2013, p. 28, Published in: US.

Brayton, John Joseph, "Office Action re U.S. Appl. No. 13/193,345", Jun. 6, 2013, p. 8, Published in: US.

Brayton, John Joseph, "Office Action re U.S. Appl. No. 13/193,299", Aug. 8, 2013, p. 7, Published in: US.

O'Dowd, Sean R., "Response to Office Action re U.S. Appl. No. 12/870,837", Aug. 22, 2013, p. 9, Published in: US.

Baharlou, Simin, "International Preliminary Report on Patentability re Application No. PCT/US2011/047467", Mar. 14, 2013, p. 7, Published in: CH.

O'Dowd, Sean R. , "Response to Office Action re U.S. Appl. No. 12/767,775", Mar. 17, 2013, p. 6, Published in: US.

O'Dowd, Sean R., "Response to Office Action re U.S. Appl. No. 12/767,775", Jul. 25, 2013, p. 7, Published in: US.

Gruber, Stephen S., "Response to Office Action re U.S. Appl. No. 13/193,345", Jul. 30, 2013, p. 9, Published in: US.

Gruber, Stephen S., "Response to Office Action re U.S. Appl. No. 13/193,299", Aug. 28, 2013, p. 9, Published in: US.

Jeon, M., et al., "Hydrogenated amorphous silicon film as intrinsic passivation layer deposited at various temperatures using RF remote-PECVD technique", Current Applied Physics, Nov. 12, 2009, pp. S237-S240, vol. 10, No. 2010, Publisher: Elsevier B.V., Published in: US.

Bruno, G., et al., "Real time ellipsometry for monitoring plasma-assisted epitaxial growth of GaN", Applied Surface Sci., Jul. 7, 2006, pp. 219-223, vol. 253, No. 2006, Publisher: Elsevier B.V., Published in: US.

Giangregorio, M.M., et al., "Role of plasma activation in tailoring the nanostructure of multifunctional oxides thin films", Applied Surface Sci., Sep. 10, 2008, pp. 5396-5400, vol. 255, No. 2009, Publisher: Elsevier B.V., Published in: US.

Vahedi, V., et al., "Verification of frequency scaling laws for capacitive radio-frequency discharges using two-dimensional simulations", Phys. Fluids B, Jul. 1993, pp. 2719-2729, vol. 5, No. 7, Publisher: Am. Inst. of Physics, Published in: US.

(56) References Cited

OTHER PUBLICATIONS

Rauf, S., et al., "Nonlinear Dynamics of Radio Frequency Plasma Processing Reactors Powered by Multifrequency Sources", IEEE Transactions on Plasma Science, Oct. 5, 1999, pp. 1329-1338, vol. 27, No. 5, Publisher: IEEE.

Raoux, S., et al., "Remote microwave plasma source for cleaning chemical vapor deposition chambers; Technology for reducing global warming gas emissions", J. Vac. Sci. Technol. B Mar./Apr. 1999, 1999, pp. 477-485, vol. 17, No. 2, Publisher: AM. Vacuum Soc'y, Published in: US.

Gangoli, S.P., et al., "Production and transport chemistry of atomic fluorine in remote plasma source and cylindrical reaction chamber", J. Phys. D: Appl. Phys., Aug. 16, 2007, pp. 5140-5154, vol. 40, No. 2007, Publisher: IOP Publishing Ltd., Published in: UK.

Yun, Y.B., et al., "Effects of various additive gases on chemical dry etching rate enhancement of low-k SiOCH layer in F2/Ar remote plasmas", Thin Solid Films, Aug. 15, 2007, pp. 3549-3553, vol. 516, No. 2008, Publisher: Elsevier B.V., Published in: US.

Kuo, M.S., et al., "Influence of C4F8/Ar-based etching and H2-based remote plasma ashing processes on ultralow k materials modifications", J. Vac. Sci. Technol. B, Mar./Apr. 2010, Mar. 19, 2010, pp. 284-294, vol. 28, No. 2, Publisher: Am. Vacuum Soc'y, Published in: US.

Heil, S.B.S., et al., "Deposition of TiN and HfO2 in a commercial 200 mm plasma atomic layer deposition reactor", J. Vac. Sci. Technol. A, Sep./Oct. 2007, Jul. 31, 2007, pp. 1357-1366, vol. 25, No. 5, Publisher: Am. Vacuum Soc'y, Published in: US.

Kim, J.Y., et al., "Remote plasma enhanced atomic layer deposition of TiN thin films using metalorganic precursor", J. Vac. Sci. Technol. A, Jan./Feb. 2004, Nov. 13, 2003, pp. 8-12, vol. 22, No. 1, Published: Am. Vacuum Soc'y, Published in: US.

Wakeham, S.J., et al., "Low temperature remote plasma sputtering of indium tin oxide for flexible display applications", Thin Solid Films, May 12, 2009, pp. 1355-1358, vol. 519, No. 2009, Publisher: Elsevier B.V.

Ohachi, T., et al., "Measurement of nitrogen atomic flux for RF-MBE growth of GaN and AlN on Si substrates", J. of Crystal Growth, Jan. 20, 2009, pp. 2987-2991, vol. 311, No. 2009, Publisher: Elsevier B.V.

Honda, S., et al., "Hydrogenation of polycrystalline silicon thin films", Thin Solid Films, Oct. 5, 2005, pp. 144-148, vol. 501, No. 2006, Publisher: Elsevier B.V., Published in: US.

Buzzi, F.L., et al., "Energy Distribution of Bombarding Ions in Plasma Etching of Dielectrics", AVS 54th International Symposium, Oct. 15, 2007, Publisher: Univ. of Wisconsin—Madison, Published in: US.

Bryns, B., et al., "A VHF driven coaxial atmospheric air plasma: electrical and optical characterization", Dec. 16, 2011, pp. 1-18, No. Rev. 2-0, Publisher: N. C. St. U., Dep't of Nuclear Engr., Published in: US.

Kudelka, Stephan, Supplementary European Search Report re EP Application 10 77 0205.2, PCT/US10/032582, Jan. 30, 2013, p. 8, Published in: NL.

Emsellem, G., "Electrodeless Plasma Thruster Design Characteristics", Jul. 11, 2005, p. 22, Publisher: 41st Joint Propulsion Conference, Tucson, Published in: US.

George, M.A., et al., "Silicon Nitride Arc Thin Films by New Plasma Enhanced Chemical Vapor Deposition Source Technology", Jul. 7, 2011, pp. 1-5, Article downloaded from www.generalplasma.com, Published in: US.

Krolak, M, "Matthew Krolak's MyElectricEngine.Com Megnetoplasmadynamic (MPD) Thruster Design", Apr. 28, 2011, p. 7, Webpage downloaded from http://myelectricengine.com/projects/mpdthruster/mpdthruster.html, Published in: US.

McLeod, Austin, Office Action re U.S. Appl. No. 12/767,775, Oct. 17, 2012, Published in: US.

Brayton, John J., Office Action re U.S. Appl. No. 12/870,837, Dec. 19, 2012, Published in: US.

Atkinson, Gerard, International Search Report and Written Opinion re Application No. PCT/US10/032582, Feb. 21, 2011, Published in: AU.

Mitrovic, Bayer, International Search Report and Written Opinion re Application No. PCT/US11/047467, Feb. 12, 2011, Published in: AU.

Guinea, William, International Search Report and Written Opinion re Application No. PCT/US12/048504, Sep. 17, 2012, Published in: AU.

Lindner, Nora, International Preliminary Report on Patentability re Application PCT/US2010/032582, Nov. 1, 2011, p. 8, Published in: CH.

Rabbani, Firoozeh, International Search Report and Written Opinion re application No. PCT/US2012/022380, Mar. 14, 2012, Published in: AU.

Devlin, Martin, International Search Report and Written Opinion re application No. PCT/US2012/029953, May 28, 2012, p. 11, Published in: AU.

Gruber, Stephen S., Response to Office Action dated Dec. 19, 2012 re U.S. Appl. No. 12/870,837, Jan. 9, 2013, p. 8, Published in: US.

Silapunt, et al., "Ion bombardment energy control for selective fluorocarbon plasma etching", Mar. 22, 2004, Published in: US.

Wang, S.B., et al., "Control of ion energy distribution at substrates during plasma processing", J. Applied Physics, Jul. 15, 2000, pp. 643-646, vol. 88, No. 2, Publisher: Am. Inst. of Physics, Published in: US.

Ramachandran, Mani, "International Search Report and Written Opinion re Application No. PCT/US2013/056634", Nov. 15, 2013, p. 10, Published in: AU.

Williams, Jim, "International Search Report and Written Opinion re Application No. PCT/US2013/056647", Oct. 30, 2013, p. 10, Published in: AU.

Mitrovic, Bayer, "International Search Report and Written Opinion re Application No. PCT/US2013/056657", Oct. 28, 2013, p. 11, Published in: AU.

Williams, Jim, "International Search Report and Written Opinion re Application No. PCT/US2013/056851", Nov. 18, 2013, p. 11, Published in: AU.

Panta, Kusha, "International Search Report and Written Opinion re Application No. PCT/US2013/056659", Nov. 8, 2013, p. 11, Published in: AU.

Xiubo, et al., "Charging of dielectric substrate materials during plasma immersion ion implantation", Nov. 9, 2001, p. 7, Published in: HK.

SIPO, "Chinese Office Action re Application No. 201080003206.X", May 23, 2014, p. 6, Published in: CN.

Yafeng, "Chinese Office Action re Application No. 201080003206.X", Sep. 4, 2013, p. 15, Published in: CN.

Sathiraju, Srinivas, "Office Action re U.S. Appl. No. 13/597,032", Jun. 20, 2014, p. 42, Published in: US.

Abraham, Ibrahime A., "Office Action re U.S. Appl. No. 12/767,775", Jul. 1, 2014, p. 48, Published in: US.

Brayton, John Joseph, "Office Action re U.S. Appl. No. 13/193,345", Jul. 7, 2014, p. 26, Published in: US.

Brayton, John Joseph, "Office Action re U.S. Appl. No. 13/193,299", Sep. 26, 2014, p. 37, Published in: US.

Brayton, John Joseph, "Office Action re U.S. Appl. No. 13/193,299", Dec. 18, 2013, p. 43, Published in: US.

Brayton, John Joseph, "Office Action re U.S. Appl. No. 12/870,837", Dec. 20, 2013, p. 33, Published in: US.

Baharlou, Simin, "International Preliminary Report on Patentability re Application No. PCT/US2012/048504", Feb. 6, 2014, p. 11, Published in: CH.

O'Dowd, Sean R., "Response to Office Action re U.S. Appl. No. 12/870,837", Mar. 20, 2014, p. 8, Published in: US.

Gruber, Stephen S., "Response to Office Action re U.S. Appl. No. 13/193,299", May 19, 2014, p. 18, Published in: US.

O'Dowd, Sean R., "Response to Office Action re U.S. Appl. No. 13/193,345", Mar. 7, 2014, p. 7, Published in: US.

O'Dowd, Sean R., "Response to Office Action re U.S. Appl. No. 12/767,775", Nov. 3, 2014, p. 13, Published in: US.

TIPO, "Taiwan Office Action re Application No. 099113815", Jan. 27, 2014, p. 6, Published in: TW.

(56) References Cited

OTHER PUBLICATIONS

TIPO, "Taiwan Office Action re Application No. 099113815", Jun. 18, 2014, p. 2, Published in: TW.
TIPO, "Taiwan Office Action re Application No. 101127182", Aug. 11, 2014, p. 11, Published in: TW.
Abraham, Ibrahime A., "Office Action re U.S. Appl. No. 12/767,775", Dec. 15, 2014, p. 37, Published in: US.
Ahmed, Shamim, "Office Action re U.S. Appl. No. 14/011,305", Dec. 4, 2014, p. 28, Published in: US.
O'Dowd, Sean R., "Response to Office Action re U.S. Appl. No. 13/597,032", Dec. 16, 2014, p. 11, Published in: US.
Yafeng, Zhang, "Chinese Office Action re Application No. 201080003206.X", Nov. 26, 2014, p. 6, Published in: CN.
O'Dowd, Sean, "Response to Office Action re U.S. Appl. No. 13/193,345", Dec. 8, 2014, p. 8, Published in: US.
Wittmann-Regis, Agnes, "International Preliminary Report on Patentability re Application No. PCT/US2013/056634", Mar. 12, 2015, p. 7, Published in: CH.
Moku, Tetsuji, "Japanese Office Action re Application No. 2013-527088", Apr. 21, 2015, p. 10, Published in: JP.
Moku, Tetsuji, "Japanese Office Action re Application No. 2014-523-057", Apr. 21, 2015, p. 11, Published in: JP.
Brayton, John Joseph, "Restriction Requirement re U.S. Appl. No. 13/597,050", Jan. 27, 2015, p. 7, Published in: US.
Brayton, John Joseph, "Restriction Requirement re U.S. Appl. No. 13/596,976", Feb. 23, 2015, p. 8, Published in: US.
Brayton, John Joseph, "Office Action re U.S. Appl. No. 14/606,857", Apr. 8, 2015, p. 51, Published in: US.
Brayton, John Joseph, "Office Action re U.S. Appl. No. 12/870,837", Apr. 9, 2015, p. 40, Published in: US.
Sathiraju, Srinivas, "Office Action re U.S. Appl. No. 13/597,032", Apr. 9, 2015, p. 32, Published in: US.
Brayton, John Joseph, "Office Action re U.S. Appl. No. 13/193,345", Apr. 16, 2015, p. 34, Published in: US.
Nickitas-Etienne, Athina, "International Preliminary Report on Patentability re Application No. PCT/US2013/056647", Mar. 12, 2015, p. 7, Published in: CH.
Mohri, Mineko, "International Preliminary Report on Patentability re Application No. PCT/US2013/056657", Mar. 12, 2015, p. 8, Published in: CH.
Mohri, Mineko, "International Preliminary Report on Patentability re Application No. PCT/US2013/056659", Mar. 12, 2015, p. 8, Published in: CH.
Nakamura, Yukari, "International Preliminary Report on Patentability re Application No. PCT/US2013/056851", Mar. 12, 2015, p. 8, Published in: CH.
O'Dowd, Sean R., "Office Action Response re U.S. Appl. No. 12/767,775", Feb. 27, 2015, p. 6, Published in: US.
Gruber, Stephen S., "Response to Restriction Requirement re U.S. Appl. No. 13/597,050", Mar. 26, 2015, p. 11, Published in: US.
O'Dowd, Sean R., "Response to Office Action re U.S. Appl. No. 13/193,299", Mar. 26, 2015, p. 7, Published in: US.
Gruber, Stephen S. "Response to Office Action re U.S. Appl. No. 14/011,305", Mar. 4, 2015, p. 10, Published in: US.
SIPO, "Chinese Office Action re Application No. 201180046783.1", Mar. 24, 2015, p. 18, Published in: CN.
Brayton, John Joseph, "Office Action re U.S. Appl. No. 13/193,299", May 21, 2015, p. 24, Published in: US.
Abraham, Ibrahime A., "Office Action re U.S. Appl. No. 12/767,775", Jun. 17, 2015, p. 28, Published in: US.
Brayton, John Joseph, "Office Action re U.S. Appl. No. 13/597,050", Jul. 17, 2015, p. 86, Published in: US.
O'Dowd, Sean R., "Response to Office Action re U.S. Appl. No. 13/596,976", Jul. 23, 2015, p. 10, Published in: US.
Masaaki, Awano, "Japanese Office Action re Application No. 2012-508593", Sep. 11, 2013, p. 7, Published in: JP.
Abraham, Ibrahime A., "Office Action re U.S. Appl. No. 12/767,775", Sep. 10, 2013, p. 30, Published in: US.
O'Dowd, Sean R., "Reponse to Office Action re U.S. Appl. No. 12/767,775", Nov. 5, 2013, p. 6, Published in: US.
Brayton, John Joseph, "Office Action re U.S. Appl. No. 13/193,345", Nov. 7, 2013, p. 36, Published in: US.
SIPO, "Chinese Office Action re Application No. 201280047162.X", Sep. 6, 2015, p. 18, Published in: CN.
Aguilar, Maria, "European Search Report re Application No. EP11822326", Oct. 9, 2015, p. 3, Published in: EP.
Brayton, John Joseph, "US Office Action re U.S. Appl. No. 13/596,976", Nov. 6, 2015, p. 77, Published in: US.
O'Dowd, Sean R., "Response to Office Action re U.S. Appl. No. 14/606,857", Jul. 8, 2015, p. 10, Published in: US.
Percival, Shane, "Response to Office Action re U.S. Appl. No. 13/597,032", Aug. 7, 2015, p. 17, Published in: US.
O'Dowd, Sean, "Response to Office Action re U.S. Appl. No. 13/193,299", Aug. 20, 2015, p. 10, Published in: US.
O'Dowd, Sean R., "Response to Office Action re U.S. Appl. No. 12/870,837", Oct. 6, 2015, p. 7, Published in: US.
O'Dowd, Sean, "Response to Office Action re U.S. Appl. No. 13/193,345", Oct. 13, 2015, p. 7, Published in: US.
O'Dowd, Sean, "Response to Office Action re U.S. Appl. No. 12/767,775", Oct. 19, 2015, p. 9, Published in: US.
TIPO, "Taiwan Search Report re Application No. 102130565", Aug. 20, 2015, p. 4, Published in: TW.
Taiwan Intellectual Property Office, "Taiwan Office Action re Application No. 102130565", Apr. 11, 2016, p. 2, Published in: TW.
Kim, Joo-Seung, "Korean Office Action Re Application No. 1020157007516", Feb. 15, 2017, p. 18 Published in: KR.

\* cited by examiner

SYSTEMS AND METHODS FOR MONITORING FAULTS, ANOMALIES, AND OTHER CHARACTERISTICS OF A SWITCHED MODE ION ENERGY DISTRIBUTION SYSTEM

FIELD OF THE DISCLOSURE

The present disclosure relates generally to plasma processing. In particular, but not by way of limitation, the present invention relates to methods and apparatuses for plasma-assisted etching, deposition, and/or other plasma-assisted processes.

BACKGROUND OF THE DISCLOSURE

Many types of semiconductor devices are fabricated using plasma-based etching techniques. If it is a conductor that is etched, a negative voltage with respect to ground may be applied to the conductive substrate so as to create a substantially uniform negative voltage across the surface of the substrate conductor, which attracts positively charged ions toward the conductor, and as a consequence, the positive ions that impact the conductor have substantially the same energy.

If the substrate is a dielectric, however, a non-varying voltage is ineffective to place a voltage across the surface of the substrate. But an AC voltage (e.g., high frequency) may be applied to the conductive plate (or chuck) so that the AC field induces a voltage on the surface of the substrate. During the positive half of the AC cycle, the substrate attracts electrons, which are light relative to the mass of the positive ions; thus many electrons will be attracted to the surface of the substrate during the positive part of the cycle. As a consequence, the surface of the substrate will be charged negatively, which causes ions to be attracted toward the negatively-charged surface. And when the ions impact the surface of the substrate, the impact dislodges material from the surface of the substrate—effectuating the etching.

In many instances, it is desirable to have a narrow ion energy distribution, but applying a sinusoidal waveform to the substrate induces a broad distribution of ion energies, which limits the ability of the plasma process to carry out a desired etch profile. Known techniques to achieve a narrow ion energy distribution are expensive, inefficient, difficult to control, and may adversely affect the plasma density. As a consequence, these known techniques have not been commercially adopted. Accordingly, a system and method are needed to address the shortfalls of present technology and to provide other new and innovative features.

SUMMARY

Illustrative embodiments of the present disclosure that are shown in the drawings are summarized below. These and other embodiments are more fully described in the Detailed Description section. It is to be understood, however, that there is no intention to limit the invention to the forms described in this Summary of the Invention or in the Detailed Description. One skilled in the art can recognize that there are numerous modifications, equivalents, and alternative constructions that fall within the spirit and scope of the invention as expressed in the claims.

According to one embodiment, the invention may be characterized as a method for establishing one or more plasma sheath voltages. The method may comprise providing a modified periodic voltage function to a substrate support of a plasma chamber. The substrate support can be coupled to a substrate that is configured for processing in the plasma. Also, the modified periodic voltage function can comprise a periodic voltage function modified by an ion current compensation, Ic. The modified periodic voltage function can comprise pulses and a portion between the pulses. Also, the pulses can be a function of the periodic voltage function, and a slope of the portion between the pulses can be a function of the ion current compensation, Ic. The method can further comprise accessing an effective capacitance value, $C_1$, that represents at least a capacitance of the substrate support. The method finally can identify a value of the ion current compensation, Ic, that will result in a defined ion energy distribution function of ions reaching a surface of the substrate, where the identifying is a function of the effective capacitance, $C_1$, a slope, $dV_o/dt$, of the portion between the pulses.

According to another embodiment, the invention may be described as a method for biasing a plasma so as to achieve a defined ion energy at a surface of a substrate within a plasma processing chamber. The method may include applying a modified periodic voltage function comprising a periodic voltage function modified by an ion current compensation to a substrate support. The method may further include sampling at least one cycle of the modified periodic voltage function to generate voltage data points. The method may further include estimating a value of a first ion energy at the substrate surface from the voltage data points. Also, the method may include adjusting the modified periodic voltage function until the first ion energy equals the define ion energy.

According to yet another embodiment, the invention may be characterized as a method to achieve an ion energy distribution function width. The method may include providing a modified periodic voltage function to a substrate support of a plasma processing chamber. The method may further include sampling at least two voltages from the non-sinusoidal waveform at a first time and at a second time. The method can additionally include calculating a slope of the at least two voltages as dV/dt. Also, the method may include comparing the slope to a reference slope known to correspond to an ion energy distribution function width. Finally, the method may include adjusting the modified periodic voltage function so that the slope approaches the reference slope.

Another aspect of the disclosure can be characterized as an apparatus comprising a power supply, an ion current compensation component, and a controller. The power supply can provide a periodic voltage function having pulses and a portion between the pulses. The ion current compensation component can modify a slope of the portion between the pulses to form a modified periodic voltage function. The modified period voltage function can be configured for providing to a substrate support for processing in a plasma processing chamber. The controller can be coupled to the switch-mode power supply and the ion current compensation component. The controller can also be configured to identify a value of the ion current compensation that if provided to the substrate support, would result in a defined ion energy distribution function of ions reaching a surface of the substrate.

Yet another aspect of the disclosure can be characterized as a non-transitory, tangible computer readable storage medium, encoded with processor readable instructions to perform a method for monitoring an ion current of a plasma configured to process a substrate. The method can include sampling a modified periodic voltage function given an ion current compensation having a first value, and sampling the modified periodic voltage function given the ion current compensation having a second value. The method further can include determining a slope of the modified periodic voltage function as a function of time based on the first and second sampling. The method also determines a slope of the modified periodic voltage function as a function of time based on the first and second sampling. The method finally can include calculating a third value of the ion current compensation, based on the slope, at which a constant voltage on the substrate will exist for at least one cycle of the modified periodic voltage function.

These and other embodiments are described in further detail herein.

BRIEF DESCRIPTION OF THE DRAWINGS

Various objects and advantages and a more complete understanding of the present invention are apparent and more readily appreciated by reference to the following Detailed Description and to the appended claims when taken in conjunction with the accompanying Drawings where like or similar elements are designated with identical reference numerals throughout the several views and wherein:

DETAILED DESCRIPTION

Figure 1:
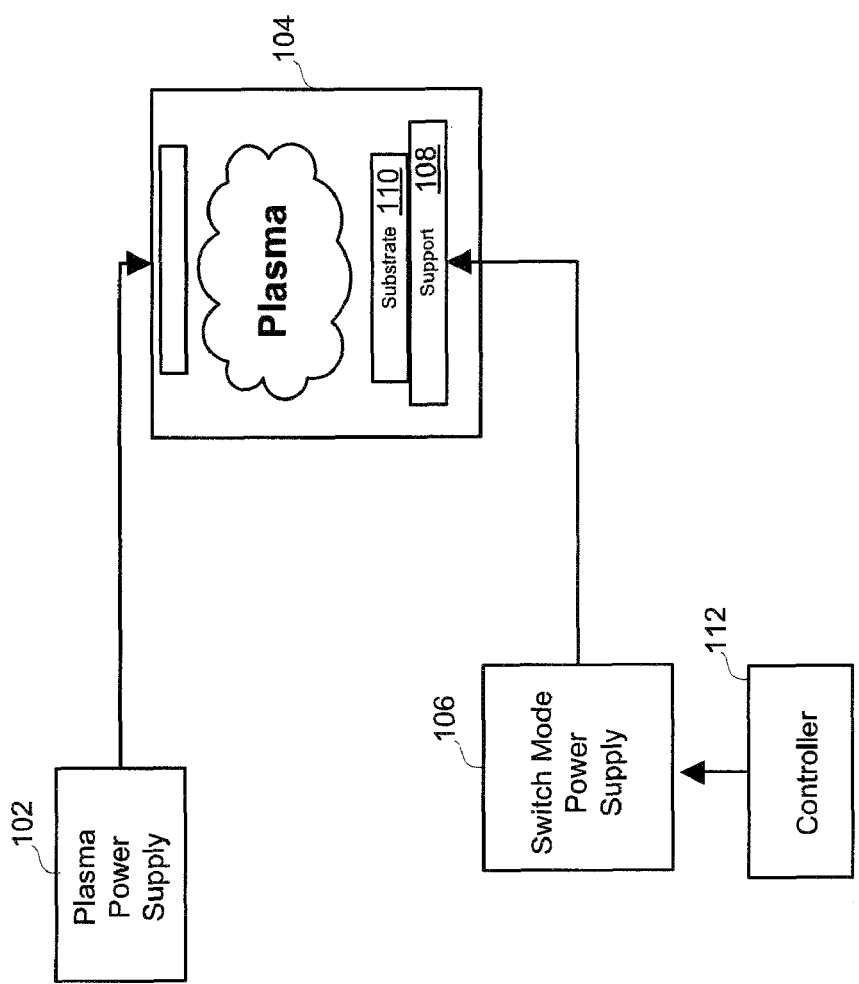
FIG. 1 illustrates a block diagram of a plasma processing system in accordance with one implementation of the present invention.

An exemplary embodiment of a plasma processing system is shown generally in FIG. 1. As depicted, a plasma power supply 102 is coupled to a plasma processing chamber 104 and a switch-mode power supply 106 is coupled to a support 108 upon which a substrate 110 rests within the chamber 104. Also shown is a controller 112 that is coupled to the switch-mode power supply 106.

In this exemplary embodiment, the plasma processing chamber 104 may be realized by chambers of substantially conventional construction (e.g., including a vacuum enclosure which is evacuated by a pump or pumps (not shown)). And, as one of ordinary skill in the art will appreciate, the plasma excitation in the chamber 104 may be by any one of a variety of sources including, for example, a helicon type plasma source, which includes magnetic coil and antenna to ignite and sustain a plasma 114 in the reactor, and a gas inlet may be provided for introduction of a gas into the chamber 104.

As depicted, the exemplary plasma chamber 104 is arranged and configured to carry out plasma-assisted etching of materials utilizing energetic ion bombardment of the substrate 110, and other plasma processing (e.g., plasma deposition and plasma assisted ion implantation). The plasma power supply 102 in this embodiment is configured to apply power (e.g., RF power) via a matching network (not shown)) at one or more frequencies (e.g., 13.56 MHz) to the chamber 104 so as to ignite and sustain the plasma 114. It should be understood that the present invention is not limited to any particular type of plasma power supply 102 or source to couple power to the chamber 104, and that a variety of frequencies and power levels may be may be capacitively or inductively coupled to the plasma 114.

As depicted, a dielectric substrate 110 to be treated (e.g., a semiconductor wafer), is supported at least in part by a support 108 that may include a portion of a conventional wafer chuck (e.g., for semiconductor wafer processing). The support 108 may be formed to have an insulating layer between the support 108 and the substrate 110 with the substrate 110 being capacitively coupled to the platforms but may float at a different voltage than the support 108.

As discussed above, if the substrate 110 and support 108 are conductors, it is possible to apply a non-varying voltage to the support 108, and as a consequence of electric conduction through the substrate 110, the voltage that is applied to the support 108 is also applied to the surface of the substrate 110.

When the substrate 110 is a dielectric, however, the application of a non-varying voltage to the support 108 is ineffective to place a voltage across the treated surface of the substrate 110. As a consequence, the exemplary switch-mode power supply 106 is configured to be controlled so as to effectuate a voltage on the surface of the substrate 110 that is capable of attracting ions in the plasma 114 to collide with the substrate 110 so as to carry out a controlled etching and/or deposition of the substrate 110, and/or other plasma-assisted processes.

Moreover, as discussed further herein, embodiments of the switch-mode power supply 106 are configured to operate so that there is an insubstantial interaction between the power applied (to the plasma 114) by the plasma power supply 102 and the power that is applied to the substrate 110 by the switch-mode power supply 106. The power applied by the switch-mode power supply 106, for example, is controllable so as to enable control of ion energy without substantially affecting the density of the plasma 114.

Furthermore, many embodiments of the exemplary switch-mode supply 106 depicted in FIG. 1 are realized by relatively inexpensive components that may be controlled by relatively simple control algorithms. And as compared to prior art approaches, many embodiments of the switch mode power supply 106 are much more efficient; thus reducing energy costs and expensive materials that are associated with removing excess thermal energy.

One known technique for applying a voltage to a dielectric substrate utilizes a high-power linear amplifier in connection with complicated control schemes to apply power to a substrate support, which induces a voltage at the surface of the substrate. This technique, however, has not been adopted by commercial entities because it has not proven to be cost effective nor sufficiently manageable. In particular, the linear amplifier that is utilized is typically large, very expensive, inefficient, and difficult to control. Furthermore, linear amplifiers intrinsically require AC coupling (e.g., a blocking capacitor) and auxiliary functions like chucking are achieved with a parallel feed circuit which harms AC spectrum purity of the system for sources with a chuck.

Another technique that has been considered is to apply high frequency power (e.g., with one or more linear amplifiers) to the substrate. This technique, however, has been found to adversely affect the plasma density because the high frequency power that is applied to the substrate affects the plasma density.

In some embodiments, the switch-mode power supply 106 depicted in FIG. 1 may be realized by buck, boost, and/or buck-boost type power technologies. In these embodiments, the switch-mode power supply 106 may be controlled to apply varying levels of pulsed power to induce a potential on the surface of the substrate 110.

Figure 2:
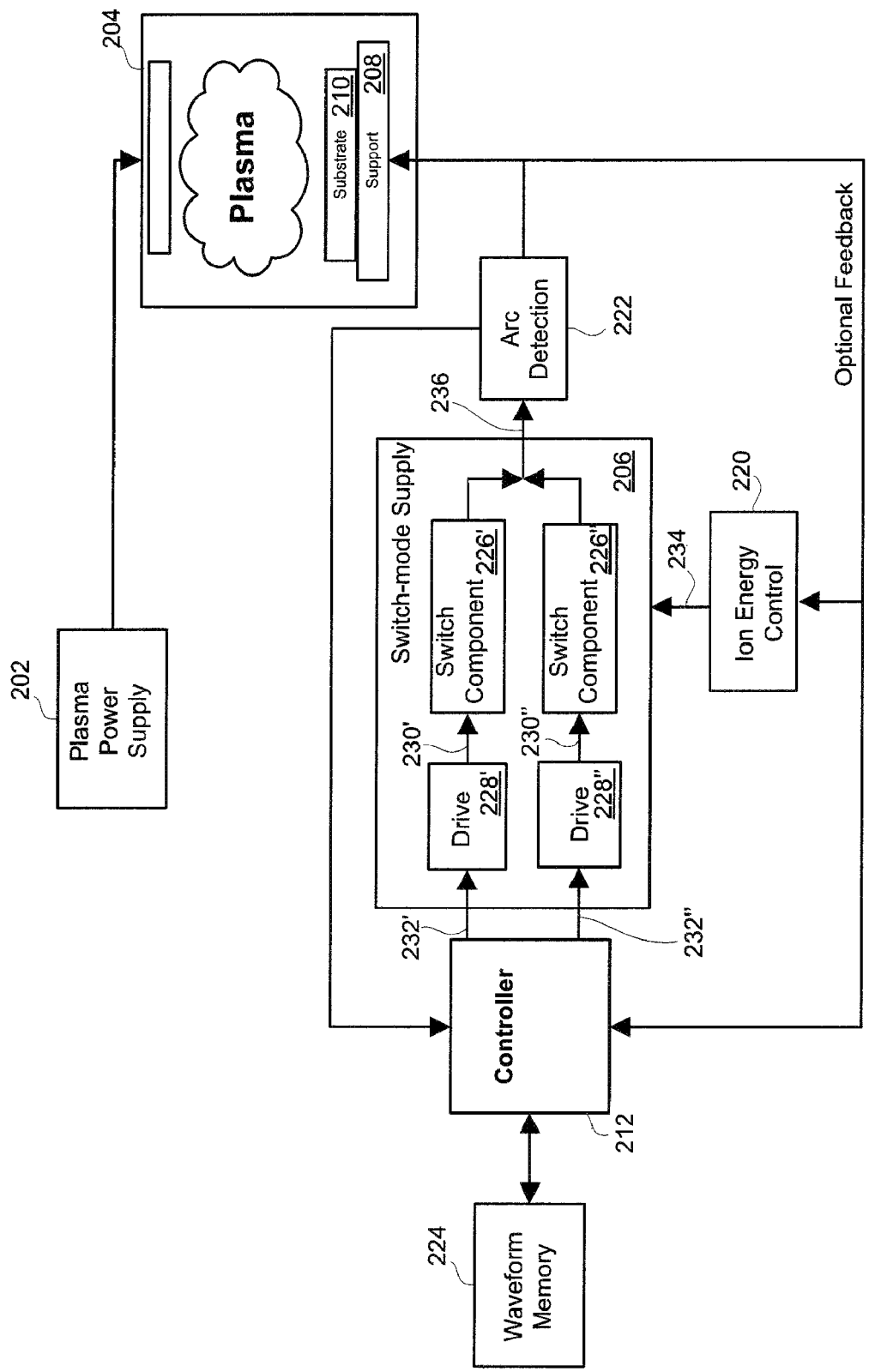
FIG. 2 is a block diagram depicting an exemplary embodiment of the switch-mode power system depicted in FIG. 1.

In other embodiments, the switch-mode power supply 106 is realized by other more sophisticated switch mode power and control technologies. Referring next to FIG. 2, for example, the switch-mode power supply described with reference to FIG. 1 is realized by a switch-mode bias supply 206 that is utilized to apply power to the substrate 110 to effectuate one or more desired energies of the ions that bombard the substrate 110. Also shown are an ion energy control component 220, an arc detection component 222, and a controller 212 that is coupled to both the switch-mode bias supply 206 and a waveform memory 224.

The illustrated arrangement of these components is logical; thus the components can be combined or further separated in an actual implementation, and the components can be connected in a variety of ways without changing the basic operation of the system. In some embodiments for example, the controller 212, which may be realized by hardware, software, firmware, or a combination thereof, may be utilized to control both the power supply 202 and switch-mode bias supply 206. In alternative embodiments, however, the power supply 202 and the switch-mode bias supply 206 are realized by completely separated functional units. By way of further example, the controller 212, waveform memory 224, ion energy control portion 220 and the switch-mode bias supply 206 may be integrated into a single component (e.g., residing in a common housing) or may be distributed among discrete components.

The switch-mode bias supply 206 in this embodiment is generally configured to apply a voltage to the support 208 in a controllable manner so as to effectuate a desired (or defined) distribution of the energies of ions bombarding the surface of the substrate. More specifically, the switch-mode bias supply 206 is configured to effectuate the desired (or defined) distribution of ion energies by applying one or more particular waveforms at particular power levels to the substrate. And more particularly, responsive to an input from the ion energy control portion 220, the switch-mode bias supply 206 applies particular power levels to effectuate particular ion energies, and applies the particular power levels using one or more voltage waveforms defined by waveform data in the waveform memory 224. As a consequence, one or more particular ion bombardment energies may be selected with the ion control portion to carry out controlled etching of the substrate (or other forms of plasma processing).

As depicted, the switch-mode power supply 206 includes switch components 226', 226" (e.g., high power field effect transistors) that are adapted to switch power to the support 208 of the substrate 210 responsive to drive signals from corresponding drive components 228', 228". And the drive signals 230', 230" that are generated by the drive components 228', 228" are controlled by the controller 212 based upon timing that is defined by the content of the waveform memory 224. For example, the controller 212 in many embodiments is adapted to interpret the content of the waveform memory and generate drive-control signals 232', 232", which are utilized by the drive components 228', 228" to control the drive signals 230', 230" to the switching components 226', 226". Although two switch components 226', 226", which may be arranged in a half-bridge configuration, are depicted for exemplary purposes, it is certainly contemplated that fewer or additional switch components may be implemented in a variety of architectures (e.g., an H-bridge configuration).

In many modes of operation, the controller 212 (e.g., using the waveform data) modulates the timing of the drive-control signals 232', 232" to effectuate a desired waveform at the support 208 of the substrate 210. In addition, the switch mode bias supply 206 is adapted to supply power to the substrate 210 based upon an ion-energy control signal 234, which may be a DC signal or a time-varying waveform. Thus, the present embodiment enables control of ion distribution energies by controlling timing signals to the switching components and controlling the power (controlled by the ion-energy control component 220) that is applied by the switching components 226', 226".

In addition, the controller 212 in this embodiment is configured, responsive to an arc in the plasma chamber 204 being detected by the arc detection component 222, to carry out arc management functions. In some embodiments, when an arc is detected the controller 212 alters the drive-control signals 232', 232" so that the waveform applied at the output 236 of the switch mode bias supply 206 extinguishes arcs in the plasma 214. In other embodiments, the controller 212 extinguishes arcs by simply interrupting the application of drive-control signals 232', 232" so that the application of power at the output 236 of the switch-mode bias supply 206 is interrupted.

Figure 3:
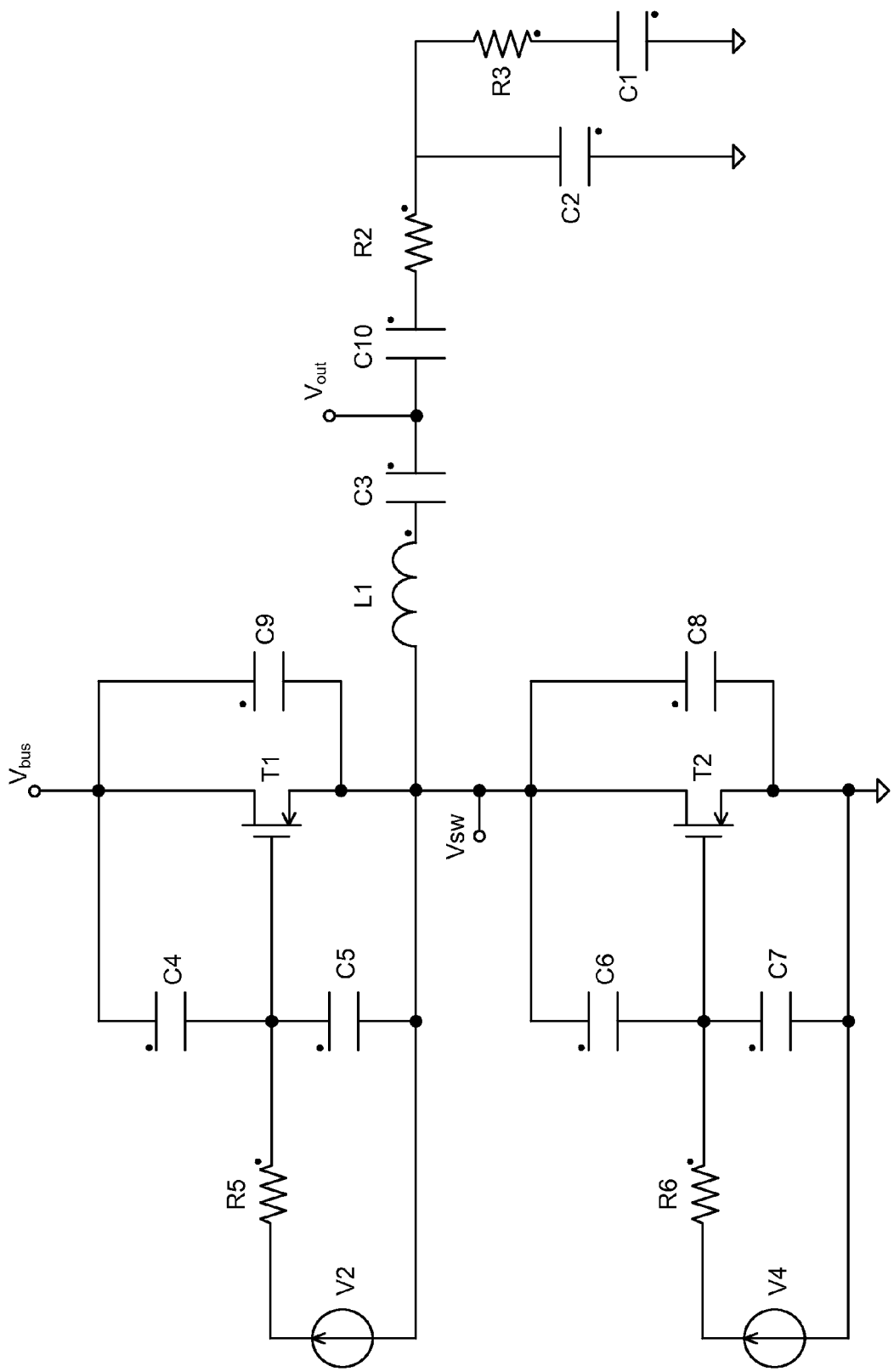
FIG. 3 is a schematic representation of components that may be utilized to realize the switch-mode bias supply described with reference to FIG. 2.

Referring next to FIG. 3, it is a schematic representation of components that may be utilized to realize the switch-mode bias supply 206 described with reference to FIG. 2. As shown, the switching components T1 and T2 in this embodiment are arranged in a half-bridge (also referred to as or totem pole) type topology. Collectively, R2, R3, C1, and C2 represent a plasma load, C10 is an effective capacitance (also referred to herein as a series capacitance or a chuck capacitance), and C3 is an optional physical capacitor to prevent DC current from the voltage induced on the surface of the substrate or from the voltage of an electrostatic chuck (not shown) from flowing through the circuit. C10 is referred to as the effective capacitance because it includes the series capacitance (or also referred to as a chuck capacitance) of the substrate support and the electrostatic chuck (or e-chuck) as well as other capacitances inherent to the application of a bias such as the insulation and substrate. As depicted, L1 is stray inductance (e.g., the natural inductance of the conductor that feeds the power to the load). And in this embodiment, there are three inputs: Vbus, V2, and V4.

V2 and V4 represent drive signals (e.g., the drive signals 230', 230"output by the drive components 228', 228" described with reference to FIG. 2), and in this embodiment, V2 and V4 can be timed (e.g., the length of the pulses and/or the mutual delay) so that the closure of T1 and T2 may be modulated to control the shape of the voltage output Vout, which is applied to the substrate support. In many implementations, the transistors used to realize the switching components T1 and T2 are not ideal switches, so to arrive at a desired waveform, the transistor-specific characteristics are taken into consideration. In many modes of operation, simply changing the timing of V2 and V4 enables a desired waveform to be applied at Vout.

For example, the switches T1, T2 may be operated so that the voltage at the surface of the substrate 110, 210 is generally negative with periodic voltage pulses approaching and/or slightly exceeding a positive voltage reference. The value of the voltage at the surface of the substrate 110, 210 is what defines the energy of the ions, which may be characterized in terms of an ion energy distribution function (IEDF). To effectuate desired voltage(s) at the surface of the substrate 110, 210, the pulses at Vout may be generally rectangular and have a width that is long enough to induce a brief positive voltage at the surface of the substrate 110, 210 so as to attract enough electrons to the surface of the substrate 110, 210 in order to achieve the desired voltage(s) and corresponding ion energies.

The periodic voltage pulses that approach and/or slightly exceed the positive voltage reference may have a minimum time limited by the switching abilities of the switches T1, T2. The generally negative portions of the voltage can extend so long as the voltage does not build to a level that damages the switches. At the same time, the length of negative portions of the voltage should exceed an ion transit time.

Vbus in this embodiment defines the amplitude of the pulses measured at Vout, which defines the voltage at the surface of the substrate, and as a consequence, the ion energy. Referring briefly again to FIG. 2, Vbus may be coupled to the ion energy control portion, which may be realized by a DC power supply that is adapted to apply a DC signal or a time-varying waveform to Vbus.

Figure 4:
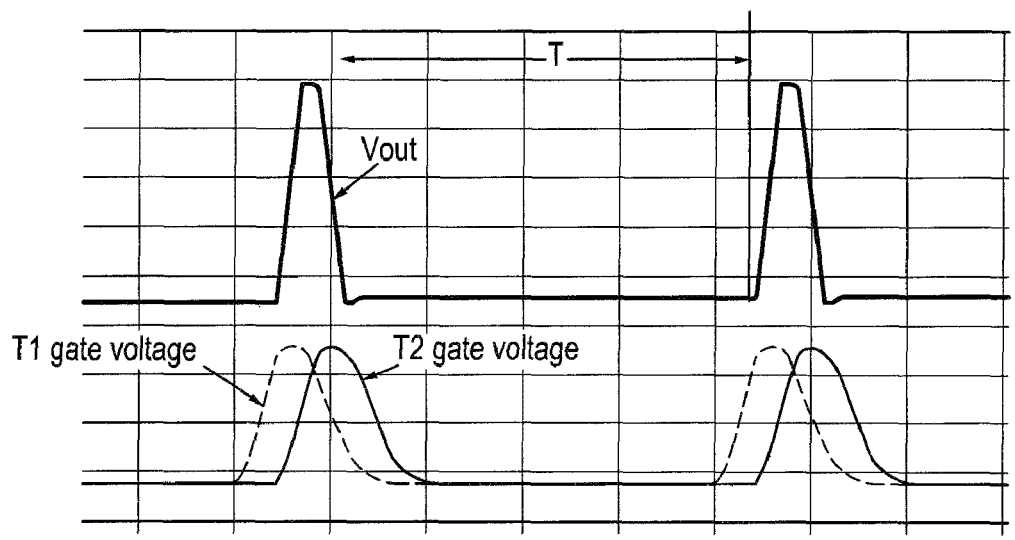
FIG. 4 is a timing diagram depicting two drive signal waveforms.

The pulse width, pulse shape, and/or mutual delay of the two signals V2, V4 may be modulated to arrive at a desired waveform at Vout (also referred to herein as a modified periodic voltage function), and the voltage applied to Vbus may affect the characteristics of the pulses. In other words, the voltage Vbus may affect the pulse width, pulse shape and/or the relative phase of the signals V2, V4. Referring briefly to FIG. 4, for example, shown is a timing diagram depicting two drive signal waveforms that may be applied to T1 and T2 (as V2 and V4) so as to generate the period voltage function at Vout as depicted in FIG. 4. To modulate the shape of the pulses at Vout (e.g. to achieve the smallest time for the pulse at Vout, yet reach a peak value of the pulses) the timing of the two gate drive signals V2, V4 may be controlled.

For example, the two gate drive signals V2, V4 may be applied to the switching components T1, T2 so the time that each of the pulses is applied at Vout may be short compared to the time T between pulses, but long enough to induce a positive voltage at the surface of the substrate 110, 210 to attract electrons to the surface of the substrate 110, 210. Moreover, it has been found that by changing the gate voltage level between the pulses, it is possible to control the slope of the voltage that is applied to Vout between the pulses (e.g., to achieve a substantially constant voltage at the surface of the substrate between pulses). In some modes of operation, the repetition rate of the gate pulses is about 400 kHz, but this rate may certainly vary from application to application.

Although not required, in practice, based upon modeling and refining upon actual implementation, waveforms that may be used to generate the desired (or defined) ion energy distributions may be defined, and the waveforms can be stored (e.g., in the waveform memory portion described with reference to FIG. 1 as a sequence of voltage levels). In addition, in many implementations, the waveforms can be generated directly (e.g., without feedback from Vout); thus avoiding the undesirable aspects of a feedback control system (e.g., settling time).

Figure 5:
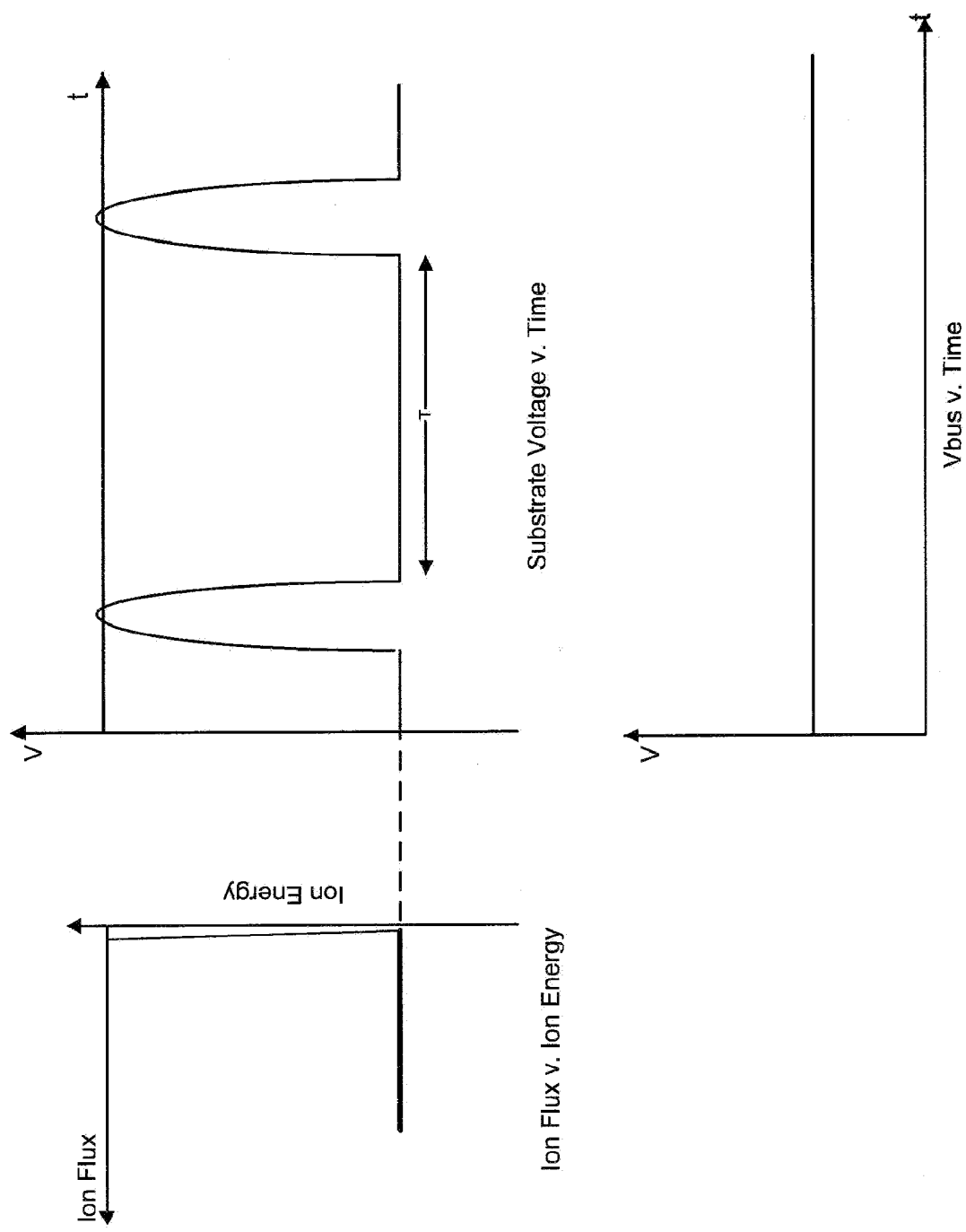
FIG. 5 is a graphical representation of a single mode of operating the switch mode bias supply, which effectuates an ion energy distribution that is concentrated at a particular ion energy.

Referring again to FIG. 3, Vbus can be modulated to control the energy of the ions, and the stored waveforms may be used to control the gate drive signals V2, V4 to achieve a desired pulse amplitude at Vout while minimizing the pulse width. Again, this is done in accordance with the particular characteristics of the transistors, which may be modeled or implemented and empirically established. Referring to FIG. 5, for example, shown are graphs depicting Vbus versus time, voltage at the surface of the substrate 110, 210 versus time, and the corresponding ion energy distribution.

The graphs in FIG. 5 depict a single mode of operating the switch mode bias supply 106, 206, which effectuates an ion energy distribution that is concentrated at a particular ion energy. As depicted, to effectuate the single concentration of ion energies in this example, the voltage applied at Vbus is maintained constant while the voltages applied to V2 and V4 are controlled (e.g., using the drive signals depicted in FIG. 3) so as to generate pulses at the output of the switch-mode bias supply 106, 206, which effectuates the corresponding ion energy distribution shown in FIG. 5.

As depicted in FIG. 5, the potential at the surface of the substrate 110, 210 is generally negative to attract the ions that bombard and etch the surface of the substrate 110, 210. The periodic short pulses that are applied to the substrate 110, 210 (by applying pulses to Vout) have a magnitude defined by the potential that is applied to Vbus, and these pulses cause a brief change in the potential of the substrate 110, 210 (e.g., close to positive or slightly positive potential), which attracts electrons to the surface of the substrate to achieve the generally negative potential along the surface of the substrate 110, 210. As depicted in FIG. 5, the constant voltage applied to Vbus effectuates a single concentration of ion flux at particular ion energy; thus a particular ion bombardment energy may be selected by simply setting Vbus to a particular potential. In other modes of operation, two or more separate concentrations of ion energies may be created (e.g., see FIG. 49).

One of skill in the art will recognize that the power supply need not be limited to a switch-mode power supply, and as such the output of the power supply can also be controlled in order to effect a certain ion energy. As such, the output of the power supply, whether switch-mode or otherwise, when considered without being combined with an ion current compensation or an ion current, can also be referred to as a power supply voltage, $V_{PS}$.

Figure 6:
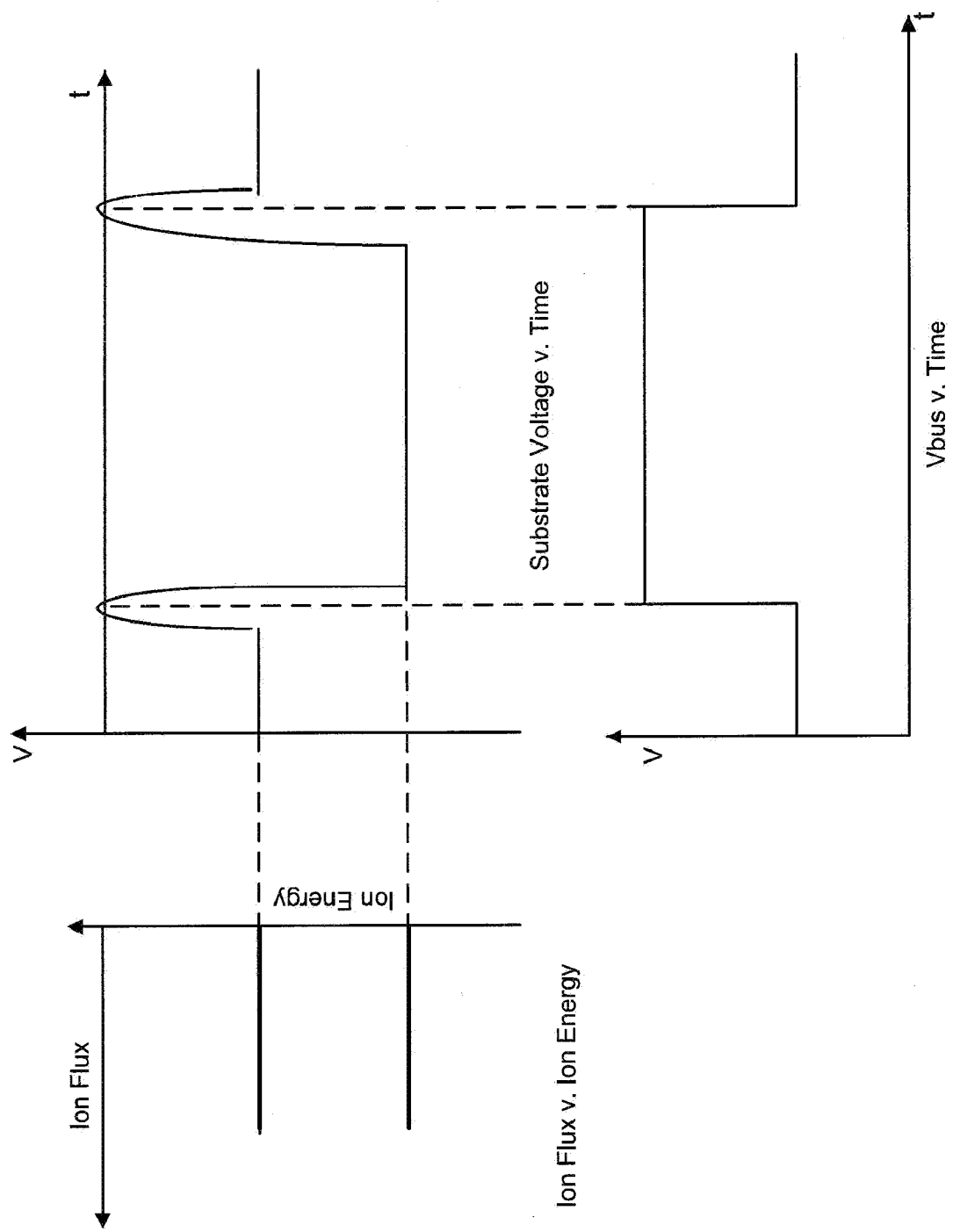
FIG. 6 are graphs depicting a bi-modal mode of operation in which two separate peaks in ion energy distribution are generated.

Referring next to FIG. 6, for example, shown are graphs depicting a bi-modal mode of operation in which two separate peaks in ion energy distribution are generated. As shown, in this mode of operation, the substrate experiences two distinct levels of voltages and periodic pulses, and as a consequence, two separate concentrations of ion energies are created. As depicted, to effectuate the two distinct ion energy concentrations, the voltage that is applied at Vbus alternates between two levels, and each level defines the energy level of the two ion energy concentrations.

Although FIG. 6 depicts the two voltages at the substrate 110, 210 as alternating after every pulse (e.g., FIG. 48), this is certainly not required. In other modes of operation for example, the voltages applied to V2 and V4 are switched (e.g., using the drive signals depicted in FIG. 3) relative to the voltage applied to Vout so that the induced voltage at surface of the substrate alternates from a first voltage to a second voltage (and vice versa) after two or more pulses (e.g., FIG. 49).

In prior art techniques, attempts have been made to apply the combination of two waveforms (generated by waveform generators) to a linear amplifier and apply the amplified combination of the two waveforms to the substrate in order to effectuate multiple ion energies. This approach, however, is much more complex then the approach described with reference to FIG. 6, and requires an expensive linear amplifier, and waveform generators.

Figure 7A:
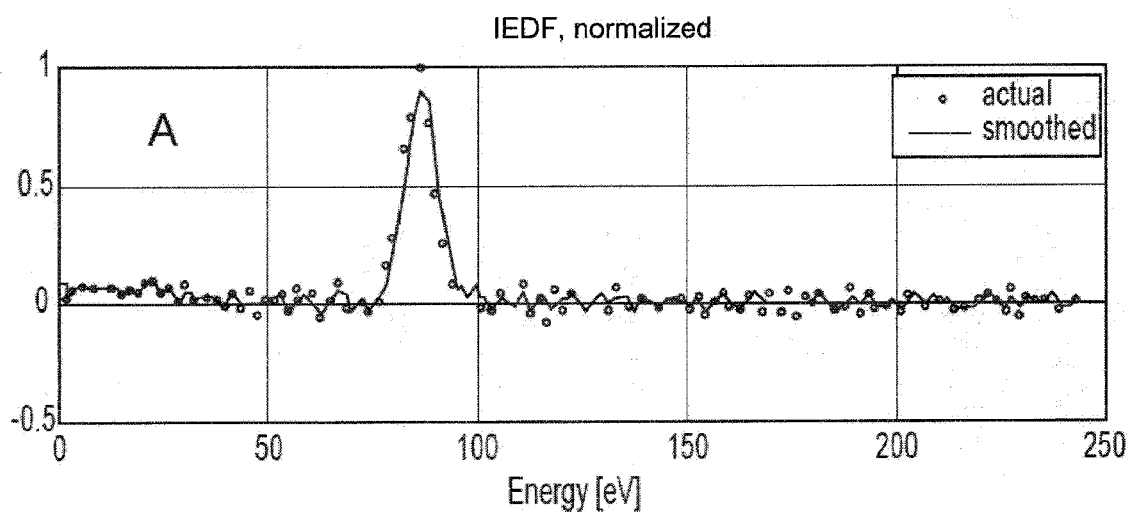
FIGS. 7A and 7B are is are graphs depicting actual, direct ion energy measurements made in a plasma.
Figure 7B:
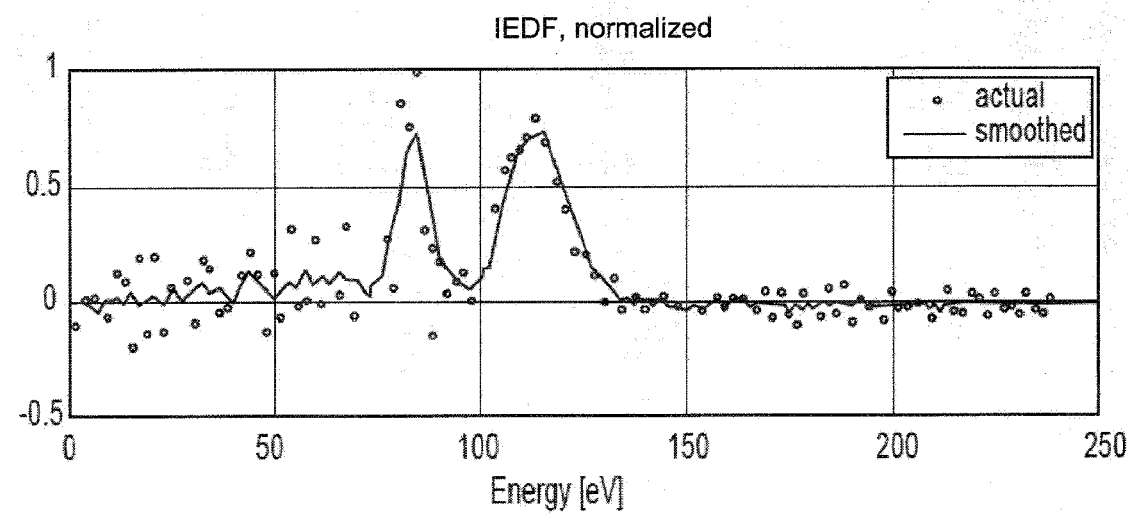

Referring next to FIGS. 7A and 7B, shown are graphs depicting actual, direct ion energy measurements made in a plasma corresponding to monoenergetic and dual-level regulation of the DC voltage applied to Vbus, respectively. As depicted in FIG. 7A, the ion energy distribution is concentrated around 80 eV responsive to a non-varying application of a voltage to Vbus (e.g., as depicted in FIG. 5). And in FIG. 7B, two separate concentrations of ion energies are present at around 85 eV and 115 eV responsive to a dual-level regulation of Vbus (e.g., as depicted in FIG. 6).

Figure 8:
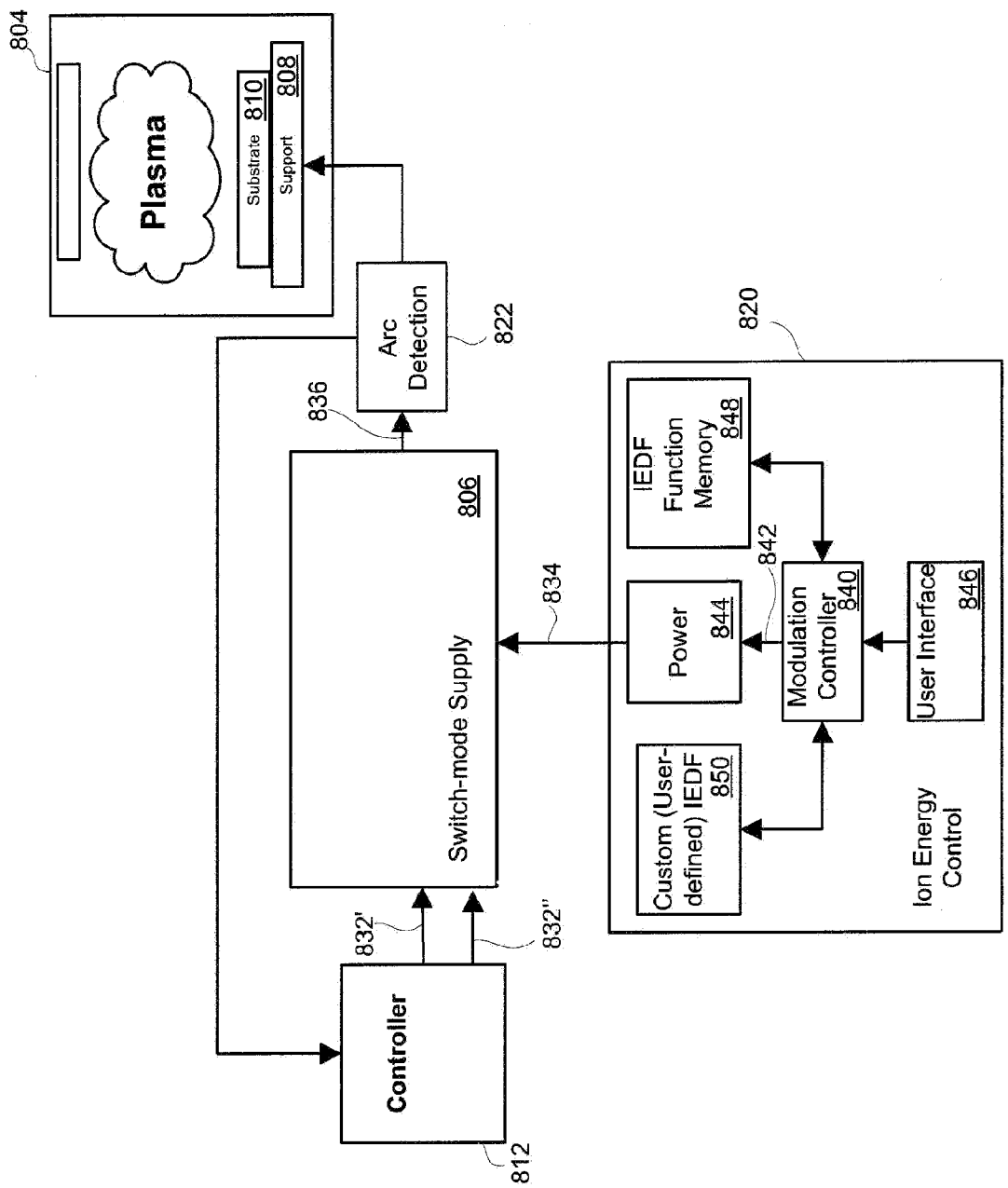
FIG. 8 is a block diagram depicting another embodiment of the present invention.

Referring next to FIG. 8, shown is a block diagram depicting another embodiment of the present invention. As depicted, a switch-mode power supply 806 is coupled to a controller 812, an ion-energy control component 820, and a substrate support 808 via an arc detection component 822. The controller 812, switch-mode supply 806, and ion energy control component 820 collectively operate to apply power to the substrate support 808 so as to effectuate, on a time-averaged basis, a desired (or defined) ion energy distribution at the surface of the substrate 810.

Figure 9A:
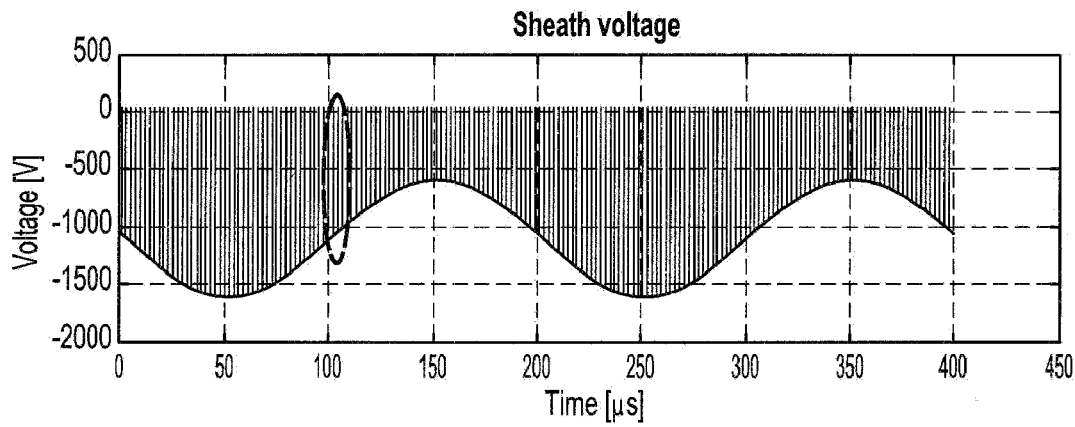
FIG. 9A is a graph depicting an exemplary periodic voltage function that is modulated by a sinusoidal modulating function.
Figure 9B:
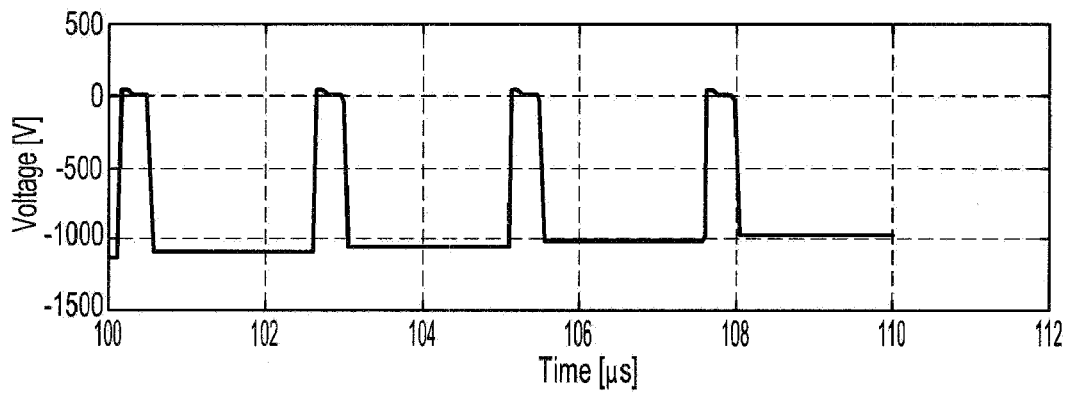
FIG. 9B is an exploded view of a portion of the periodic voltage function that is depicted in FIG. 9A.
Figure 9C:
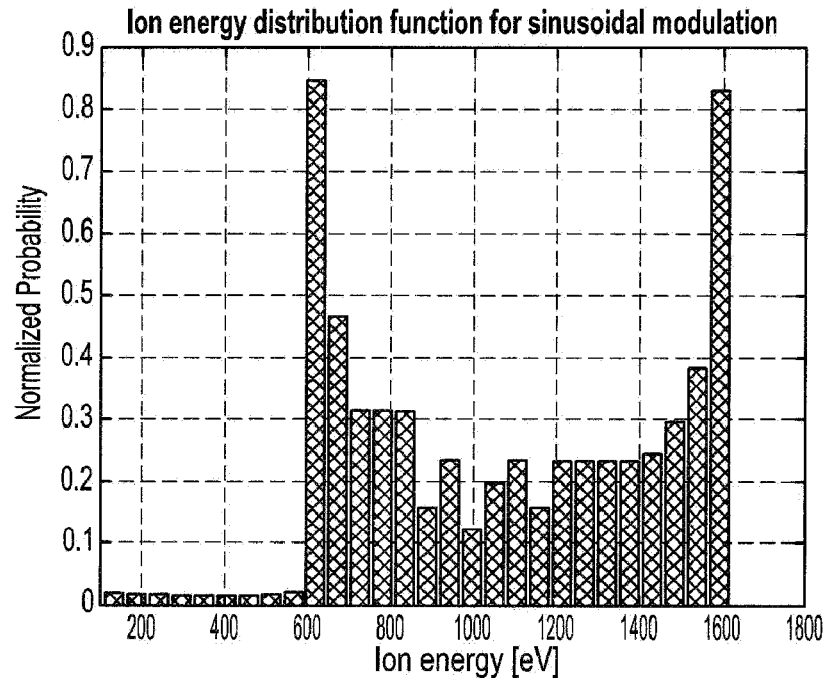
FIG. 9C depicts the resulting distribution of ion energies, on time-averaged basis, that results from the sinusoidal modulation of the periodic voltage function.
Figure 9D:
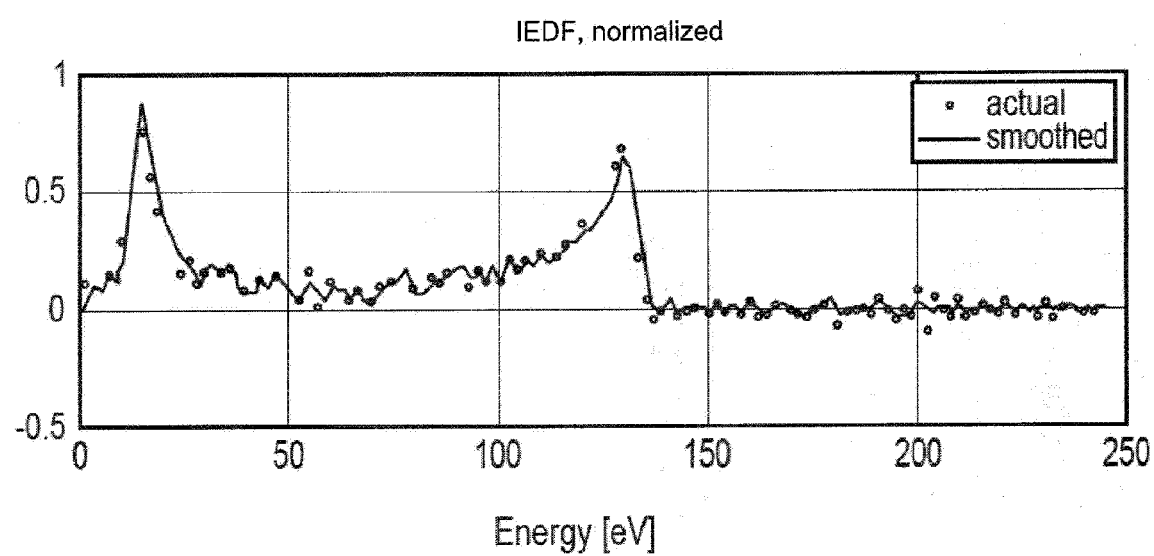
FIG. 9D depicts actual, direct, ion energy measurements made in a plasma of a resultant, time averaged, IEDF when a periodic voltage function is modulated by a sinusoidal modulating function.

Referring briefly to FIG. 9A for example, shown is a periodic voltage function with a frequency of about 400 kHz that is modulated by a sinusoidal modulating function of about 5 kHz over multiple cycles of the periodic voltage function. FIG. 9B is an exploded view of the portion of the periodic voltage function that is circled in FIG. 9A, and FIG. 9C depicts the resulting distribution of ion energies, on a time-averaged basis, that results from the sinusoidal modulation of the periodic voltage function. And FIG. 9D depicts actual, direct, ion energy measurements made in a plasma of a resultant, time-averaged, IEDF when a periodic voltage function is modulated by a sinusoidal modulating function. As discussed further herein, achieving a desired (or defined) ion energy distribution, on a time-averaged basis, may be achieved by simply changing the modulating function that is applied to the periodic voltage.

Figure 10A:
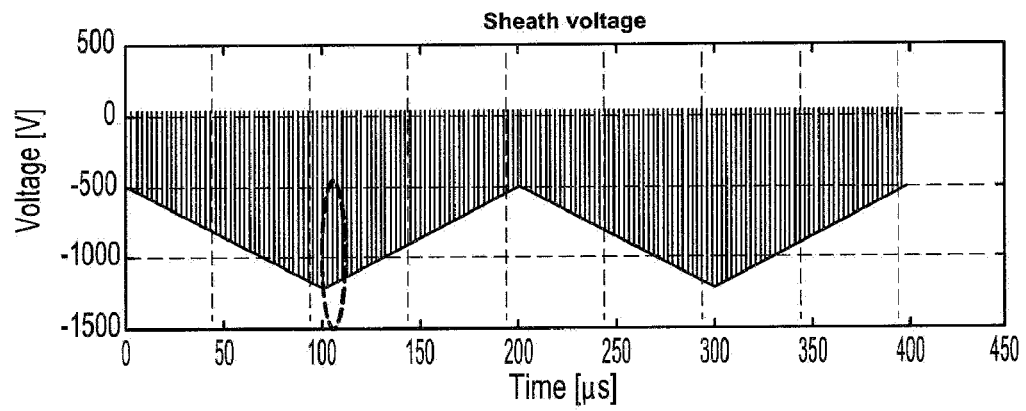
FIG. 10A depicts a periodic voltage function is modulated by a sawtooth modulating function.
Figure 10B:
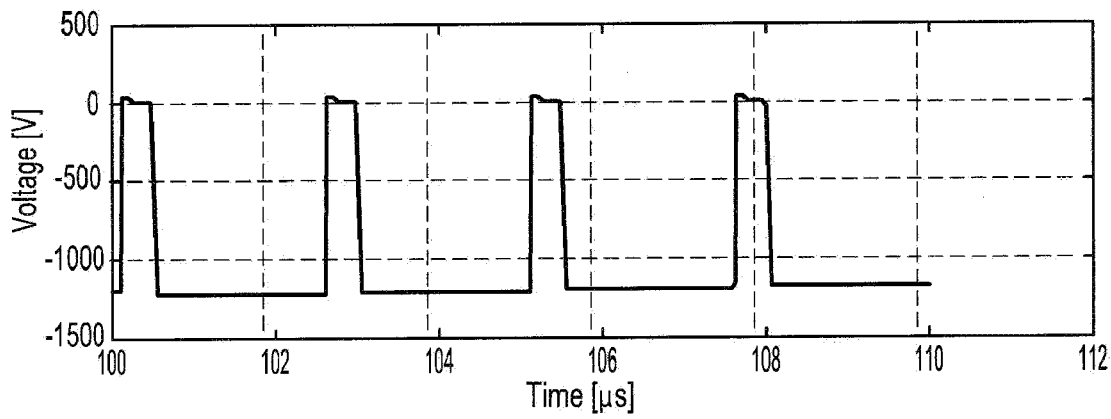
FIG. 10B is an exploded view of a portion of the periodic voltage function that is depicted in FIG. 10A.
Figure 10C:
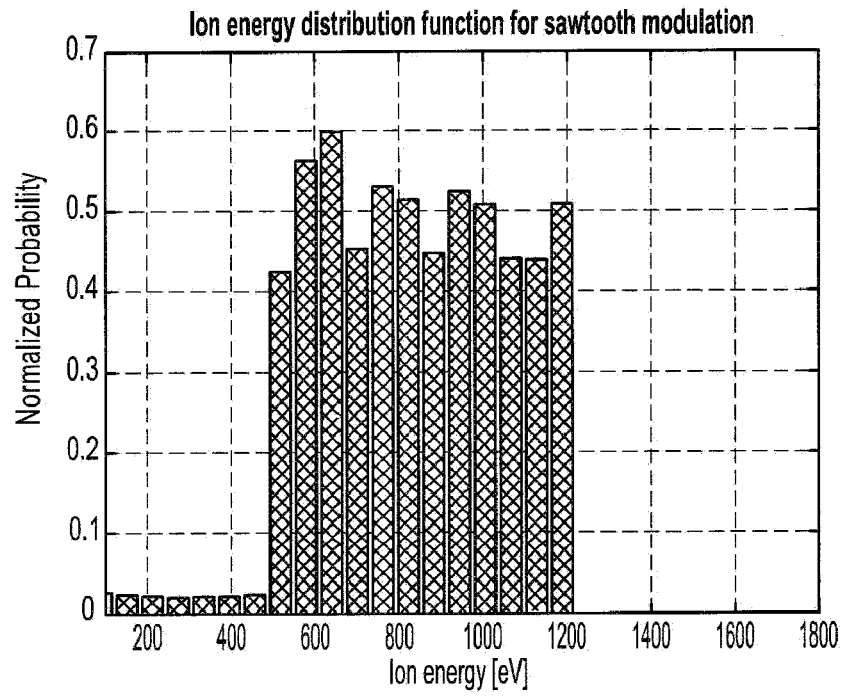
FIG. 10C is a graph depicting the resulting distribution of ion energies, on a time averaged basis, that results from the sinusoidal modulation of the periodic voltage function in FIGS. 10A and 10B.

Referring to FIGS. 10A and 10B as another example, a 400 kHz periodic voltage function is modulated by a sawtooth modulating function of approximately 5 kHz to arrive at the distribution of ion energies depicted in FIG. 10C on a time-averaged basis. As depicted, the periodic voltage function utilized in connection with FIG. 10 is the same as in FIG. 9, except that the periodic voltage function in FIG. 10 is modulated by a sawtooth function instead of a sinusoidal function.

It should be recognized that the ion energy distribution functions depicted in FIGS. 9C and 10C do not represent an instantaneous distribution of ion energies at the surface of the substrate 810, but instead represent the time average of the ion energies. With reference to FIG. 9C, for example, at a particular instant in time, the distribution of ion energies will be a subset of the depicted distribution of ion energies that exist over the course of a full cycle of the modulating function.

It should also be recognized that the modulating function need not be a fixed function nor need it be a fixed frequency. In some instances for example, it may be desirable to modulate the periodic voltage function with one or more cycles of a particular modulating function to effectuate a particular, time-averaged ion energy distribution, and then modulate the periodic voltage function with one or more cycles of another modulating function to effectuate another, time-averaged ion energy distribution. Such changes to the modulating function (which modulates the periodic voltage function) may be beneficial in many instances. For example, if a particular distribution of ion energies is needed to etch a particular geometric construct or to etch through a particular material, a first modulating function may be used, and then another modulating function may subsequently be used to effectuate a different etch geometry or to etch through another material.

Similarly, the periodic voltage function (e.g., the 400 kHz components in FIGS. 9A, 9B, 10A, and 10B and Vout in FIG. 4) need not be rigidly fixed (e.g., the shape and frequency of the periodic voltage function may vary), but generally its frequency is established by the transit time of ions within the chamber so that ions in the chamber are affected by the voltage that is applied to the substrate 810.

Referring back to FIG. 8, the controller 812 provides drive-control signals 832', 832" to the switch-mode supply 806 so that the switch-mode supply 806 generates a periodic voltage function. The switch mode supply 806 may be realized by the components depicted in FIG. 3 (e.g., to create a periodic voltage function depicted in FIG. 4), but it is certainly contemplated that other switching architectures may be utilized.

In general, the ion energy control component 820 functions to apply a modulating function to the periodic voltage function (that is generated by the controller 812 in connection with the switch mode power supply 806). As shown in FIG. 8, the ion energy control component 820 includes a modulation controller 840 that is in communication with a custom IEDF portion 850, an IEDF function memory 848, a user interface 846, and a power component 844. It should be recognized that the depiction of these components is intended to convey functional components, which in reality, may be effectuated by common or disparate components.

The modulation controller 840 in this embodiment generally controls the power component 844 (and hence its output 834) based upon data that defines a modulation function, and the power component 844 generates the modulation function 834 (based upon a control signal 842 from the modulation controller 840) that is applied to the periodic voltage function that is generated by the switch-mode supply 806. The user interface 846 in this embodiment is configured to enable a user to select a predefined IEDF function that is stored in the IEDF function memory 848, or in connection with the custom IEDF component 850, define a custom IEDF In many implementations, the power component 844 includes a DC power supply (e.g., a DC switch mode power supply or a linear amplifier), which applies the modulating function (e.g. a varying DC voltage) to the switch mode power supply (e.g., to Vbus of the switch mode power supply depicted in FIG. 3). In these implementations, the modulation controller 840 controls the voltage level that is output by the power component 844 so that the power component 844 applies a voltage that conforms to the modulating function.

Figure 11:
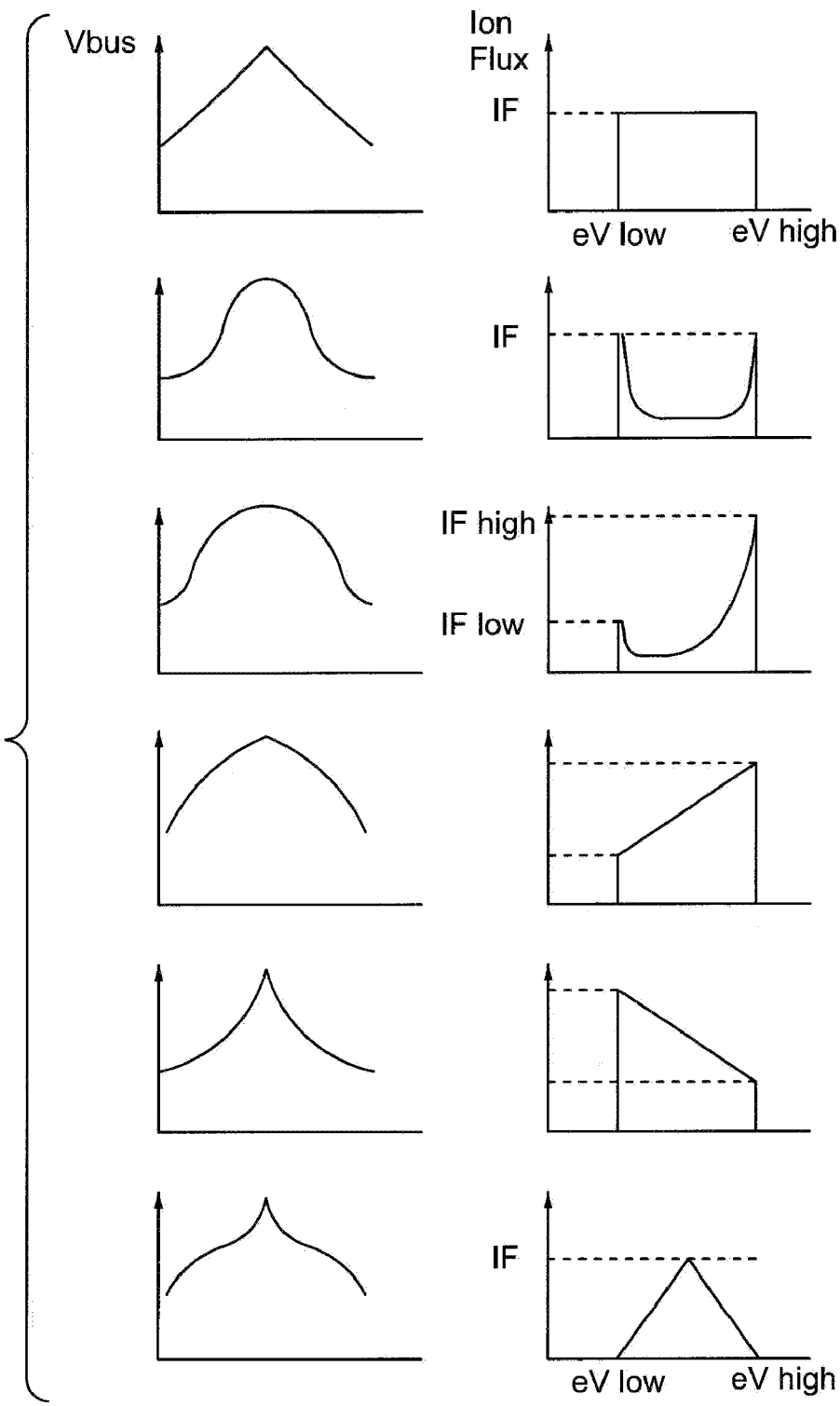
FIG. 11 are graphs showing IEDF functions in the right column and associated modulating functions in the left column.

In some implementations, the IEDF function memory 848 includes a plurality of data sets that correspond to each of a plurality of IEDF distribution functions, and the user interface 846 enables a user to select a desired (or defined) IEDF function. Referring to FIG. 11 for example, shown in the right column are exemplary IEDF functions that may be available for a user to select. And the left column depicts the associated modulating function that the modulation controller 840 in connection with the power component 844 would apply to the periodic voltage function to effectuate the corresponding IEDF function. It should be recognized that the IEDF functions depicted in FIG. 11 are only exemplary and that other IEDF functions may be available for selection.

The custom IEDF component 850 generally functions to enable a user, via the user interface 846, to define a desired (or defined) ion energy distribution function. In some implementations for example, the custom IEDF component 850 enables a user to establish values for particular parameters that define a distribution of ion energies.

For example, the custom IEDF component 850 may enable IEDF functions to be defined in terms of a relative level of flux (e.g., in terms of a percentage of flux) at a high-level (IF-high), a mid-level (IF-mid), and a low level (IF-low) in connection with a function(s) that defines the IEDF between these energy levels. In many instances, only IF-high, IF-low, and the IEDF function between these levels is sufficient to define an IEDF function. As a specific example, a user may request 1200 eV at a 20% contribution level (contribution to the overall IEDF), 700 eV at a 30% contribution level with a sinusoid IEDF between these two levels.

It is also contemplated that the custom IEDF portion 850 may enable a user to populate a table with a listing of one or more (e.g., multiple) energy levels and the corresponding percentage contribution of each energy level to the IEDF. And in yet alternative embodiments, it is contemplated that the custom IEDF component 850 in connection with the user interface 846 enables a user to graphically generate a desired (or defined) IEDF by presenting the user with a graphical tool that enables a user to draw a desired (or defined) IEDF.

In addition, it is also contemplated that the IEDF function memory 848 and the custom IEDF component 850 may interoperate to enable a user to select a predefined IEDF function and then alter the predefined IEDF function so as to produce a custom IEDF function that is derived from the predefined IEDF function.

Once an IEDF function is defined, the modulation controller 840 translates data that defines the desired (or defined) IEDF function into a control signal 842, which controls the power component 844 so that the power component 844 effectuates the modulation function that corresponds to the desired (or defined) IEDF. For example, the control signal 842 controls the power component 844 so that the power component 844 outputs a voltage that is defined by the modulating function.

Figure 12:
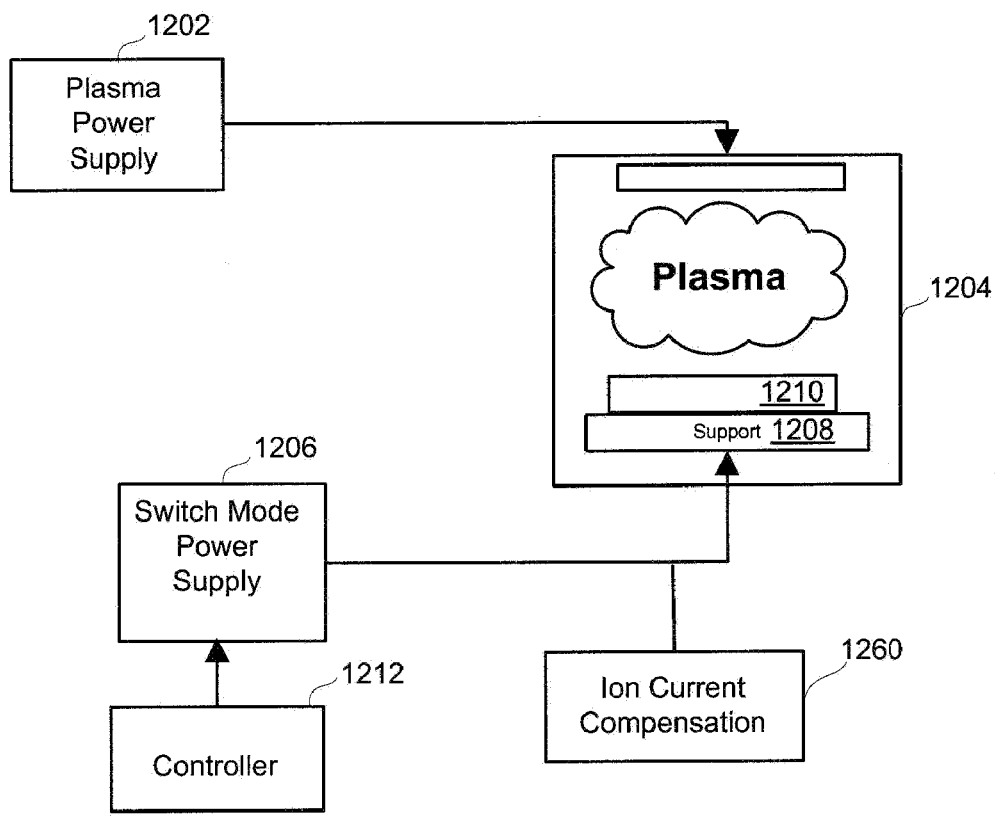
FIG. 12 is a block diagram depicting an embodiment in which an ion current compensation component compensates for ion current in a plasma chamber.
Figure 15A:
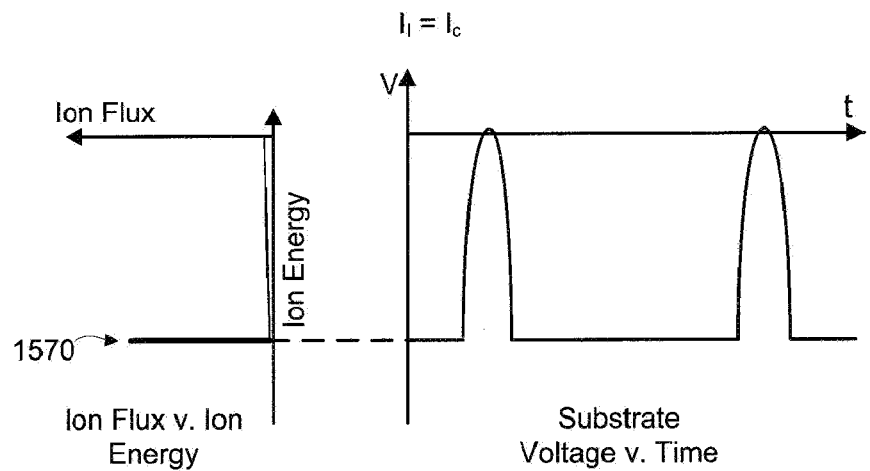
FIGS. 15A-15C are voltage waveforms as appearing at the surface of the substrate or wafer responsive to compensation current.
Figure 15B:
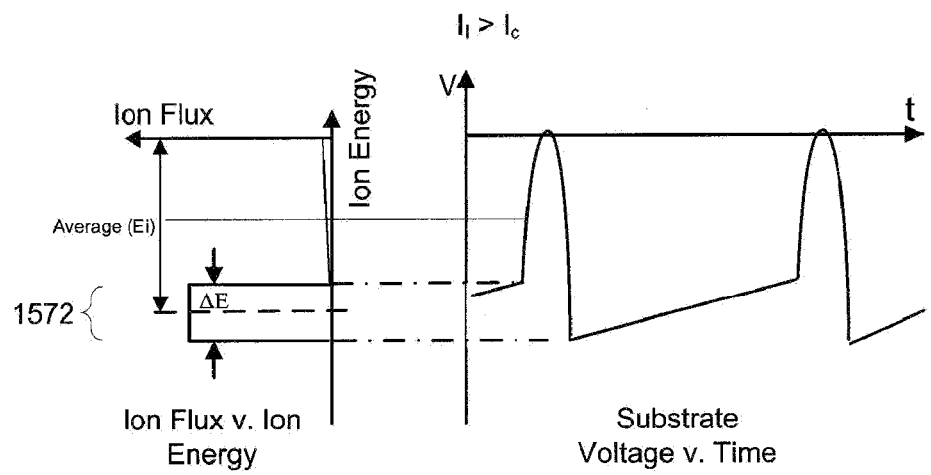
Figure 15C:
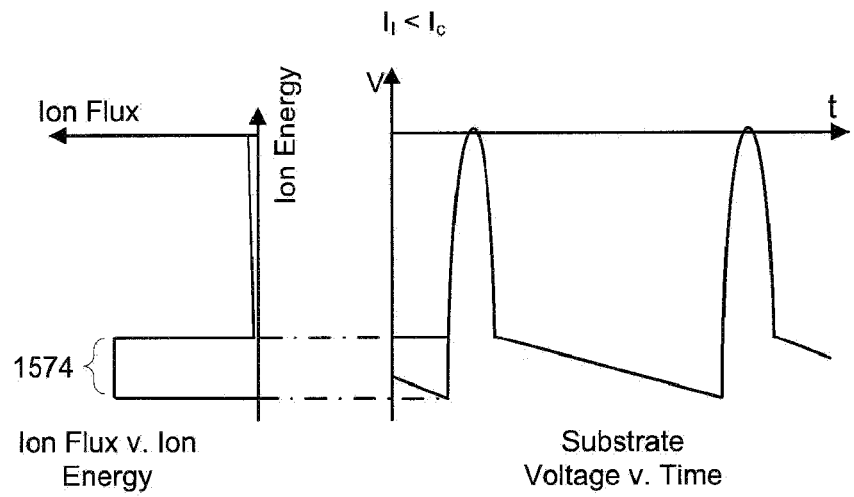

Referring next to FIG. 12, it is a block diagram depicting an embodiment in which an ion current compensation component 1260 compensates for ion current in the plasma chamber 1204. Applicants have found that, at higher energy levels, higher levels of ion current within the chamber affect the voltage at the surface of the substrate, and as a consequence, the ion energy distribution is also affected. Referring briefly to FIGS. 15A-15C for example, shown are voltage waveforms as they appear at the surface of the substrate 1210 or wafer and their relationship to IEDF.

More specifically, FIG. 15A depicts a periodic voltage function at the surface of the substrate 1210 when ion current $I_I$ is equal to compensation current Ic; FIG. 15B depicts the voltage waveform at the surface of the substrate 1210 when ion current $I_I$ is greater than the compensation current Ic; and FIG. 15C depicts the voltage waveform at the surface of the substrate when ion current is less than the compensation current Ic.

As depicted in FIG. 15A, when $I_I$=Ic a spread of ion energies 1470 is relatively narrow as compared to a uniform spread 1472 of ion energies when $I_I$>Ic as depicted in FIG. 15B or a uniform spread 1474 of ion energies when $I_I$<Ic as depicted in FIG. 15C. Thus, the ion current compensation component 1260 enables a narrow spread of ion energies when the ion current is high (e.g., by compensating for effects of ion current), and it also enables a width of the spread 1572, 1574 of uniform ion energy to be controlled (e.g., when it is desirable to have a spread of ion energies).

As depicted in FIG. 15B, without ion current compensation (when $I_I$>Ic) the voltage at the surface of the substrate, between the positive portions of the periodic voltage function, becomes less negative in a ramp-like manner, which produces a broader spread 1572 of ion energies. Similarly, when ion current compensation is utilized to increase a level of compensation current to a level that exceeds the ion current ($I_I$<Ic) as depicted in FIG. 15C, the voltage at the surface of the substrate becomes more negative in a ramp-like manner between the positive portions of the periodic voltage function, and a broader spread 1574 of uniform ion energies is produced.

Figure 13:
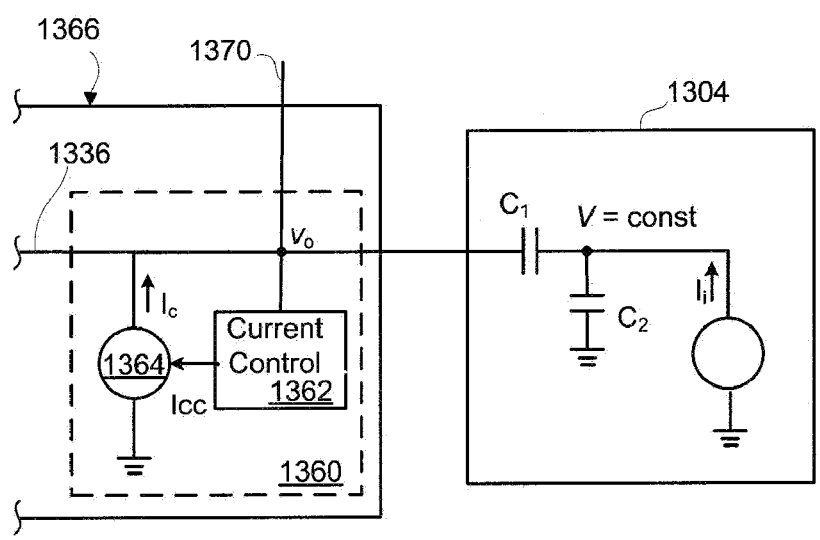
FIG. 13 is a diagram depicting an exemplary ion current compensation component.

Referring back to FIG. 12, the ion current compensation component 1260 may be realized as a separate accessory that may optionally be added to the switch mode power supply 1206 and controller 1212. In other embodiments, (e.g., as depicted in FIG. 13) the ion current compensation component 1260 may share a common housing 1366 with other components described herein (e.g., the switch-mode power supply 106, 206, 806, 1206 and ion energy control 220, 820 components). In this embodiment, the periodic voltage function provided to the plasma chamber 1204 can be referred to as a modified periodic voltage function since it comprises the periodic voltage function modified by the ion current compensation from ion current compensation component 1260. The controller 1212 can sample a voltage at different times at an electrical node where outputs of the switch mode power supply 1206 and the ion current compensation 1260 combine.

As depicted in FIG. 13, shown is an exemplary ion current compensation component 1360 that includes a current source 1364 coupled to an output 1336 of a switch mode supply and a current controller 1362 that is coupled to both the current source 1364 and the output 1336. Also depicted in FIG. 13 is a plasma chamber 1304, and within the plasma chamber are capacitive elements $C_1$, $C_2$, and ion current $I_I$. As depicted, $C_1$ represents the inherent capacitance (also referred to herein as effective capacitance) of components associated with the chamber 1304, which may include, but is not limited to, insulation, the substrate, substrate support, and an e-chuck, and $C_2$ represents sheath capacitance and stray capacitances. In this embodiment, the periodic voltage function provided to the plasma chamber 1304, and measurable at $V_O$, can be referred to as a modified periodic voltage function since it comprises the periodic voltage function modified by the ion current compensation, Ic.

The sheath (also herein referred to as a plasma sheath) is a layer in a plasma near the substrate surface and possibly walls of the plasma processing chamber with a high density of positive ions and thus an overall excess of positive charge. The surface with which the sheath is in contact with typically has a preponderance of negative charge. The sheath arises by virtue of the faster velocity of electrons than positive ions thus causing a greater proportion of electrons to reach the substrate surface or walls, thus leaving the sheath depleted of electrons. The sheath thickness, $\lambda_{sheath}$, is a function of plasma characteristics such as plasma density and plasma temperature.

It should be noted that because $C_1$ in this embodiment is an inherent (also referred to herein as effective) capacitance of components associated with the chamber 1304, it is not an accessible capacitance that is added to gain control of processing. For example, some prior art approaches that utilize a linear amplifier couple bias power to the substrate with a blocking capacitor, and then utilize a monitored voltage across the blocking capacitor as feedback to control their linear amplifier. Although a capacitor could couple a switch mode power supply to a substrate support in many of the embodiments disclosed herein, it is unnecessary to do so because feedback control using a blocking capacitor is not required in several embodiments of the present invention.

Figure 14:
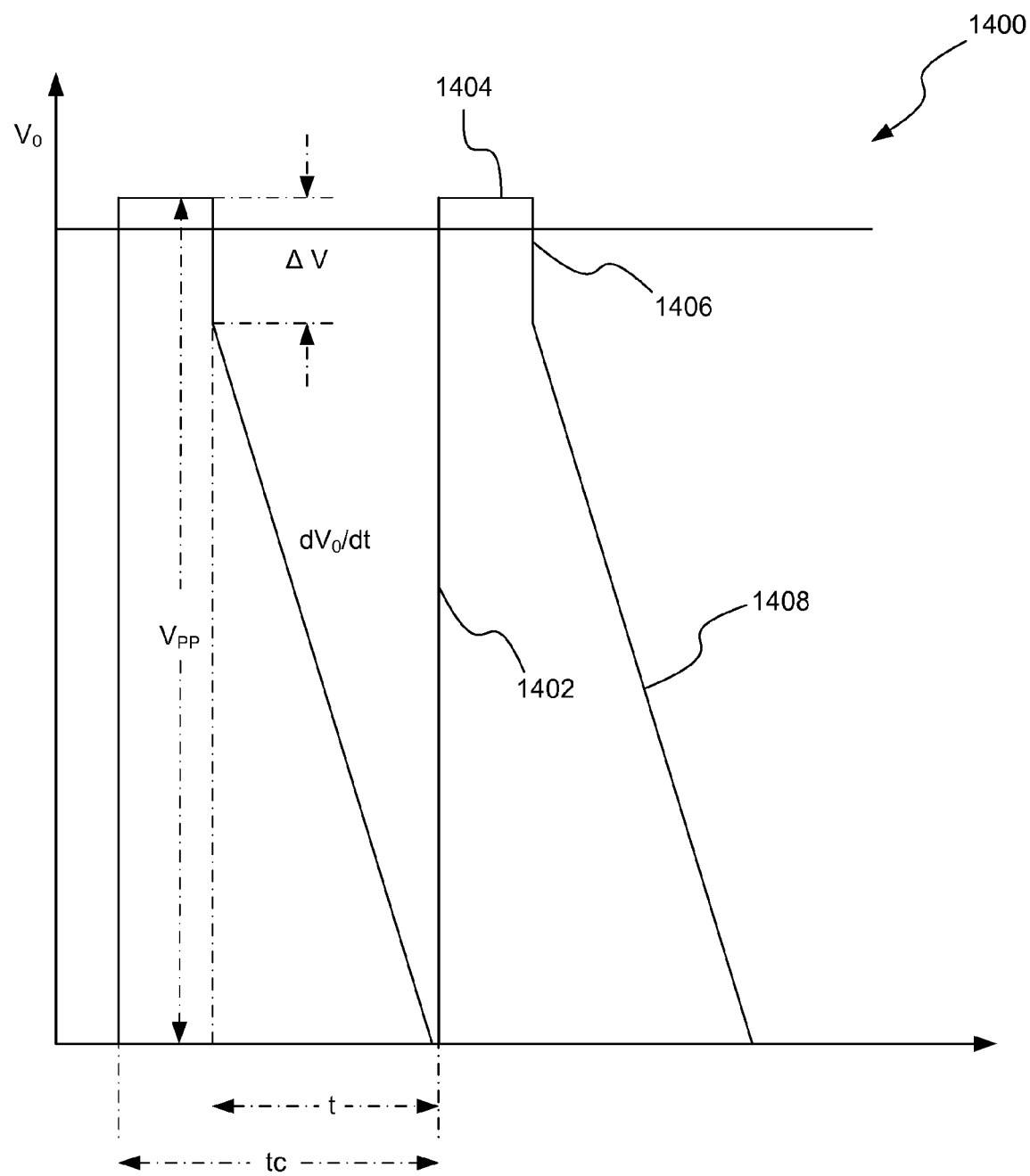
FIG. 14 is a graph depicting an exemplary voltage at node Vo depicted in FIG. 13.

While referring to FIG. 13, simultaneous reference is made to FIG. 14, which is a graph depicting an exemplary voltage (e.g., the modified periodic voltage function) at Vo depicted in FIG. 13. In operation, the current controller 1362 monitors the voltage at Vo, and ion current is calculated over an interval t (depicted in FIG. 14) as:

$$I_I = C_1 \frac{dVo}{dt} \quad \text{(Equation 1)}$$

Ion current, $I_I$, and inherent capacitance (also referred to as effective capacitance), $C_1$, can either or both be time varying. Because $C_1$ is substantially constant for a given tool and is measurable, only Vo needs to be monitored to enable ongoing control of compensation current. As discussed above, to obtain a more mono-energetic distribution of ion energy (e.g., as depicted in FIG. 15A) the current controller controls the current source 1364 so that Ic is substantially the same as $I_I$ (or in the alternative, related according to Equation 2). In this way, a narrow spread of ion energies may be maintained even when the ion current reaches a level that affects the voltage at the surface of the substrate. And in addition, if desired, the spread of the ion energy may be controlled as depicted in FIGS. 15B and 15C so that additional ion energies are realized at the surface of the substrate.

Also depicted in FIG. 13 is a feedback line 1370, which may be utilized in connection with controlling an ion energy distribution. For example, the value of ΔV (also referred to herein as a voltage step or the third portion 1406) depicted in FIG. 14, is indicative of instantaneous ion energy and may be used in many embodiments as part of a feedback control loop. In one embodiment, the voltage step, ΔV, is related to ion energy according to Equation 4. In other embodiments, the peak-to-peak voltage, $V_{PP}$ can be related to the instantaneous ion energy. Alternatively, the difference between the peak-to-peak voltage, $V_{PP}$, and the product of the slope, $dV_0/dt$, of the fourth portion 1408 times time, t, can be correlated to the instantaneous ion energy (e.g., $V_{PP}-dV_0/dt \cdot t$).

Figure 16:
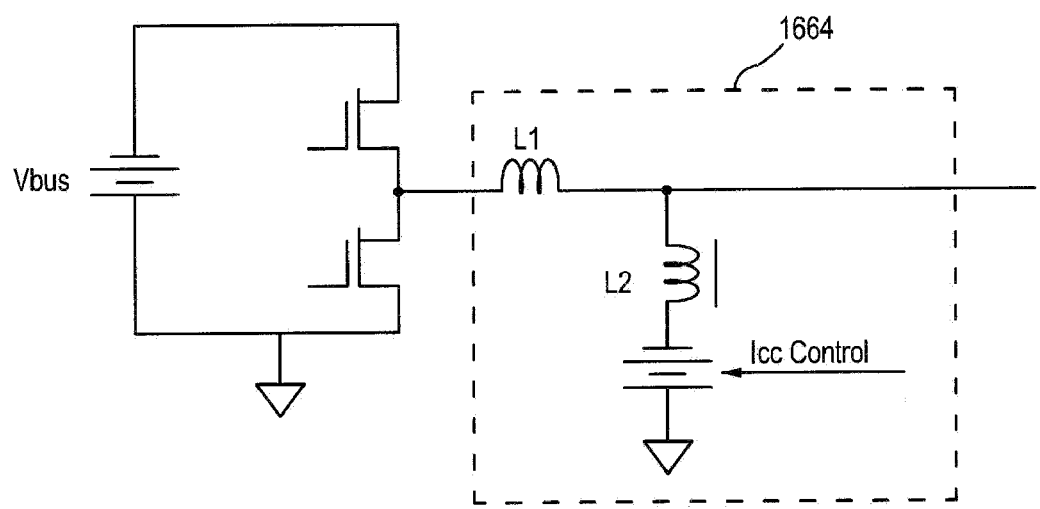
FIG. 16 is an exemplary embodiment of a current source, which may be implemented to realize the current source described with reference to FIG. 13.

Referring next to FIG. 16, shown is an exemplary embodiment of a current source 1664, which may be implemented to realize the current source 1364 described with reference to FIG. 13. In this embodiment, a controllable negative DC voltage source, in connection with a series inductor L2, function as a current source, but one of ordinary skill in the art will appreciate, in light of this specification, that a current source may be realized by other components and/or configurations.

Figure 43:
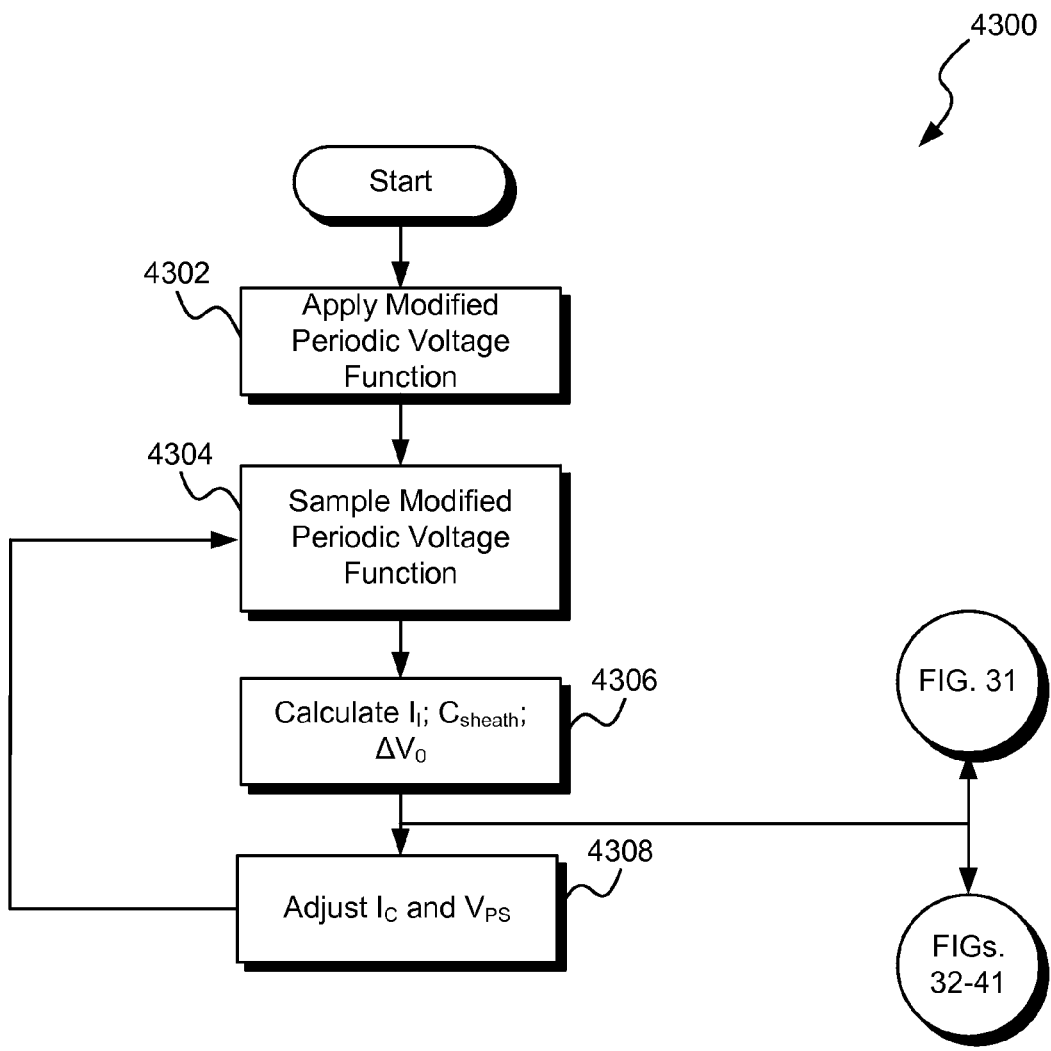
FIG. 43 illustrates one embodiment of a method of controlling an ion energy distribution of ions impacting a surface of a substrate.

FIG. 43 illustrates one embodiment of a method of controlling an ion energy distribution of ions impacting a surface of a substrate. The method 4300 starts by applying a modified periodic voltage function 4302 (see the modified periodic voltage function 4402 in FIG. 44) to a substrate support supporting a substrate within a plasma processing chamber. The modified periodic voltage function can be controlled via at least two 'knobs' such as an ion current compensation, $I_C$, (see $I_C$ 4404 in FIG. 44) and a power supply voltage, $V_{PS}$, (see power supply voltage 4406 in FIG. 44). An exemplary component for generating the power supply voltage is the switch mode power supply 106 in FIG. 1. In order to help explain the power supply voltage, $V_{PS}$, it is illustrated herein as if measured without coupling to the ion current and ion current compensation. The modified periodic voltage function is then sampled at a first and second value of an ion current compensation, $I_C$, 4304. At least two samples of a voltage of the modified periodic voltage function are taken for each value of the ion current compensation, $I_C$. The sampling 4304 is performed in order to enable calculations 4306 (or determinations) of the ion current, $I_I$, and a sheath capacitance, $C_{sheath}$, 4306. Such determination may involve finding an ion current compensation, $I_C$, that if applied to the substrate support (or as applied to the substrate support) would generate a narrow (e.g., minimum) ion energy distribution function (IEDF) width. The calculations 4306 can also optionally include determining a voltage step, ΔV, (also known as a third portion of the modified periodic voltage function 1406) based on the sampling 4304 of the waveform of the modified periodic voltage function. The voltage step, ΔV, can be related to the ion energy of ions reaching the substrate's surface. When finding the ion current, $I_I$, for the first time, the voltage step, ΔV, can be ignored. Details of the sampling 4304 and the calculations 4306 will be provided in discussions of FIG. 30 to follow.

Figure 31:
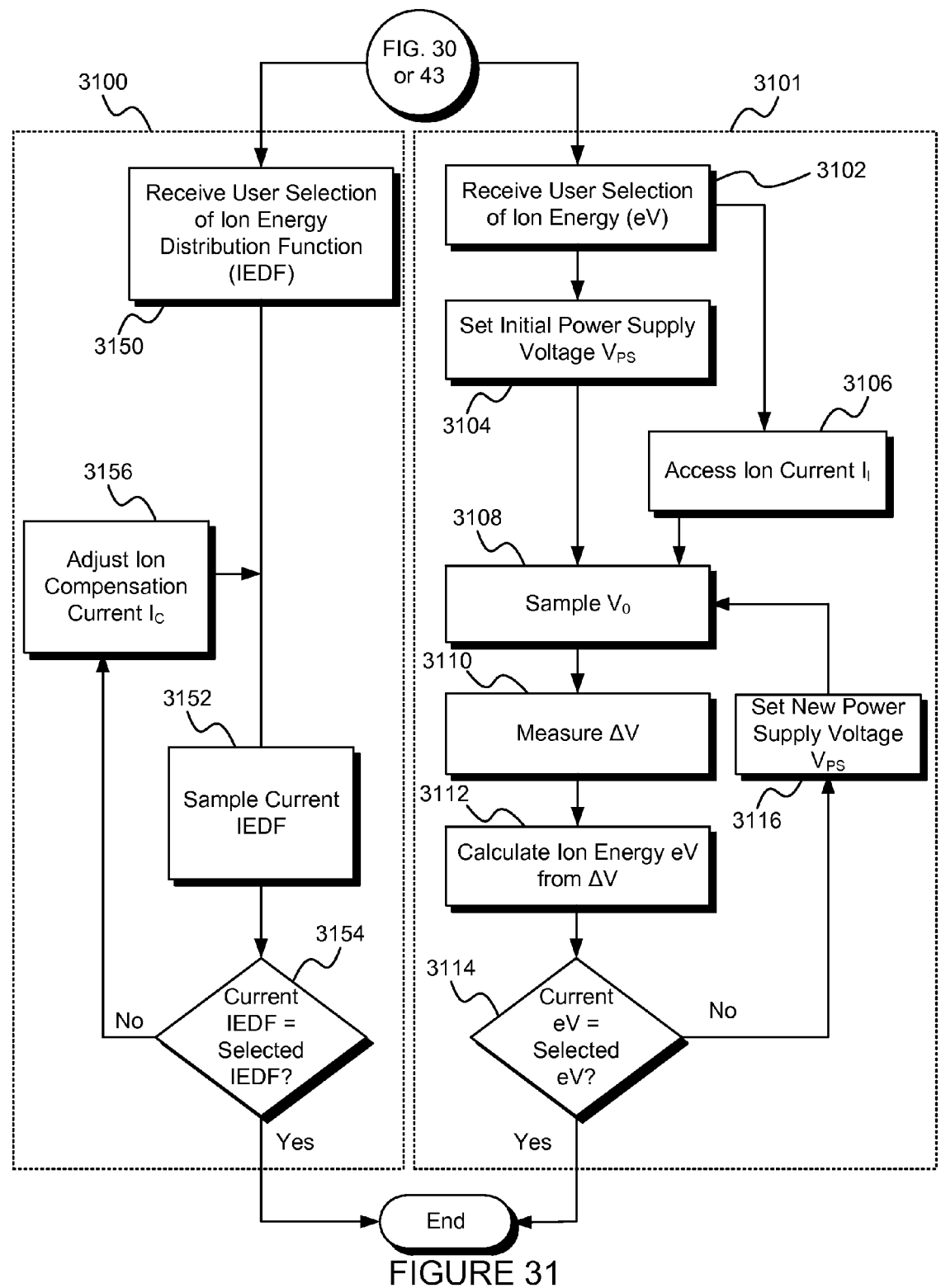
FIG. 31 illustrates methods for setting the IEDF and the ion energy.
Figure 46:
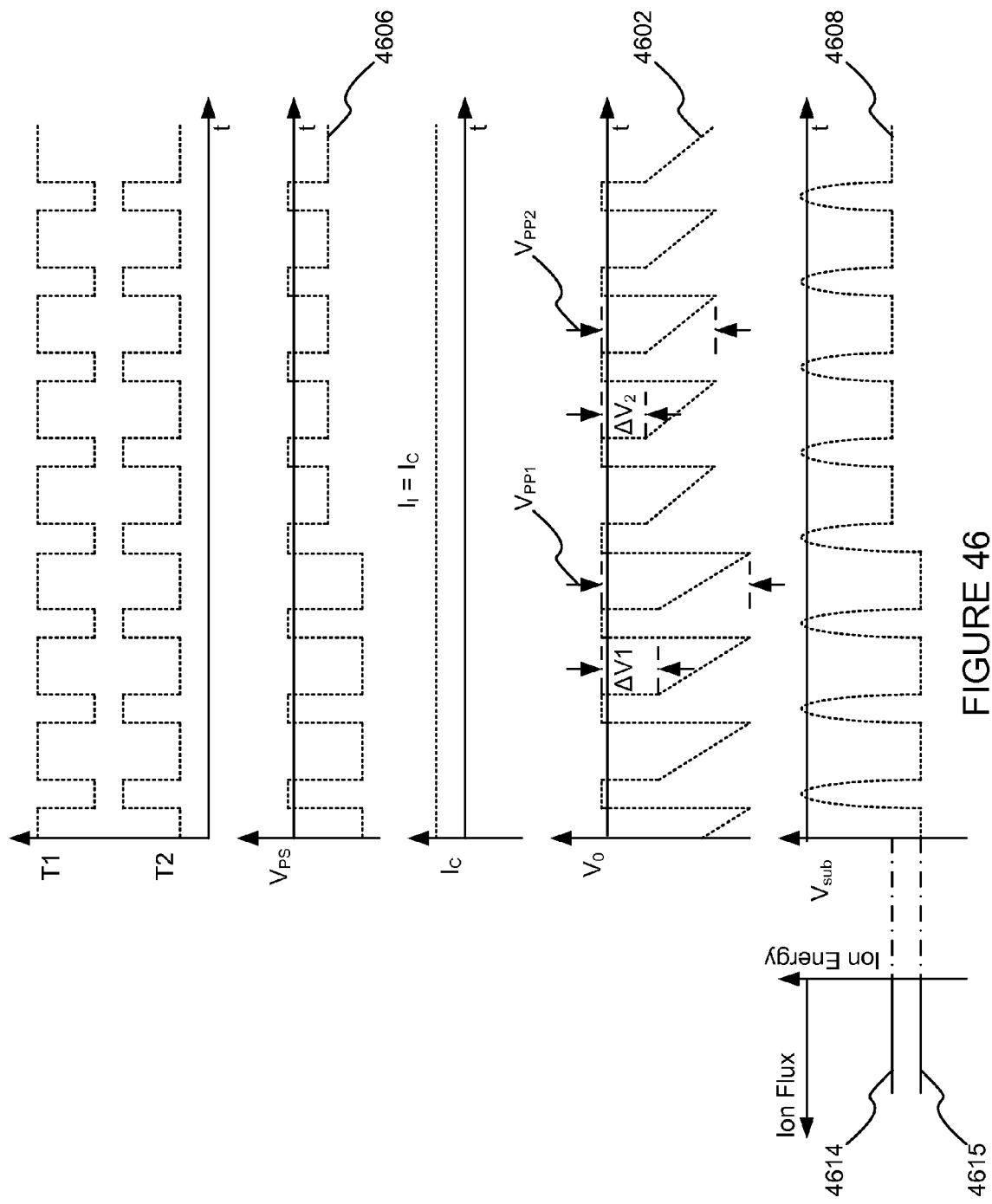
FIG. 46 illustrates selection of ion energy.
Figure 47:
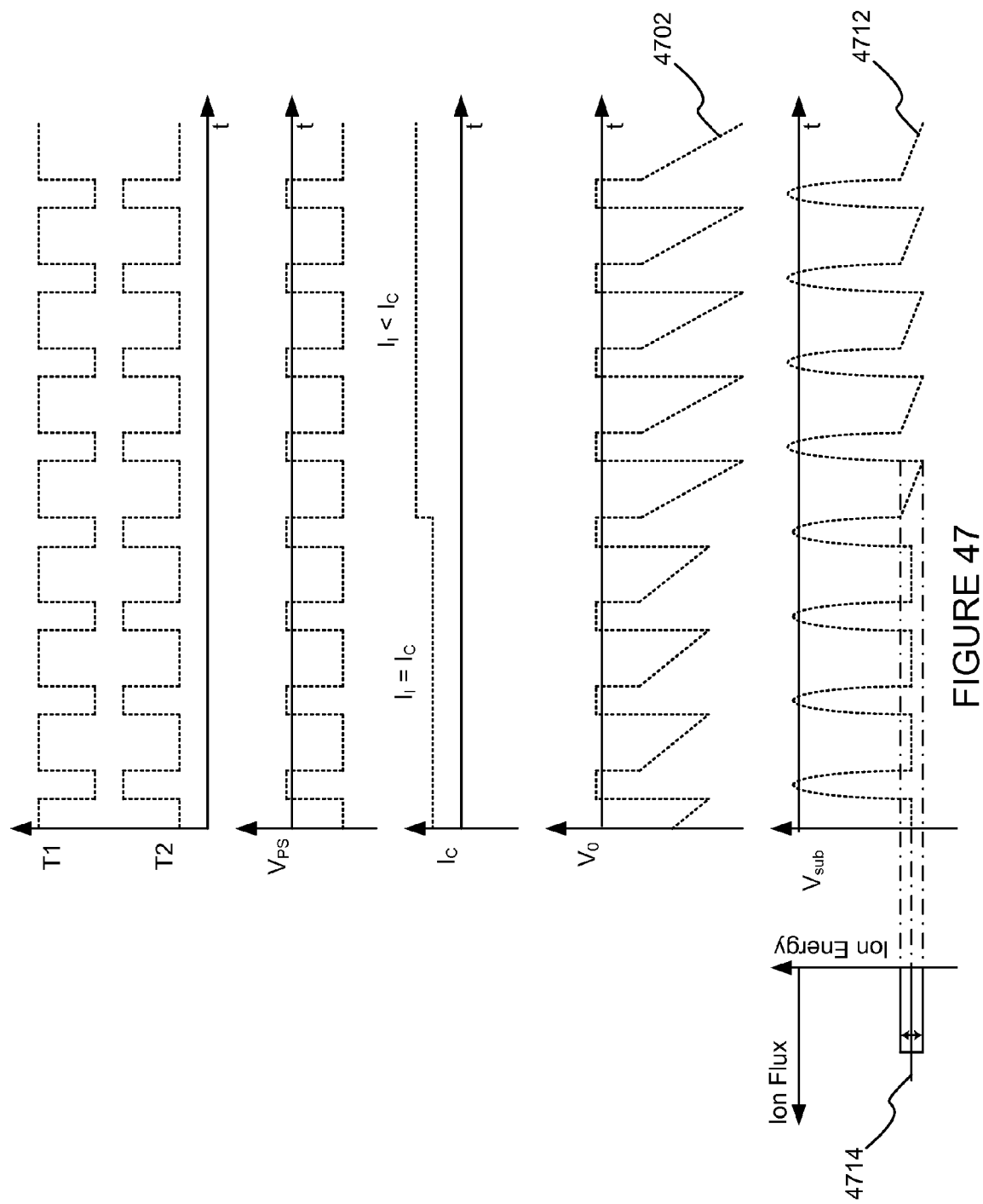
FIG. 47 illustrates selection and expansion of the ion energy distribution function width.

Once the ion current, $I_I$, and sheath capacitance, $C_{sheath}$, are known, the method 4300 may move to the method 3100 of FIG. 31 involving setting and monitoring an ion energy and a shape (e.g., width) of the IEDF. For instance, FIG. 46 illustrates how a change in the power supply voltage can effect a change in the ion energy. In particular, a magnitude of the illustrated power supply voltage is decreased resulting in a decreased magnitude of the ion energy. Additionally, FIG. 47 illustrates that given a narrow IEDF 4714, the IEDF can be widened by adjusting the ion current compensation, $I_C$. Alternatively or in parallel, the method 4300 can perform various metrics as described with reference to FIGS. 32-41 that make use of the ion current, $I_I$, the sheath capacitance, $C_{sheath}$, and other aspects of the waveform of the modified periodic voltage function.

In addition to setting the ion energy and/or the IEDF width, the method 4300 may adjust the modified periodic voltage function 4308 in order to maintain the ion energy and the IEDF width. In particular, adjustment of the ion current compensation, $I_C$, provided by an ion current compensation component, and adjustment of the power supply voltage may be performed 4308. In some embodiments, the power supply voltage can be controlled by a bus voltage, $V_{bus}$, of the power supply (e.g., the bus voltage $V_{bus}$ of FIG. 3). The ion current compensation, $I_C$, controls the IEDF width, and the power supply voltage controls the ion energy.

After these adjustments 4308, the modified periodic voltage function can again be sampled 4304 and calculations of ion current, $I_I$, sheath capacitance, $C_{sheath}$, and the voltage step, ΔV, can again be performed 4306. If the ion current, $I_I$, or the voltage step, ΔV, are other than defined values (or in the alternative, desired values), then the ion current compensation, $I_C$, and/or the power supply voltage can be adjusted 4308. Looping of the sampling 4304, calculating, 4306, and adjusting 4308 may occur in order to maintain the ion energy, eV, and/or the IEDF width.

Figure 30:
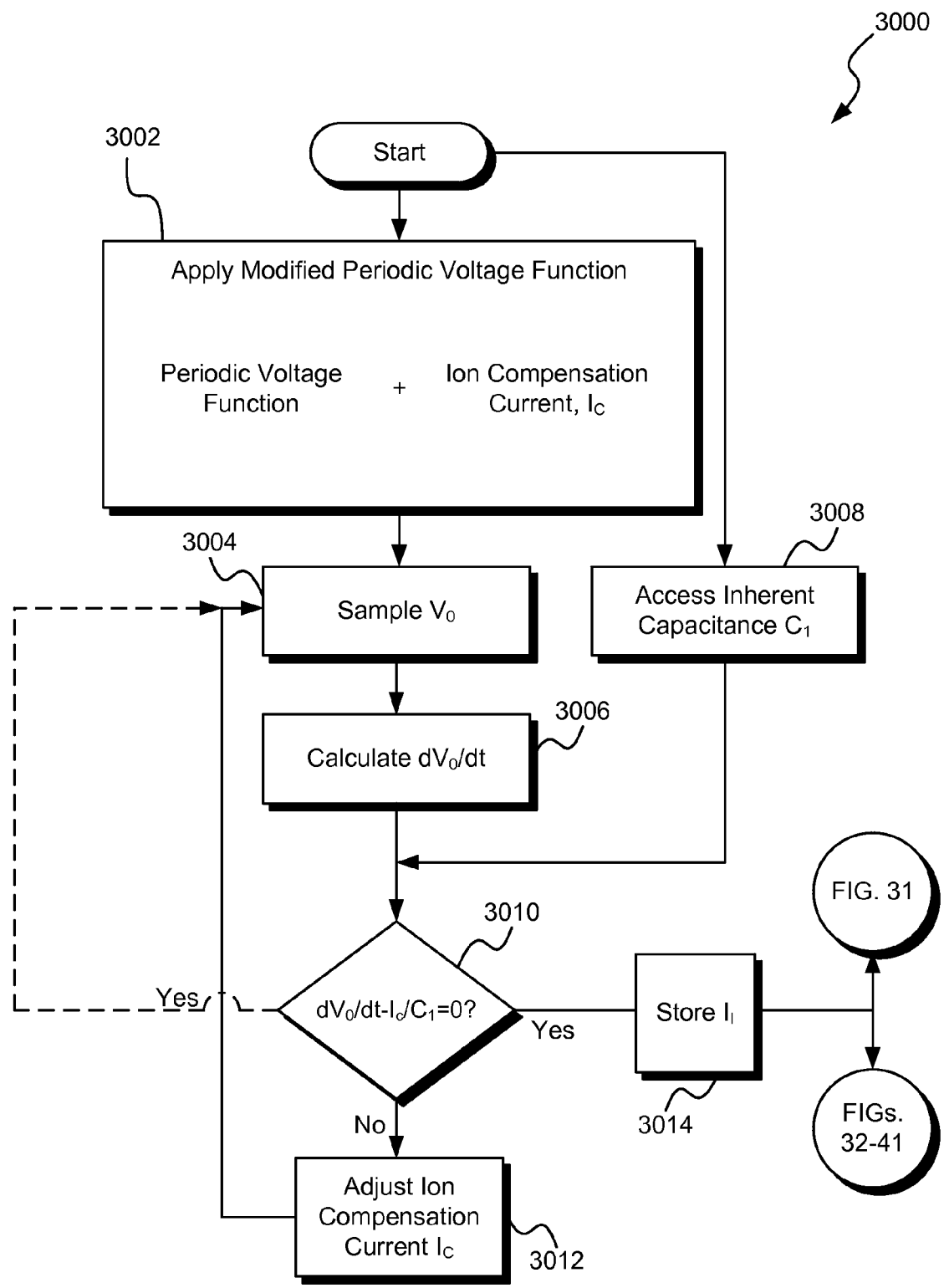
FIG. 30 illustrates one embodiment of a method of controlling an ion energy distribution of ions impacting a surface of a substrate.

FIG. 30 illustrates another embodiment of a method of controlling an ion energy distribution of ions impacting a surface of a substrate. In some embodiments, as discussed above, it may be desirable to achieve a narrow IEDF width (e.g., a minimum IEDF width or in the alternative, ~6% full-width half maximum). As such, the method 3000 can provide a modified periodic voltage function to the chamber and to the substrate support such that a constant substrate voltage, and hence sheath voltage, exists at the surface of the substrate. This in turn accelerates ions across the sheath at a substantially constant voltage thus enabling ions to impact the substrate with substantially the same ion energy, which in turn provides a narrow IEDF width. For instance, in FIG. 45 it can be seen that adjusting the ion current compensation, $I_C$, can cause the substrate voltage, $V_{sub}$, between pulses to have a constant, or substantially constant voltage thus causing the IEDF to narrow.

Figure 45:
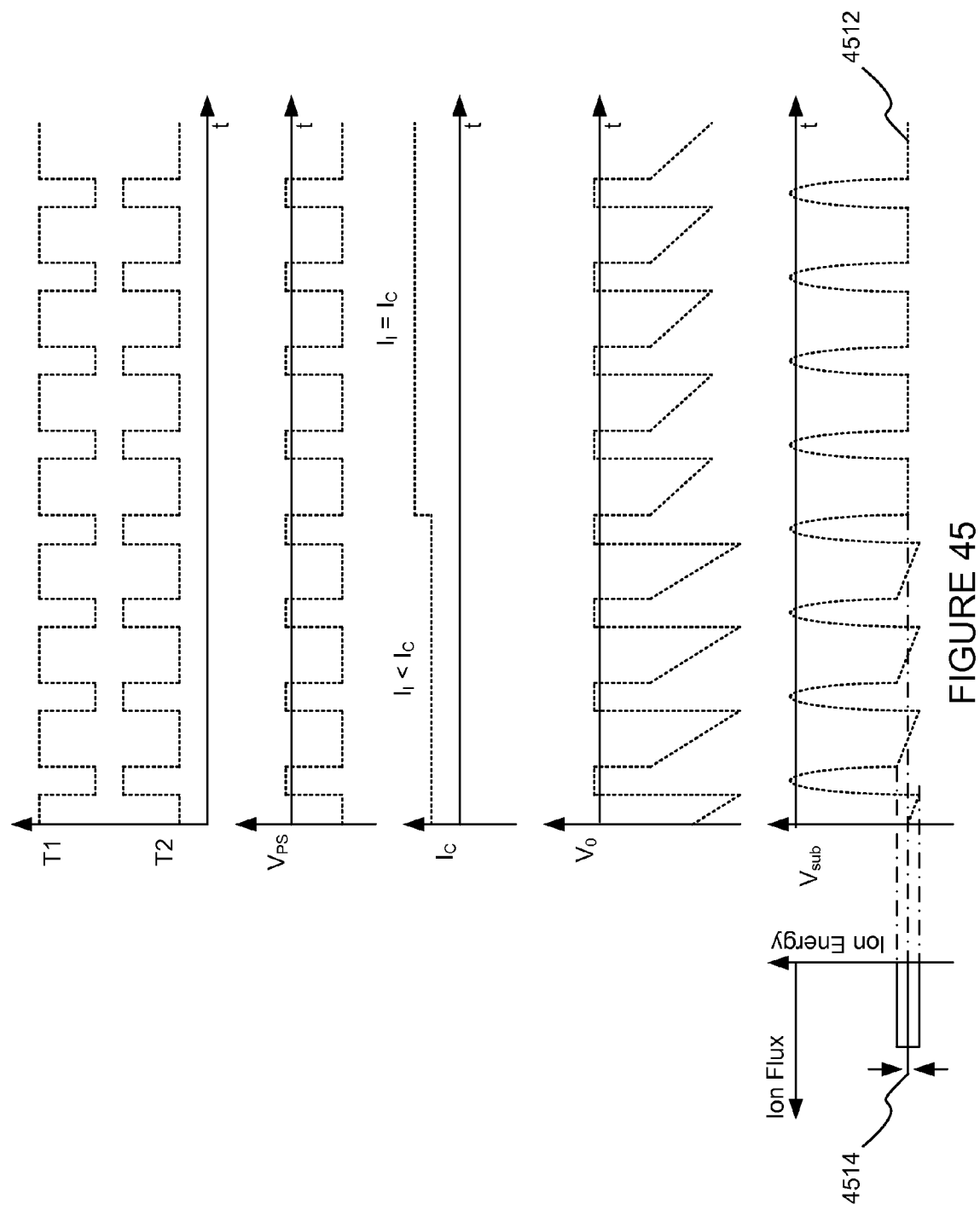
FIG. 45 illustrates the effects of making a final incremental change in ion current compensation, Ic, in order to match it to ion current $I_I$.

Such a modified periodic voltage function is achieved when the ion current compensation, $I_C$, equals the ion current, $I_I$, assuming no stray capacitances (see the last five cycles of the periodic voltage function ($V_0$) in FIG. 45). In the alternative, where stray capacitance, $C_{stray}$, is considered, the ion current compensation, $I_C$, is related to the ion current, $I_I$, according to Equation 2:

$$I_I = I_C \frac{C_1}{C_1 + C_{stray}} \quad \text{(Equation 2)}$$

where, $C_1$, is an effective capacitance (e.g., the inherent capacitance described with reference to FIGS. 3 and 13). The effective capacitance, $C_1$, can vary in time or be constant. For the purposes of this disclosure, the narrow IEDF width can exist when either $I_I=I_C$ or, in the alternative, when Equation 2 is met. FIGS. 45-50 use the nomenclature, $I_I=I_C$, but it should be understood that these equalities are merely simplifications of Equation 2, and thus Equation 2 could substitute for the equalities used in FIGS. 45-50. The stray capacitance, $C_{stray}$, is a cumulative capacitance of the plasma chamber as seen by the power supply. There are eight cycles illustrated in FIG. 45.

The method 3000 can begin with an application of a modified periodic voltage function (e.g., the modified periodic voltage function depicted in FIG. 14 or the modified periodic voltage function 4402 in FIG. 44) to the substrate support 3002 (e.g., substrate support 108 in FIG. 1). A voltage of the modified periodic voltage function can be sampled 3004 at two or more times, and from this sampling, a slope $dV_0/dt$ for at least a portion of a cycle of the modified periodic voltage function can be calculated 3006 (e.g., a slope of the portion between the pulses or the fourth portion 1408). At some point before a decision 3010, a previously-determined value of an effective capacitance $C_1$ (e.g., inherent capacitance $C_1$ in FIG. 13, and an inherent capacitance C10 in FIG. 3) can be accessed 3008 (e.g., from a memory or from a user input). Based on the slope, $dV_0/dt$, the effective capacitance, $C_1$, and the ion current compensation, $I_C$, a function $f$ (Equation 3), can be evaluated for each value of the ion current compensation, $I_C$, as follows:

$$f(I_C) = \frac{dV_0}{dt} - \frac{I_C}{C_1} = 0 \quad \text{(Equation 3)}$$

If the function $f$ is true, then the ion current compensation, $I_C$, equals the ion current, $I_I$, or in the alternative, makes Equation 2 true, and a narrow IEDF width has been achieved 3010 (e.g., see FIG. 45). If the function $f$ is not true, then the ion current compensation, $I_C$, can be adjusted 3012 further until the function $f$ is true. Another way to look at this is that the ion current compensation, $I_C$, can be adjusted until it matches the ion current, $I_I$, (or in the alternative, meets the relationship of Equation 2), at which point a narrow IEDF width will exist. Such an adjustment to the ion current compensation, Ic, and resulting narrowing of the IEDF, can be seen in FIG. 45. The ion current, $I_I$, and the corresponding ion current compensation, Ic, can be stored (e.g., in a memory) in store operation 3014. The ion current, $I_C$, can vary in time, as can the effective capacitance, $C_1$.

When Equation 3 is met, ion current, $I_I$, is known (either because $I_C=I_I$, or because Equation 2 is true). Thus, the method 3000 enables remote and non-invasive measurements of ion current, $I_I$, in real time without affecting the plasma. This leads to a number of novel metrics such as those that will be described with reference to FIGS. 32-41 (e.g., remote monitoring of plasma density and remote fault detection of the plasma source).

Figure 44:
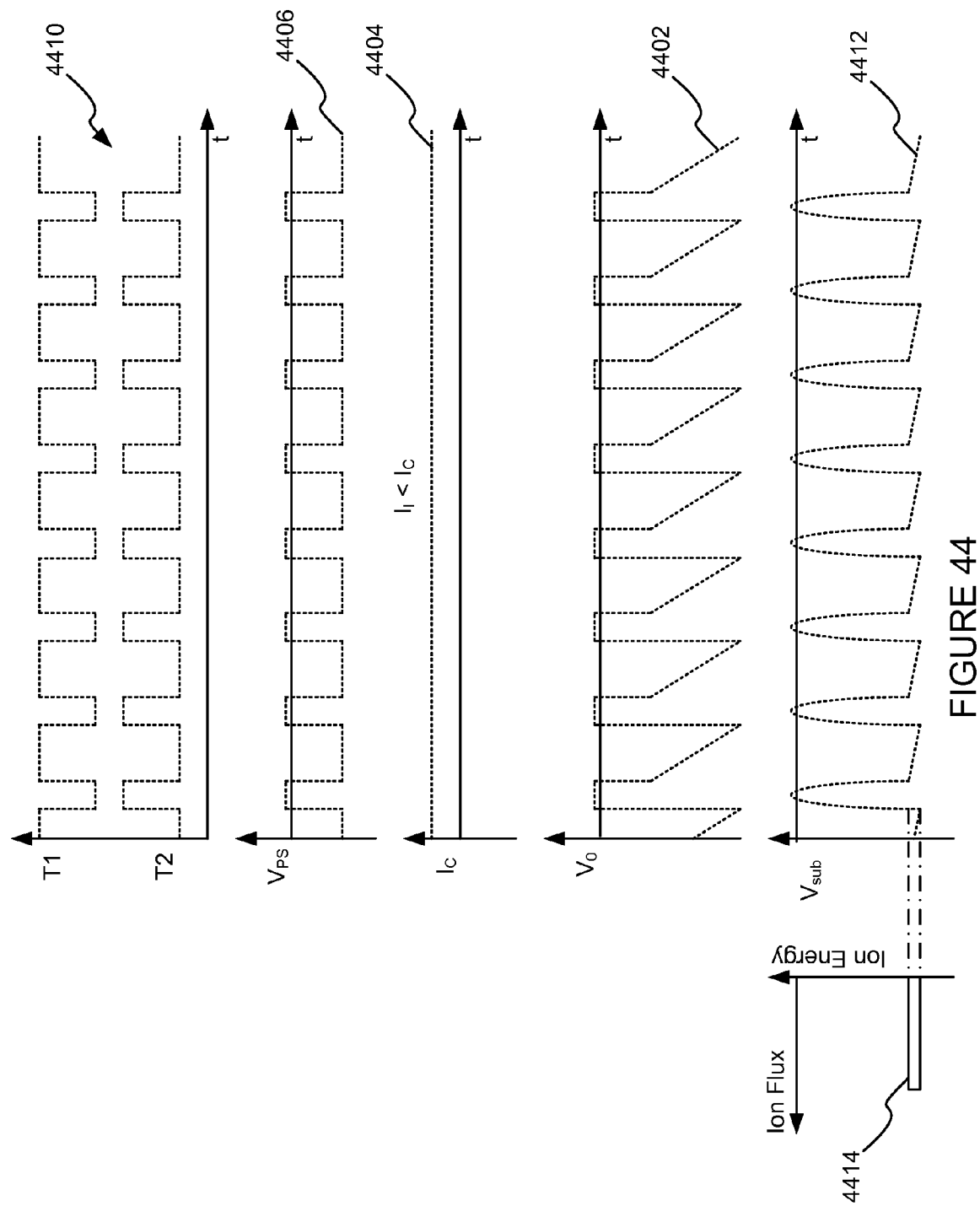
FIG. 44 illustrates various waveforms at different points in the systems herein disclosed.

While adjusting 3012 the compensation current, $I_C$, the ion energy will likely be broader than a delta function and the ion energy will resemble that of either FIG. 15B, 15C, or 44. However, once the compensation current, $I_C$, is found that meets Equation 2, the IEDF will appear as illustrated in FIG. 15A or the right portion of FIG. 45—as having a narrow IEDF width (e.g., a minimum IEDF width). This is because the voltage between pulses of the modified periodic voltage function causes a substantially constant sheath or substrate voltage, and hence ion energy, when $I_C=I_I$ (or alternatively when Equation 2 is true). In FIG. 46 the substrate voltage, 4608, includes pulses between the constant voltage portions. These pulses have such a short duration that their effect on ion energy and IEDF is negligible and thus the substrate voltage 4608 is referred to as being substantially constant.

The following provides further details about each of the method steps illustrated in FIG. 30. In one embodiment, the modified periodic voltage function can have a waveform like that illustrated in FIG. 14 and can include a first portion (e.g., first portion 1402), a second portion (e.g., 1404), a third portion (e.g., third portion 1406), and a fourth portion (e.g., fourth portion 1408), where the third portion can have a voltage step, $\Delta V$, and the fourth portion can have a slope, $dV_0/dt$. The slope, $dV_0/dt$, can be positive, negative, or zero. The modified periodic voltage function 1400 can also be described as having pulses comprising the first portion 1402, the second portion 1404, and the third portion 1406, and a portion between the pulses (fourth portion 1408).

The modified periodic voltage function can be measured as $V_0$ in FIG. 3 and can appear as the modified periodic voltage function 4402 in FIG. 44. The modified period voltage function 4402 is produced by combining the power supply voltage 4406 (also known as the periodic voltage function) with the ion current compensation 4404. The power supply voltage 4406 is largely responsible for generating and shaping the pulses of the modified periodic voltage function 4402 and the ion current compensation 4404 is largely responsible for generating and shaping the portion between the pulses, which is often a straight sloped voltage. Increasing the ion current compensation, Ic, causes a decrease in a magnitude of the slope of the portion between the pulses as seen in FIG. 45. Decreasing a magnitude of the power supply voltage 4606 causes a decrease in a magnitude of the amplitude of the pulses and the peak-to-peak voltage of the modified periodic voltage function 4602 as seen in FIG. 46.

In cases where the power supply is a switch-mode power supply, the switching diagram 4410 of a first switch T1 and a second switch T2 can apply. For instance, the first switch T1 can be implemented as the switch T1 in FIG. 3 and the second switch T2 can be implemented as the second switch T2 in FIG. 3. The two switches are illustrated as having identical switching times, but being 180° out of phase. In other embodiments, the switches may have a slight phase offset such as that illustrated in FIG. 4. When the first switch T1 is on, the power supply voltage is drawn to a maximum magnitude, which is a negative value in FIG. 44 since the power supply has a negative bus voltage. The second switch T2 is turned off during this period so that the power supply voltage 4406 is isolated from ground. When the switches reverse, the power supply voltage 4406 approaches and slightly passes ground. In the illustrated embodiment, there are two pulse widths, but this is not required. In other embodiments, the pulse width can be identical for all cycles. In other embodiments, the pulse width can be varied or modulated in time.

The modified periodic voltage function can be applied to the substrate support 3002, and sampled 3004 as $V_O$ at a last accessible point before the modified periodic voltage function reaches the substrate support (e.g., between the switch mode power supply and the effective capacitance). The unmodified periodic voltage function (or power supply voltage 4406 in FIG. 44) can be sourced from a power supply such as the switch mode power supply 1206 in FIG. 12. The ion current compensation 4404 in FIG. 44 can be sourced from a current source such as the ion current compensation component 1260 in FIG. 12 or 1360 in FIG. 13.

A portion of or the whole modified periodic voltage function can be sampled 3004. For instance, the fourth portion (e.g., fourth portion 1408) can be sampled. The sampling 3004 can be performed between the power supply and the substrate support. For instance, in FIG. 1, the sampling 3004 can be performed between the switch mode power supply 106 and the support 108. In FIG. 3, the sampling 3004 can be performed between the inductor L1 and the inherent capacitance C10. In one embodiment, the sampling 3004 can be performed at $V_O$ between the capacitance C3 and the inherent capacitance C10. Since the inherent capacitance C10 and the elements representing the plasma (R2, R3, C1, and C2) are not accessible for real time measurement, the sampling 3004 is typically performed to the left of the inherent capacitance C10 in FIG. 3. Although the inherent capacitance C10 typically is not measured during processing, it is typically a known constant, and can therefore be set during manufacturing. At the same time, in some cases the inherent capacitance C10 can vary with time.

While only two samples of the modified periodic voltage function are needed in some embodiments, in others, hundreds, thousands, or tens of thousands of samples can be taken for each cycle of the modified periodic voltage function. For instance, the sampling rate can be greater than 400 kHz. These sampling rates enable more accurate and detailed monitoring of the modified periodic voltage function and its shape. In this same vein, more detailed monitoring of the periodic voltage function allows more accurate comparisons of the waveform: between cycles, between different process conditions, between different processes, between different chambers, between different sources, etc. For instance, at these sampling rates, the first, second, third, and fourth portions 1402, 1404, 1406, 1408 of the periodic voltage function illustrated in FIG. 14 can be distinguished, which may not be possible at traditional sampling rates. In some embodiments, the higher sampling rates enable resolving of the voltage step, $\Delta V$, and the slope, $dV_O/dt$, which are not possible in the art. In some embodiments, a portion of the modified periodic voltage function can be sampled while other portions are not sampled.

The calculation 3006 of the slope, $dV_O/dt$, can be based on a plurality of $V_O$ measurements taken during the time t (e.g., the fourth portion 1408). For instance, a linear fit can be performed to fit a line to the $V_O$ values where the slope of the line gives the slope, $dV_O/dt$. In another instance, the $V_O$ values at the beginning and end of time t (e.g., the fourth portion 1408) in FIG. 14 can be ascertained and a line can be fit between these two points with the slope of the line given as $dV_O/dt$. These are just two of numerous ways that the slope, $dV_O/dt$, of the portion between the pulses can be calculated.

The decision 3010 can be part of an iterative loop used to tune the IEDF to a narrow width (e.g., a minimum width, or in the alternative, 6% full-width half maximum). Equation 3 only holds true where the ion current compensation, Ic, is equal to the ion current, $I_I$ (or in the alternative, is related to $I_I$ according to Equation 2), which only occurs where there is a constant substrate voltage and thus a constant and substantially singular ion energy (a narrow IEDF width). A constant substrate voltage 4608 ($V_{sub}$) can be seen in FIG. 46. Thus, either ion current, $I_I$, or alternatively ion current compensation, Ic, can be used in Equation 3.

Alternatively, two values along the fourth portion 1408 (also referred to as the portion between the pulses) can be sampled for a first cycle and a second cycle and a first and second slope can be determined for each cycle, respectively. From these two slopes, an ion current compensation, Ic, can be determined which is expected to make Equation 3 true for a third, but not-yet-measured, slope. Thus, an ion current, $I_I$, can be estimated that is predicted to correspond to a narrow IEDF width. These are just two of the many ways that a narrow IEDF width can be determined, and a corresponding ion current compensation, Ic, and/or a corresponding ion current, $I_I$, can be found.

The adjustment to the ion current compensation, Ic, 3012 can involve either an increase or a decrease in the ion current compensation, Ic, and there is no limitation on the step size for each adjustment. In some embodiments, a sign of the function ƒ in Equation 3 can be used to determine whether to increase or decrease the ion current compensation. If the sign is negative, then the ion current compensation, Ic, can be decreased, while a positive sign can indicate the need to increase the ion current compensation, Ic.

Once an ion current compensation, Ic, has been identified that equals the ion current, $I_I$ (or in the alternative, is related thereto according to Equation 2), the method 3000 can advance to further set point operations (see FIG. 31) or remote chamber and source monitoring operations (see FIGS. 32-41). The further set point operations can include setting the ion energy (see also FIG. 46) and the distribution of ion energy or IEDF width (see also FIG. 47). The source and chamber monitoring can include monitoring plasma density, source supply anomalies, plasma arcing, and others.

Furthermore, the method 3000 can optionally loop back to the sampling 3004 in order to continuously (or in the alternative, periodically) update the ion current compensation, Ic. For instance, the sampling 3004, calculation 3006, the decision 3010, and the adjusting 3012 can periodically be performed given a current ion current compensation, Ic, in order to ensure that Equation 3 continues to be met. At the same time, if the ion current compensation, Ic, that meets Equation 3 is updated, then the ion current, $I_I$, can also be updated and the updated value can be stored 3014.

While the method 3000 can find and set the ion current compensation, Ic, so as to equal the ion current, $I_I$, or in the alternative, to meet Equation 2, a value for the ion current compensation, Ic, needed to achieve a narrow IEDF width can be determined without (or in the alternative, before) setting the ion current, $I_C$, to that value. For instance, by applying a first ion current compensation, $Ic_1$, for a first cycle and measuring a first slope, $dV_{O1}/dt$, of the voltage between the pulses, and by applying a second ion current compensation, $Ic_2$, for a second cycle and measuring a second slope, $dV_{O2}/dt$, of the voltage between the pulses, a third slope, $dV_{O3}/dt$, associated with a third ion current compensation, $Ic_3$, can be determined at which Equation 3 is expected to be true. The third ion current compensation, $Ic_3$, can be one that if applied would result in a narrow IEDF width. Hence, the ion current compensation, Ic, that meets Equation 3 and thus corresponds to ion current, $I_I$, can be determined with only a single adjustment of the ion current compensation. The method 3000 can then move on to the methods described in FIG. 31 and/or FIGS. 32-41 without ever setting the ion current, $I_C$, to a value needed to achieve the narrow IEDF width. Such an embodiment may be carried out in order to increase tuning speeds.

FIG. 31 illustrates methods for setting the IEDF width and the ion energy. The method originates from the method 3000 illustrated in FIG. 30, and can take either of the left path 3100 (also referred to as an IEDF branch) or the right path 3101 (also referred to as an ion energy branch), which entail setting of the IEDF width and the ion energy, respectively. Ion energy, eV, is proportional to a voltage step, $\Delta V$, or the third portion 1406 of the modified periodic voltage function 1400 of FIG. 14. The relationship between ion energy, eV, and the voltage step, $\Delta V$, can be written as Equation 4:

$$eV = \Delta V \frac{C_1}{C_2 + C_1} \quad \text{(Equation 4)}$$

where $C_1$ is the effective capacitance (e.g., chuck capacitance; inherent capacitance, C10, in FIG. 3; or inherent capacitance, C1, in FIG. 13), and $C_2$ is a sheath capacitance (e.g., the sheath capacitance C4 in FIG. 3 or the sheath capacitance C2 in FIG. 13). The sheath capacitance, $C_2$, may include stray capacitances and depends on the ion current, $I_I$. The voltage step, $\Delta V$, can be measured as a change in voltage between the second portion 1404 and the fourth portion 1408 of the modified periodic voltage function 1400. By controlling and monitoring the voltage step, $\Delta V$, (which is a function of a power supply voltage or a bus voltage such as bus voltage, $V_{bus}$ in FIG. 3), ion energy, eV, can be controlled and known.

At the same time, the IEDF width can be approximated according to Equation 5:

$$\text{IEDF width} = V_{PP} - \Delta V - \frac{It}{C} \quad \text{(Equation 5)}$$

where I is $I_I$ where C is $C_{series}$, or I is $I_C$ where C is $C_{effective}$. Time, t, is the time between pulses, $V_{PP}$, is the peak-to-peak voltage, and $\Delta V$ is the voltage step.

Additionally, sheath capacitance, $C_2$, can be used in a variety of calculations and monitoring operations. For instance, the Debye sheath distance, $\lambda_{sheath}$, can be estimated as follows:

$$\lambda_{sheath} = \frac{\epsilon A}{C_2} \quad \text{(Equation 6)}$$

where $\epsilon$ is vacuum permittivity and A is an area of the substrate (or in an alternative, a surface area of the substrate support). In some high voltage applications, Equation 6 is written as equation 7:

$$\lambda_{sheath} = \sqrt{\frac{T_e \cdot \epsilon_0}{n_e q}} \cdot \left(\frac{V}{2} T_e\right)^{.75} \quad \text{(Equation 7)}$$

Additionally, an e-field in the sheath can be estimated as a function of the sheath capacitance, $C_2$, the sheath distance, $\lambda_{sheath}$, and the ion energy, eV. Sheath capacitance, $C_2$, along with the ion current, $I_1$, can also be used to determine plasma density, $n_e$, from Equation 8 where saturation current, $I_{sat}$, is linearly related to the compensation current, $I_C$, for singly ionized plasma.

$$I_{sat} = \sum n_i q_i \sqrt{\frac{kT_e}{m_i}} A \approx n_e q \sqrt{\frac{kT_e}{\langle m \rangle}} A \quad \text{(Equation 8)}$$

An effective mass of ions at the substrate surface can be calculated using the sheath capacitance, $C_2$ and the saturation current, $I_{sat}$. Plasma density, $n_e$, electric field in the sheath, ion energy, eV, effective mass of ions, and a DC potential of the substrate, $V_{DC}$, are fundamental plasma parameters that are typically only monitored via indirect means in the art. This disclosure enables direct measurements of these parameters thus enabling more accurate monitoring of plasma characteristics in real time.

As seen in Equation 4, the sheath capacitance, $C_2$, can also be used to monitor and control the ion energy, eV, as illustrated in the ion energy branch 3101 of FIG. 31. The ion energy branch 3101 starts by receiving a user selection of ion energy 3102. The ion energy branch 3101 can then set an initial power supply voltage for the switch-mode power supply that supplies the periodic voltage function 3104. At some point before a sample periodic voltage operation 3108, the ion current can also be accessed 3106 (e.g., accessed from a memory). The periodic voltage can be sampled 3108 and a measurement of the third portion of the modified periodic voltage function can be measured 3110. Ion energy, $I_I$, can be calculated from the voltage step, $\Delta V$, (also referred to as the third portion (e.g., third portion 1406)) of the modified periodic voltage function 3112. The ion energy branch 3101 can then determine whether the ion energy equals the defined ion energy 3114, and if so, the ion energy is at the desired set point and the ion energy branch 3101 can come to an end. If the ion energy is not equal to the defined ion energy, then the ion energy branch 3101 can adjust the power supply voltage 3116, and again sample the periodic voltage 3108. The ion energy branch 3101 can then loop through the sampling 3108, measuring 3110, calculating 3112, decision 3114, and the setting 3116 until the ion energy equals the defined ion energy.

The method for monitoring and controlling the IEDF width is illustrated in the IEDF branch 3100 of FIG. 31. The IEDF branch 3100 includes receiving a user selection of an IEDF width 3150 and sampling a current IEDF width 3152. A decision 3154 then determines whether the defined IEDF width equals the current IEDF width, and if the decision 3152 is met, then the IEDF width is as desired (or defined), and the IEDF branch 3100 can come to an end. However, if the current IEDF width does not equal the defined IEDF width, then the ion current compensation, Ic, can be adjusted 3156. This determination 3154 and the adjustment 3156 can continue in a looping manner until the current IEDF width equals the defined IEDF width.

In some embodiments, the IEDF branch 3100 can also be implemented to secure a desired IEDF shape. Various IEDF shapes can be generated and each can be associated with a different ion energy and IEDF width. For instance, a first IEDF shape may be a delta function while a second IEDF shape may be a square function. Other IEDF shapes may be cupped. Examples of various IEDF shapes can be seen in FIG. 11.

With knowledge of the ion current, $I_I$, and the voltage step, $\Delta V$, Equation 4 can be solved for ion energy, eV. The voltage step, $\Delta V$, can be controlled by changing the power supply voltage which in turn causes the voltage step, $\Delta V$, to change. A larger power supply voltage causes an increase in the voltage step, $\Delta V$, and a decrease in the power supply voltage causes a decrease in the voltage step, $\Delta V$. In other words, increasing the power supply voltage results in a larger ion energy, eV.

Furthermore, since the above systems and methods operate on a continuously varying feedback loop, the desired (or defined) ion energy and IEDF width can be maintained despite changes in the plasma due to variations or intentional adjustments to the plasma source or chamber conditions.

Although FIGS. 30-41 have been described in terms of a single ion energy, one of skill in the art will recognize that these methods of generating and monitoring a desired (or defined) IEDF width (or IEDF shape) and ion energy can be further utilized to produce and monitor two or more ion energies, each having its own IEDF width (or IEDF shape). For instance, by providing a first power supply voltage, $V_{PS}$, in a first, third, and fifth cycles, and a second power supply voltage in a second, fourth, and sixth cycles, two distinct and narrow ion energies can be achieved for ions reaching the surface of the substrate (e.g., FIG. 42A). Using three different power supply voltages results in three different ion energies (e.g., FIG. 42B). By varying a time during which each of multiple power supply voltages is applied, or the number of cycles during which each power supply voltage level is applied, the ion flux of different ion energies can be controlled (e.g., FIG. 42C).

The above discussion has shown how combining a periodic voltage function provided by a power supply with an ion current compensation provided by an ion current compensation component, can be used to control an ion energy and IEDF width and/or IEDF shape of ions reaching a surface of a substrate during plasma processing.

Some of the heretofore mentioned controls are enabled by using some combination of the following: (1) a fixed waveform (consecutive cycles of the waveform are the same); (2) a waveform having at least two portions that are proportional to an ion energy and an IEDF (e.g., the third and fourth portions 1406 and 1408 illustrated in FIG. 14); and (3) a high sampling rate (e.g., 125 MHz) that enables accurate monitoring of the distinct features of the waveform. For instance, where the prior art, such as linear amplifiers, sends a waveform to the substrate that is similar to the modified periodic voltage function, undesired variations between cycles make it difficult to use those prior art waveforms to characterize the ion energy or IEDF width (or IEDF shape).

Where linear amplifiers have been used to bias a substrate support, the need to sample at a high rate has not been seen since the waveform is not consistent from cycle to cycle and thus resolving features of the waveform (e.g., a slope of a portion between pulses) typically would not provide useful information. Such useful information does arise when a fixed waveform is used, as seen in this and related disclosures.

The herein disclosed fixed waveform and the high sampling rate further lead to more accurate statistical observations being possible. Because of this increased accuracy, operating and processing characteristics of the plasma source and the plasma in the chamber can be monitored via monitoring various characteristics of the modified periodic voltage function. For instance, measurements of the modified periodic voltage function enable remote monitoring of sheath capacitance and ion current, and can be monitored without knowledge of the chamber process or other chamber details. A number of examples follow to illustrate just some of the multitude of ways that the heretofore mentioned systems and methods can be used for non-invasive monitoring and fault detection of the source and chamber.

As an example of monitoring, and with reference to FIG. 14, the DC offset of the waveform 1400 can represent a health of the plasma source (hereinafter referred to as the "source"). In another, a slope of a top portion 1404 (the second portion) of a pulse of the modified periodic voltage function can be correlated to damping effects within the source. The standard deviation of the slope of the top portion 1404 from horizontal (illustrated as having a slope equal to 0) is another way to monitor source health based on an aspect of the waveform 1400. Another aspect involves measuring a standard deviation of sampled $V_0$ points along the fourth portion 1408 of the modified periodic voltage function and correlating the standard deviation to chamber ringing. For instance, where this standard deviation is monitored among consecutive pulses, and the standard deviation increases over time, this may indicate that there is ringing in the chamber, for instance in the e-chuck. Ringing can be a sign of poor electrical connections to, or in, the chamber or of additional unwanted inductance or capacitance.

Figure 32:
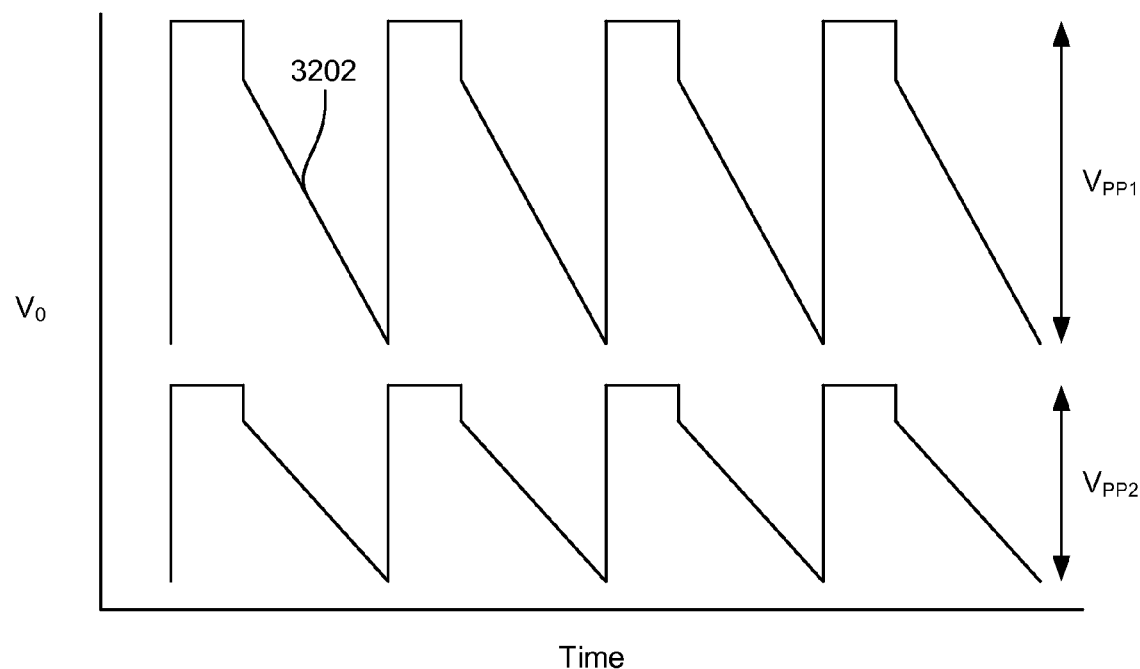
FIG. 32 illustrates two modified periodic voltage function waveforms delivered to the substrate support according to one embodiment of this disclosure.

FIG. 32 illustrates two modified periodic voltage functions delivered to the substrate support according to one embodiment of this disclosure. When compared, the two modified periodic voltage functions can be used for chamber matching or in situ anomaly or fault detection. For instance, one of the two modified periodic voltage functions can be a reference waveform and the second can be taken from a plasma processing chamber during calibration. Differences between the two modified periodic voltage functions (e.g., differences in peak-to-peak voltage, $V_{PP}$) can be used to calibrate the plasma processing chamber. Alternatively, the second modified periodic voltage function can be compared to the reference waveform during processing and any difference (e.g., shifts) in waveform characteristics can be indicative of a fault (e.g., a difference in the slope of a fourth portion 3202 of the modified periodic voltage functions).

Figure 33:
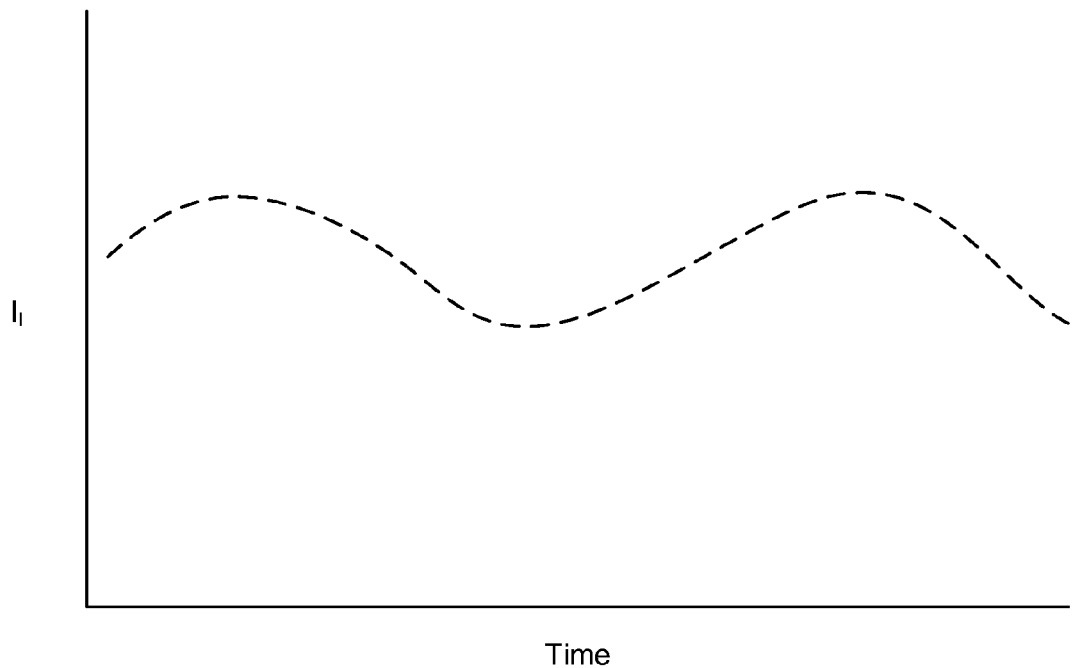
FIG. 33 illustrates an ion current waveform that can indicate plasma source instability or changes in the plasma density.

FIG. 33 illustrates an ion current waveform that can indicate plasma source instability and changes in the plasma density. Fluctuations in ion current, $I_I$, such as that illustrated in FIG. 33, can be analyzed to identify faults and anomalies in the system. For instance, the periodic fluctuations in FIG. 33 may indicate a low-frequency instability in the plasma source (e.g., plasma power supply 102). Such fluctuations in ion current, $I_I$, can also indicate cyclical changes in plasma density. This indicator and the possible faults or anomalies that it may indicate are just one of many ways that remote monitoring of the ion current, $I_I$, can be used to particular advantage.

Figure 34:
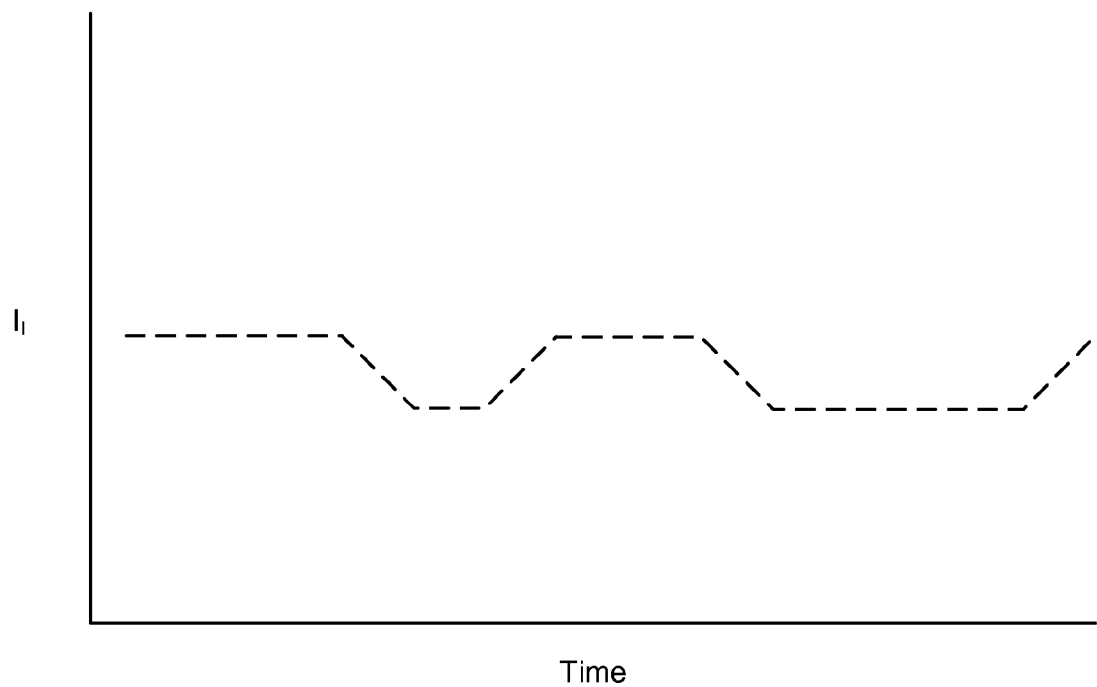
FIG. 34 illustrates an ion current, $I_I$, of a modified periodic voltage function waveform having a non-cyclical shape.

FIG. 34 illustrates an ion current, $I_I$, of a modified periodic voltage function having a non-cyclical shape. This embodiment of an ion current, $I_I$, can indicate non-cyclical fluctuations such as plasma instability and changes in plasma density. Such a fluctuation may also indicate various plasma instabilities such as arcing, formation of parasitic plasma, or drift in plasma density.

Figure 35:
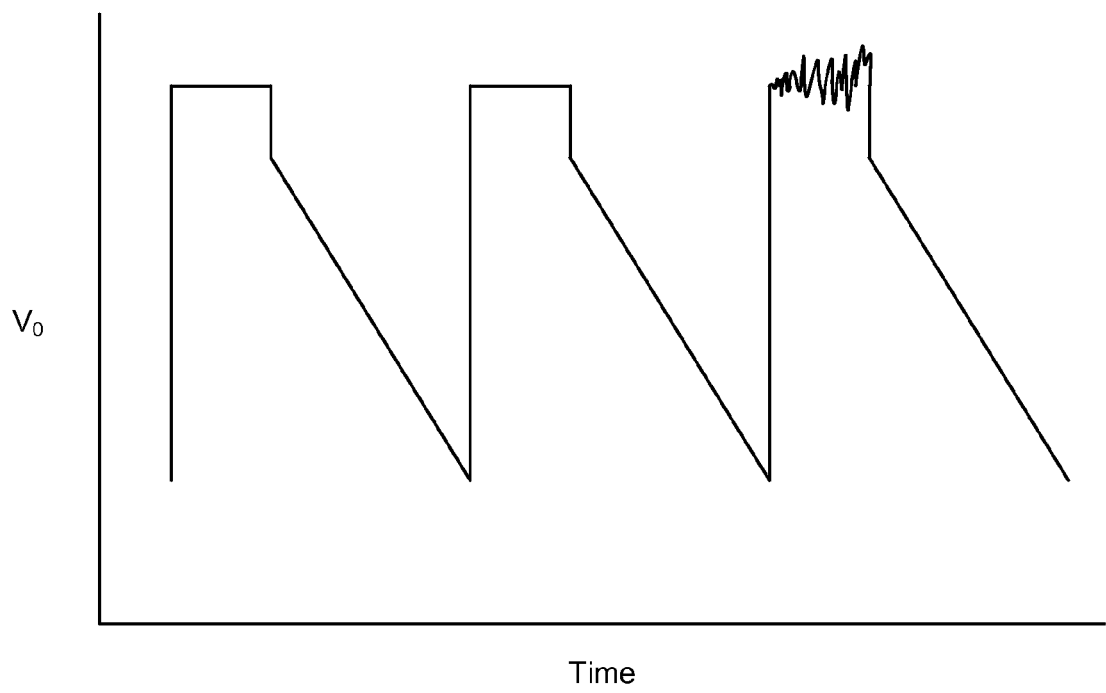
FIG. 35 illustrates a modified periodic voltage function waveform that can indicate faults within the bias supply.

FIG. 35 illustrates a modified periodic voltage function that can indicate faults within the bias supply. A top portion (also referred to herein as a second portion) of the third illustrated cycle shows anomalous behavior that may be indicative of ringing in the bias supply (e.g., power supply 1206 in FIG. 12). This ringing may be an indication of a fault within the bias supply. Further analysis of the ringing may identify characteristics that help to identify the fault within the power system.

Figure 36:
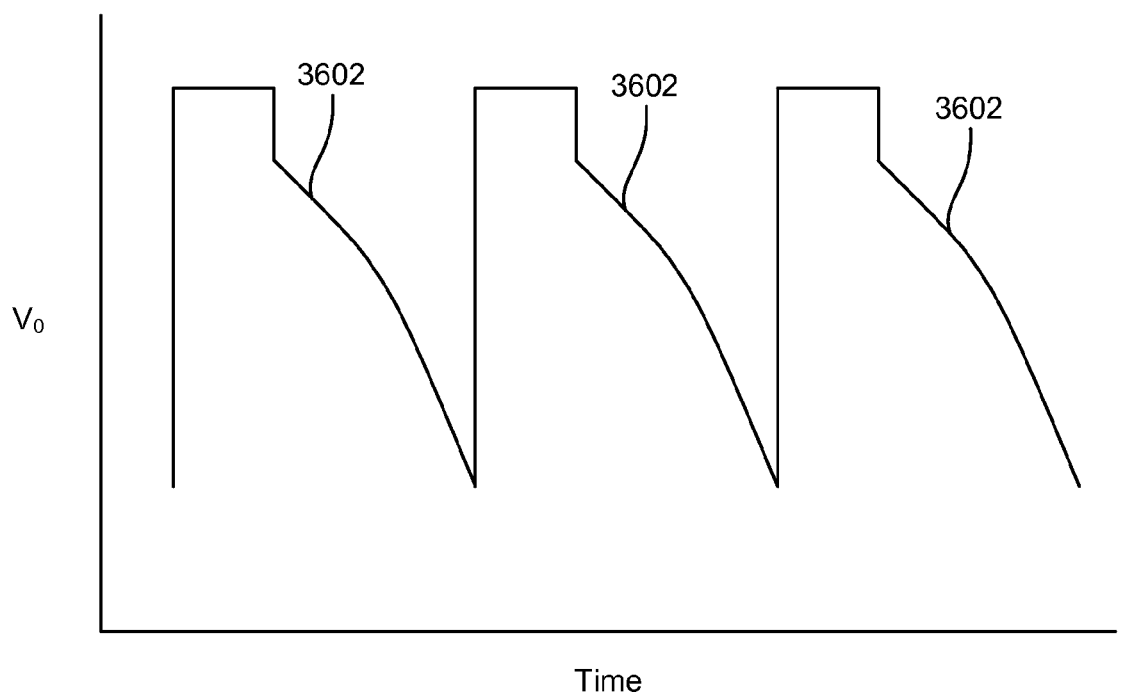
FIG. 36 illustrates a modified periodic voltage function waveform that can be indicative of a dynamic change in the system capacitance.

FIG. 36 illustrates a modified periodic voltage function that can be indicative of a dynamic (or nonlinear) change in a capacitance of the system. For instance, a stray capacitance that nonlinearly depends on voltage could result in such a modified periodic voltage function. In another example, plasma breakdown or a fault in the chuck could also result in such a modified periodic voltage function. In each of the three illustrated cycles a nonlinearity in the fourth portion 3602 of each cycle can be indicative of a dynamic change in the system capacitance. For instance, the nonlinearities can indicate a change in the sheath capacitance since other components of system capacitance are largely fixed.

Figure 37:
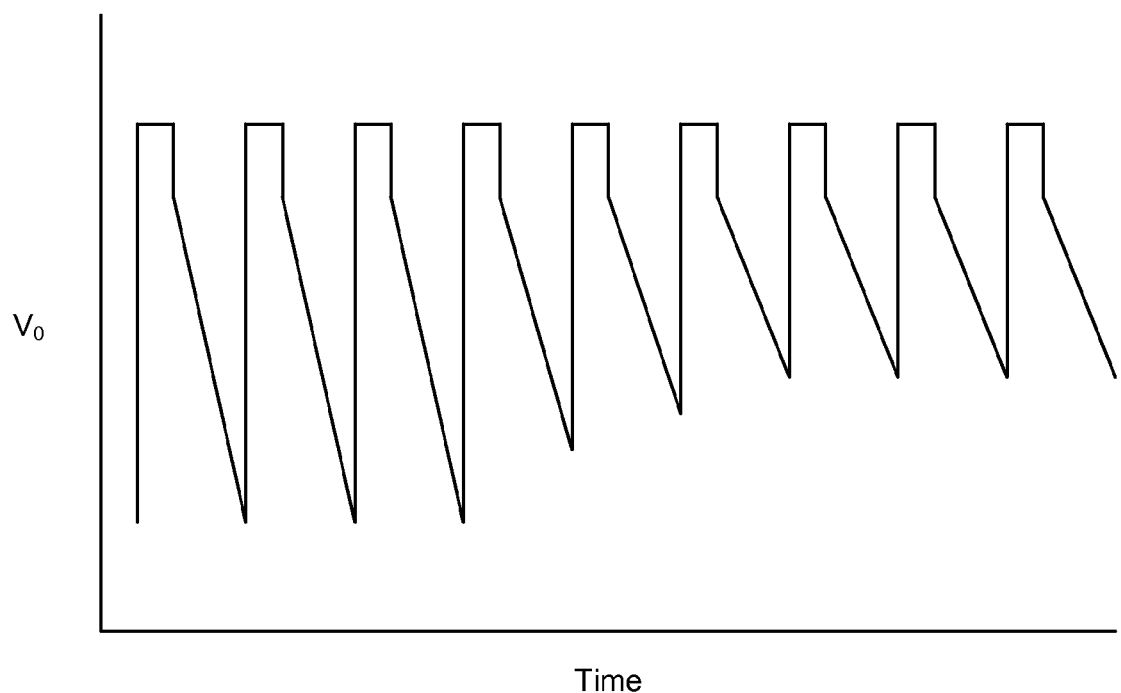
FIG. 37 illustrates a modified periodic voltage function waveform that may be indicative of changes in plasma density.

FIG. 37 illustrates a modified periodic voltage function that may be indicative of changes in plasma density. The illustrated modified periodic voltage function shows monotonic shifts in the slope $dV_0/dt$, which can indicate a change in plasma density. These monotonic shifts can provide a direct indication of an anticipated event, such as a process etch end point. In other embodiments, these monotonic shifts can indicate a fault in the process where no anticipated event exists.

Figure 38:
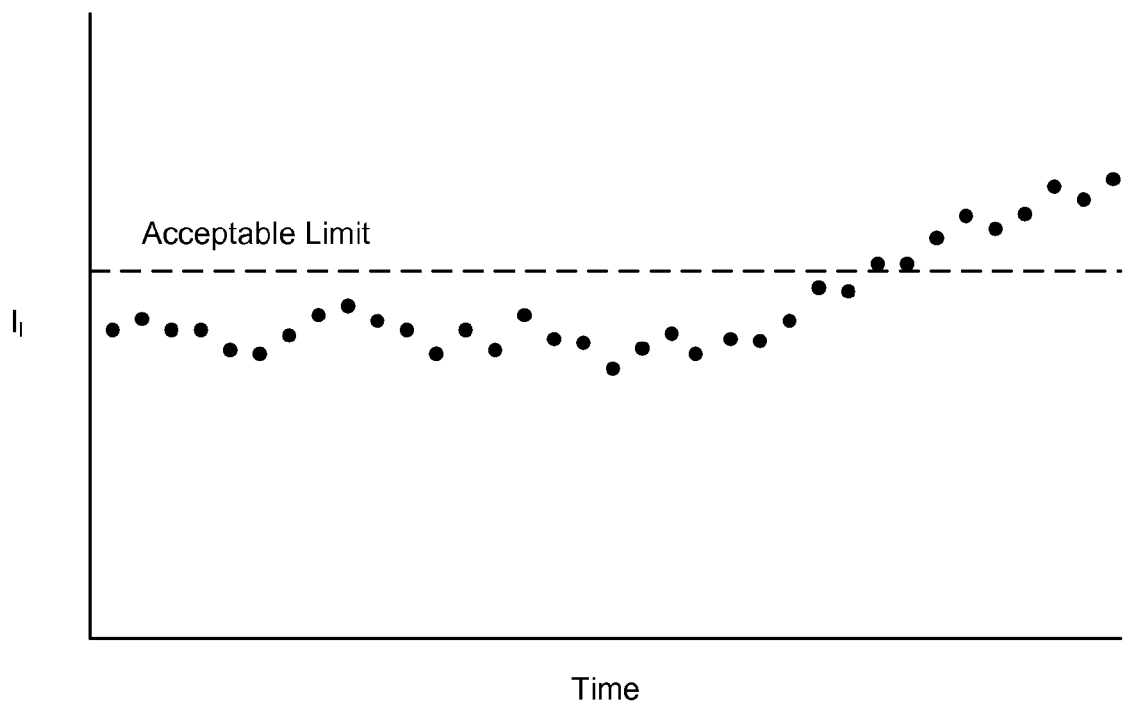
FIG. 38 illustrates a sampling of ion current for different process runs, where drift in the ion current can indicate system drift.

FIG. 38 illustrates a sampling of ion current for different process runs, where drift in the ion current can indicate system drift. Each data point can represent an ion current for a given run, where the acceptable limit is a user-defined or automated limit which defines an acceptable ion current. Drift in the ion current, which gradually pushes the ion current above the acceptable limit can indicate that substrate damage is possible. This type of monitoring can also be combined with any number of other traditional monitors, such as optical omission, thickness measurement, etc. These traditional types of monitors in addition to monitoring ion current drift can enhance existing monitoring and statistical control.

Figure 39:
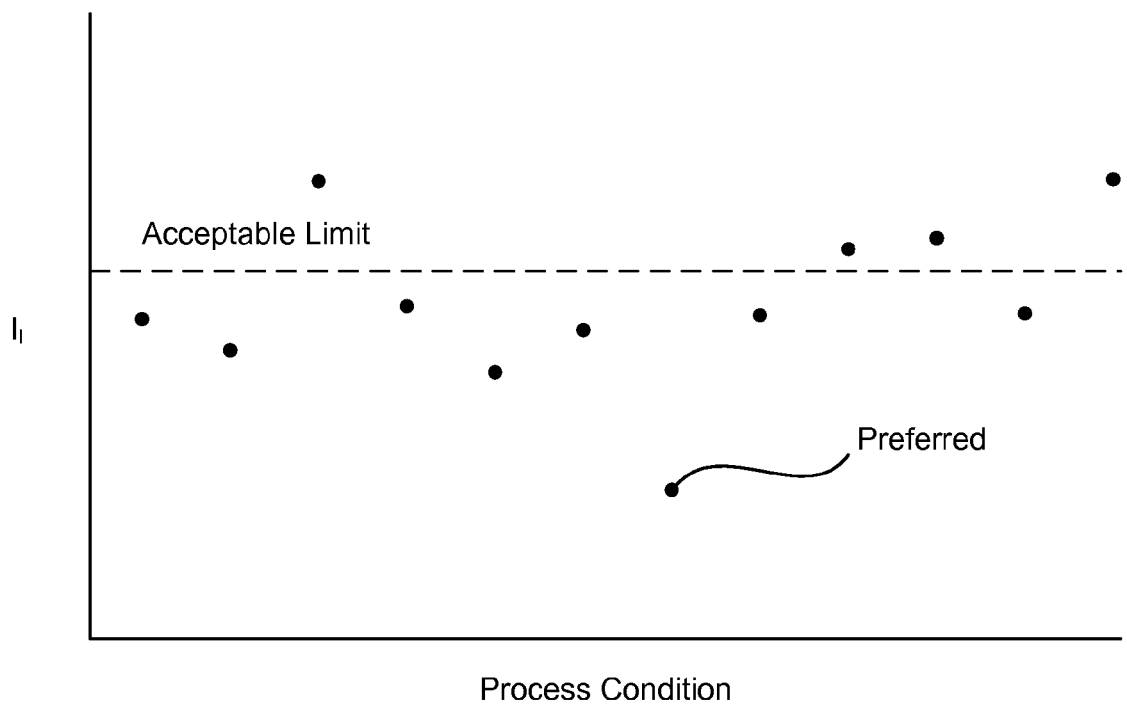
FIG. 39 illustrates a sampling of ion current for different process parameters.

FIG. 39 illustrates a sampling of ion current for different process parameters. In this illustration ion current can be used as a figure of merit to differentiate different processes and different process characteristics. Such data can be used in the development of plasma recipes and processes. For instance eleven process conditions could be tested resulting in the eleven illustrated ion current data points, and the process resulting in a preferred ion current can be selected as an ideal process, or in the alternative as a preferred process. For instance, the lowest ion current may be selected as the ideal process, and thereafter the ion current associated with the preferred process can be used as a metric to judge whether a process is being carried out with the preferred process condition(s). This figure of merit can be used in addition to or as an alternative to similar traditional merit characteristics such as rate, selectivity, and profile angle, to name a few non-limiting examples.

Figure 40:
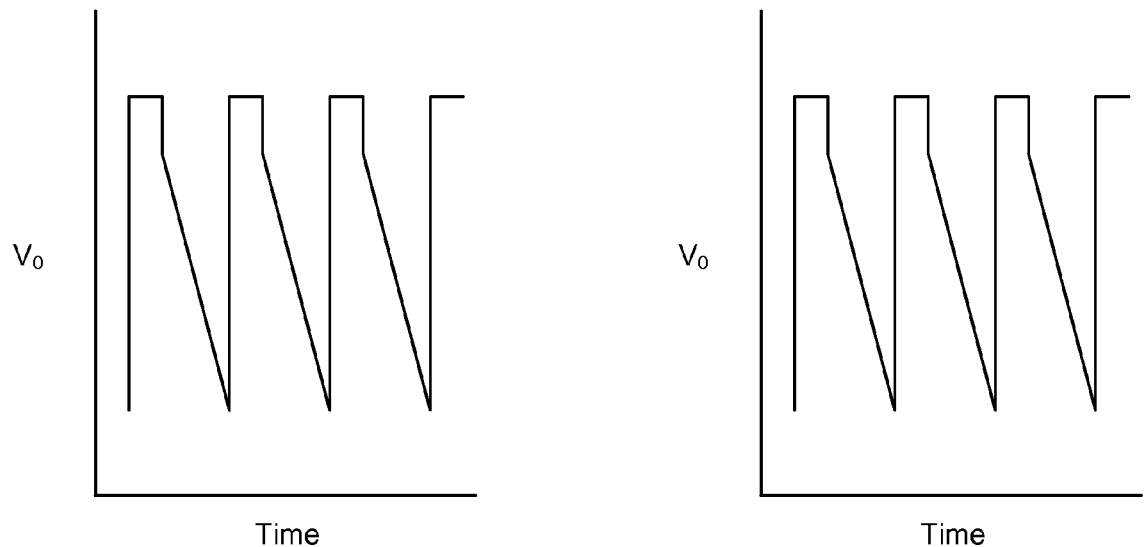
FIG. 40 illustrates two bias waveforms monitored without a plasma in the chamber.

FIG. 40 illustrates two modified periodic voltage functions monitored without a plasma in the chamber. These two modified periodic voltage functions can be compared and used to characterize the plasma chamber. In an embodiment the first modified periodic voltage function can be a reference waveform while the second modified periodic voltage function can be a currently-monitored waveform. These waveforms can be taken without a plasma in the processing chamber, for instance after a chamber clean or preventative maintenance, and therefore the second waveform can be used to provide validation of an electrical state of the chamber prior to release of the chamber into (or back into) production.

Figure 41:
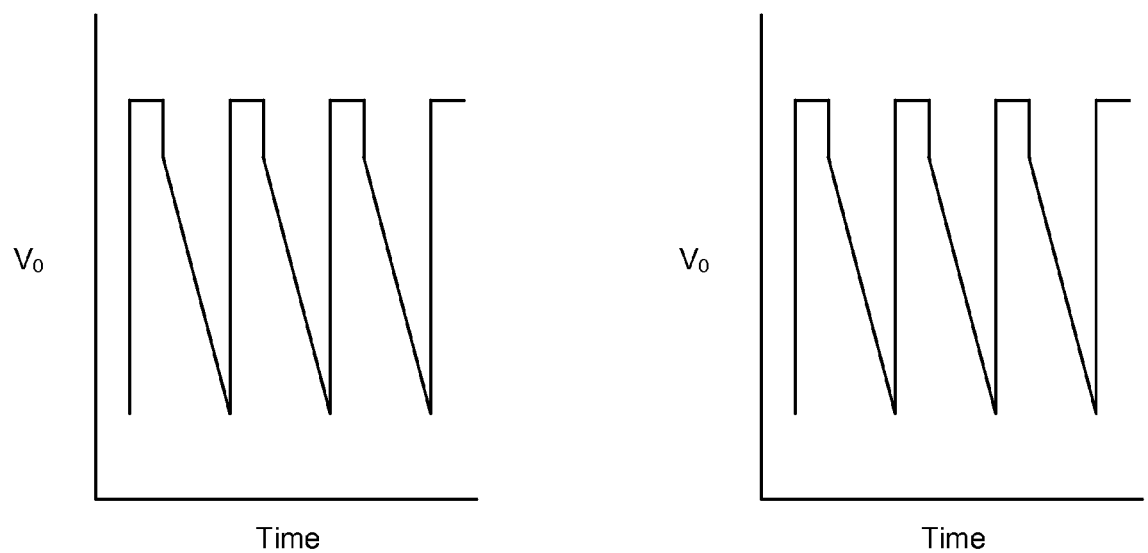
FIG. 41 illustrates two bias waveforms that can be used to validate a plasma process.
Figure 42A:
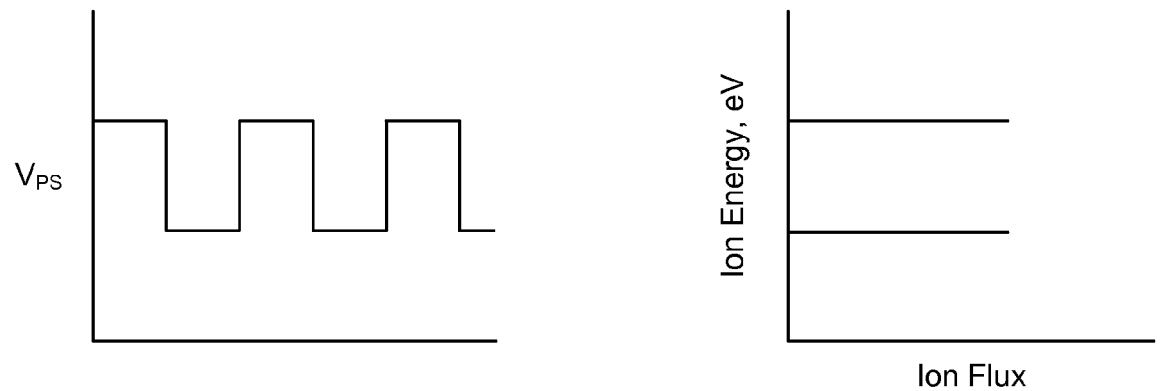
FIG. 42 illustrates a number of power supply voltages and ion energy plots showing the relationship between the power supply voltage and ion energy.
Figure 42B:
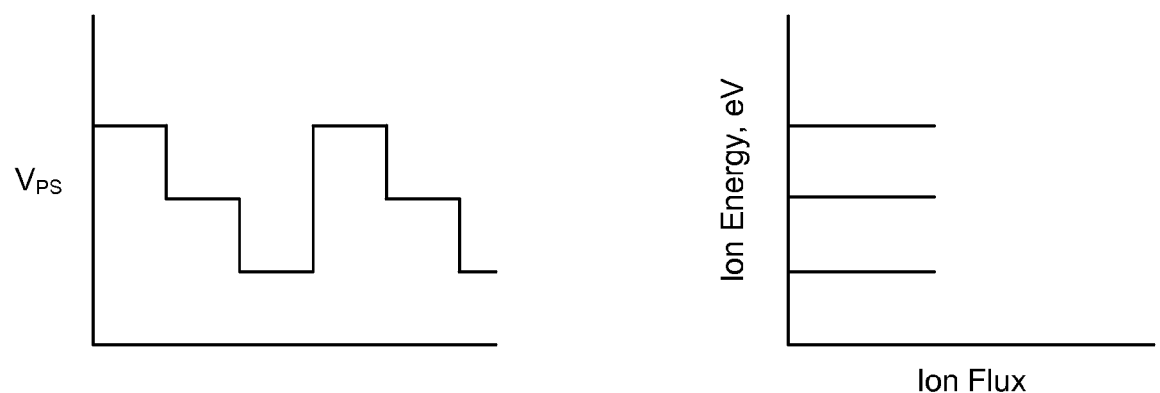
Figure 42C:
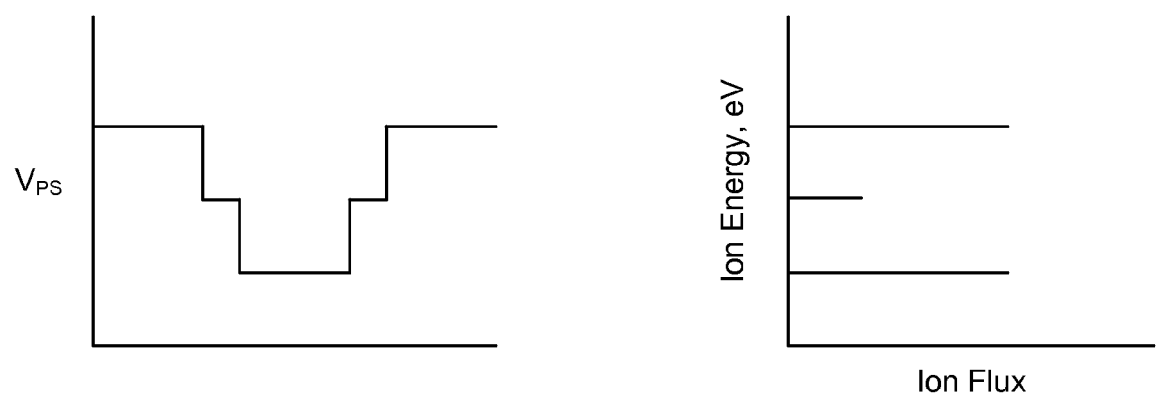

FIG. 41 illustrates two modified periodic voltage functions that can be used to validate a plasma process. The first modified periodic voltage function can be a reference waveform while the second modified periodic voltage function can be a currently monitored waveform. The currently monitored waveform can be compared to the reference waveform and any differences can indicate parasitic and/or non-capacitive impedance issues that are otherwise not detectable using traditional monitoring methods. For instance, the ringing seen on the waveform of FIG. 35 may be detected and could represent ringing in the power supply.

Any of the metrics illustrated in FIGS. 32-41 can be monitored while the method 3000 loops in order to update the ion current compensation, Ic, ion current, $I_I$, and/or the sheath capacitance, $C_{sheath}$. For instance, after each ion current, $I_I$, sample is taken in FIG. 38, the method 3000 can loop back to the sampling 3004 in order to determine an updated ion current, $I_I$. In another example, as a result of a monitoring operation, a correction to the ion current, $I_I$, ion energy, eV, or the IEDF width may be desired. A corresponding correction can be made and the method 3000 can loop back to the sampling 3004 to find a new ion current compensation, Ic, that meets Equation 3.

One of skill in the art will recognize that the methods illustrated in FIGS. 30, 31, and 43 do not require any particular or described order of operation, nor are they limited to any order illustrated by or implied in the figures. For instance, metrics (FIGS. 32-41) can be monitored before, during, or after setting and monitoring the IEDF width and/or the ion energy, eV.

FIG. 44 illustrates various waveforms at different points in the systems herein disclosed. Given the illustrated switching pattern 4410 for switching components of a switch mode power supply, power supply voltage, $V_{PS}$, 4406 (also referred to herein as a periodic voltage function), ion current compensation, Ic, 4404, modified periodic voltage function 4402, and substrate voltage, $V_{sub}$, 4412, the IEDF has the illustrated width 4414 (which may not be drawn to scale) or IEDF shape 4414. This width is wider than what this disclosure has referred to as a "narrow width." As seen, when the ion current compensation, Ic, 4404 is greater than the ion current, $I_I$, the substrate voltage, $V_{sub}$, 4412 is not constant. The IEDF width 4414 is proportional to a voltage difference of the sloped portion between pulses of the substrate voltage, $V_{sub}$, 4412.

Given this non-narrow IEDF width 4414, the methods herein disclosed call for the ion current compensation, Ic, to be adjusted until $I_C=I_I$ (or in the alternative are related according to Equation 2). FIG. 45 illustrates the effects of making a final incremental change in ion current compensation, Ic, in order to match it to ion current $I_I$. When $I_C=I_I$ the substrate voltage, $V_{sub}$, 4512 becomes substantially constant, and the IEDF width 4514 goes from non-narrow to narrow.

Once the narrow IEDF has been achieved, one can adjust the ion energy to a desired or defined value as illustrated in FIG. 46. Here, a magnitude of the power supply voltage (or in the alternative a bus voltage, $V_{bus}$, of a switch-mode power supply) is decreased (e.g., a maximum negative amplitude of the power supply voltage 4606 pulses is reduced). As a result, $\Delta V_1$ decreases to $\Delta V_2$ as does the peak-to-peak voltage, from $V_{PP1}$ to $V_{PP2}$. A magnitude of the substantially constant substrate voltage, $V_{sub}$, 4608 consequently decreases, thus decreasing a magnitude of the ion energy from 4615 to 4614 while maintaining the narrow IEDF width.

Whether the ion energy is adjusted or not, the IEDF width can be widened after the narrow IEDF width is achieved as shown in FIG. 47. Here, given $I_f=I_C$ (or in the alternative, Equation 2 giving the relation between $I_f$ and $I_C$), $I_C$ can be adjusted thus changing a slope of the portion between pulses of the modified periodic voltage function 4702. As a result of ion current compensation, Ic, and ion current, $I_f$, being not equal, the substrate voltage moves from substantially constant to non-constant. A further result is that the IEDF width 4714 expands from the narrow IEDF 4714 to a non-narrow IEDF 4702. The more that $I_C$ is adjusted away from $I_f$, the greater the IEDF 4714 width.

Figure 48:
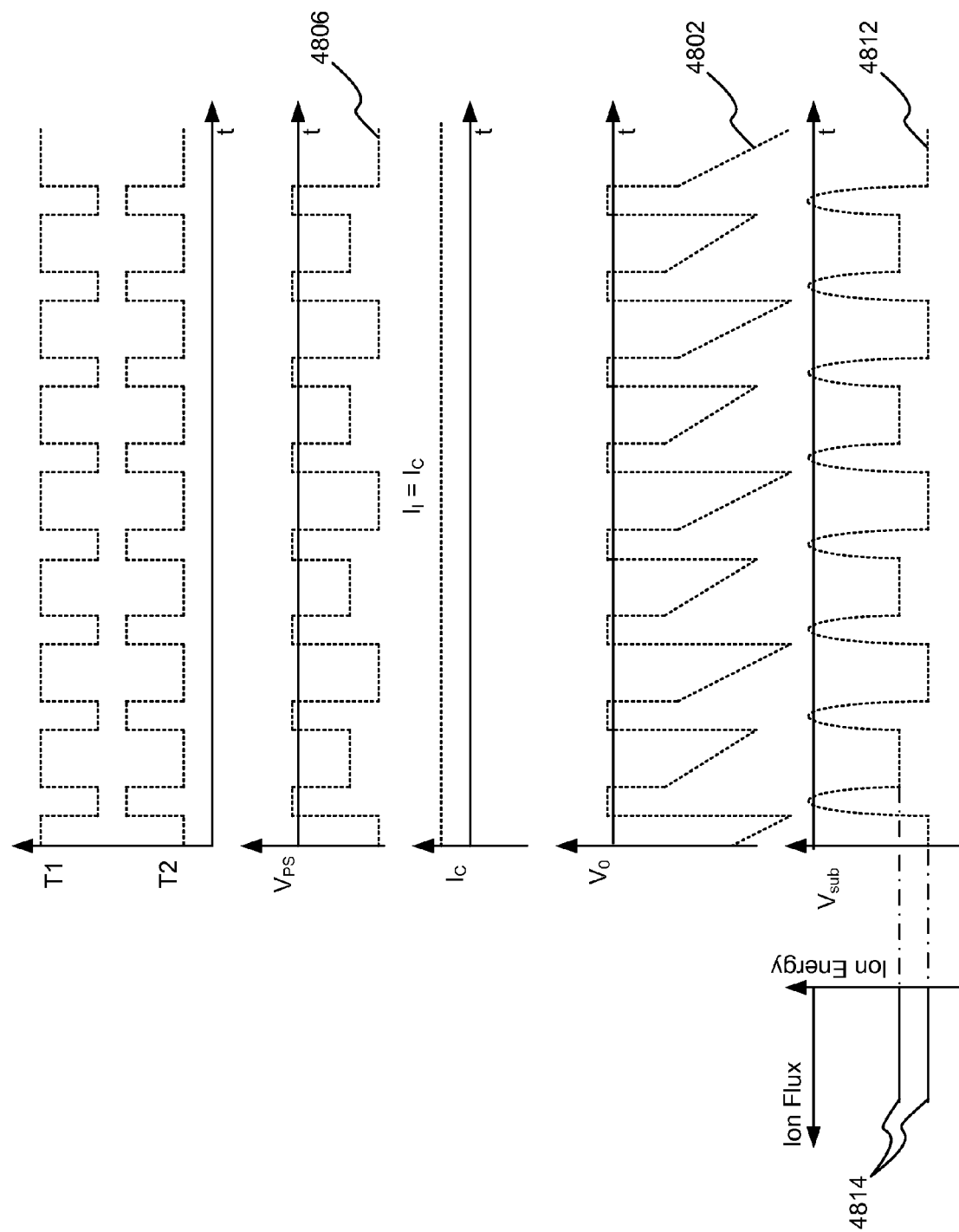
FIG. 48 illustrates one pattern of the power supply voltage, $V_{PS}$, that can be used to achieve more than one ion energy level where each ion energy level has a narrow IEDF width.

FIG. 48 illustrates one pattern of the power supply voltage that can be used to achieve more than one ion energy level where each ion energy level has a narrow IEDF 4814 width. A magnitude of the power supply voltage 4806 alternates each cycle. This results in an alternating $\Delta V$ and peak-to-peak voltage for each cycle of the modified periodic voltage function 4802. The substrate voltage 4812 in turn has two substantially constant voltages that alternate between pulses of the substrate voltage. This results in two different ion energies each having a narrow IEDF 4814 width.

Figure 49:
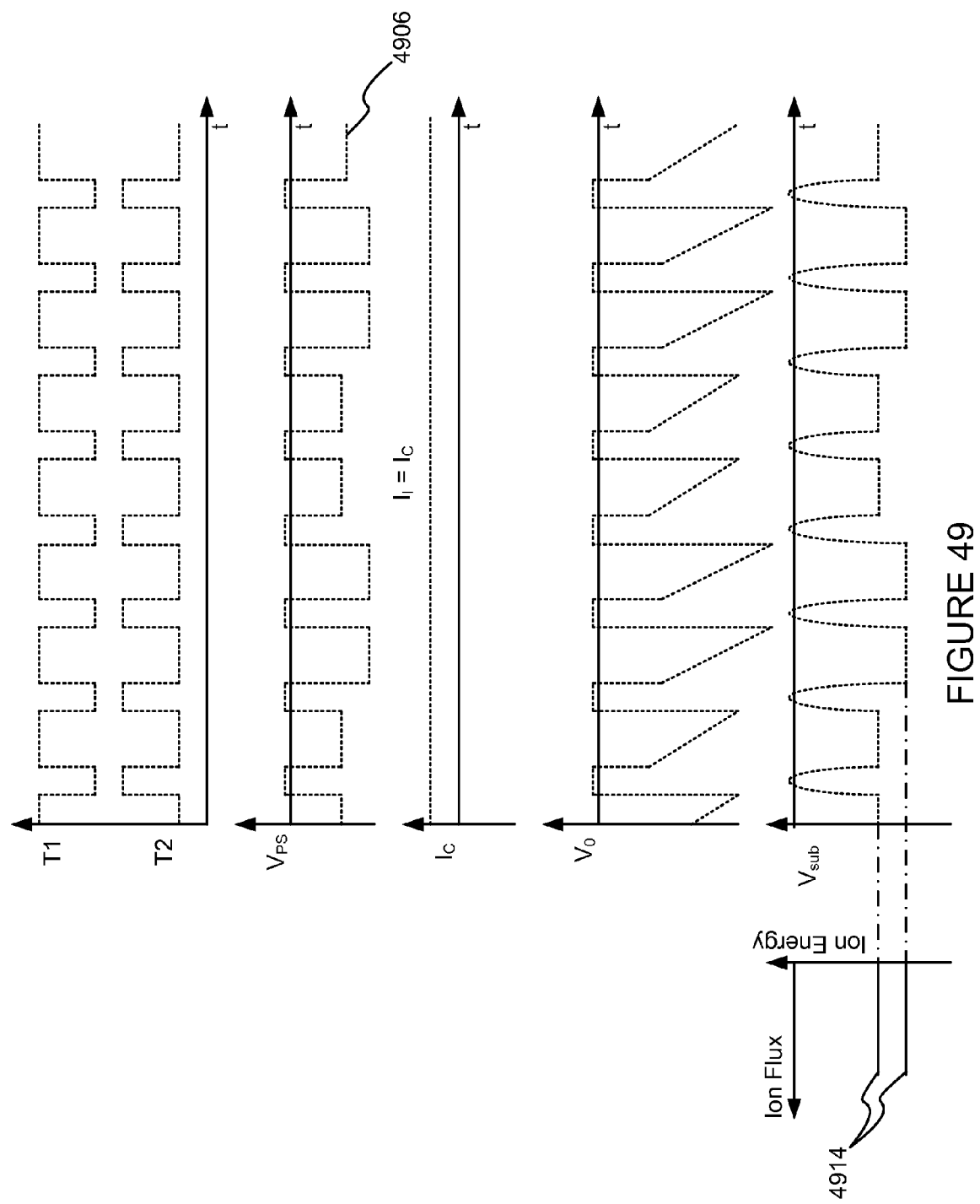
FIG. 49 illustrates another pattern of the power supply voltage, $V_{PS}$, that can be used to achieve more than one ion energy level where each ion energy level has a narrow IEDF width.

FIG. 49 illustrates another pattern of the power supply voltage that can be used to achieve more than one ion energy level where each ion energy level has a narrow IEDF 4914 width. Here, the power supply voltage 4906 alternates between two different magnitudes but does so for two cycles at a time before alternating. As seen, the average ion energies are the same as if $V_{PS}$ 4906 were alternated every cycle. This shows just one example of how various other patterns of the $V_{PS}$ 4906 can be used to achieve the same ion energies.

Figure 50:
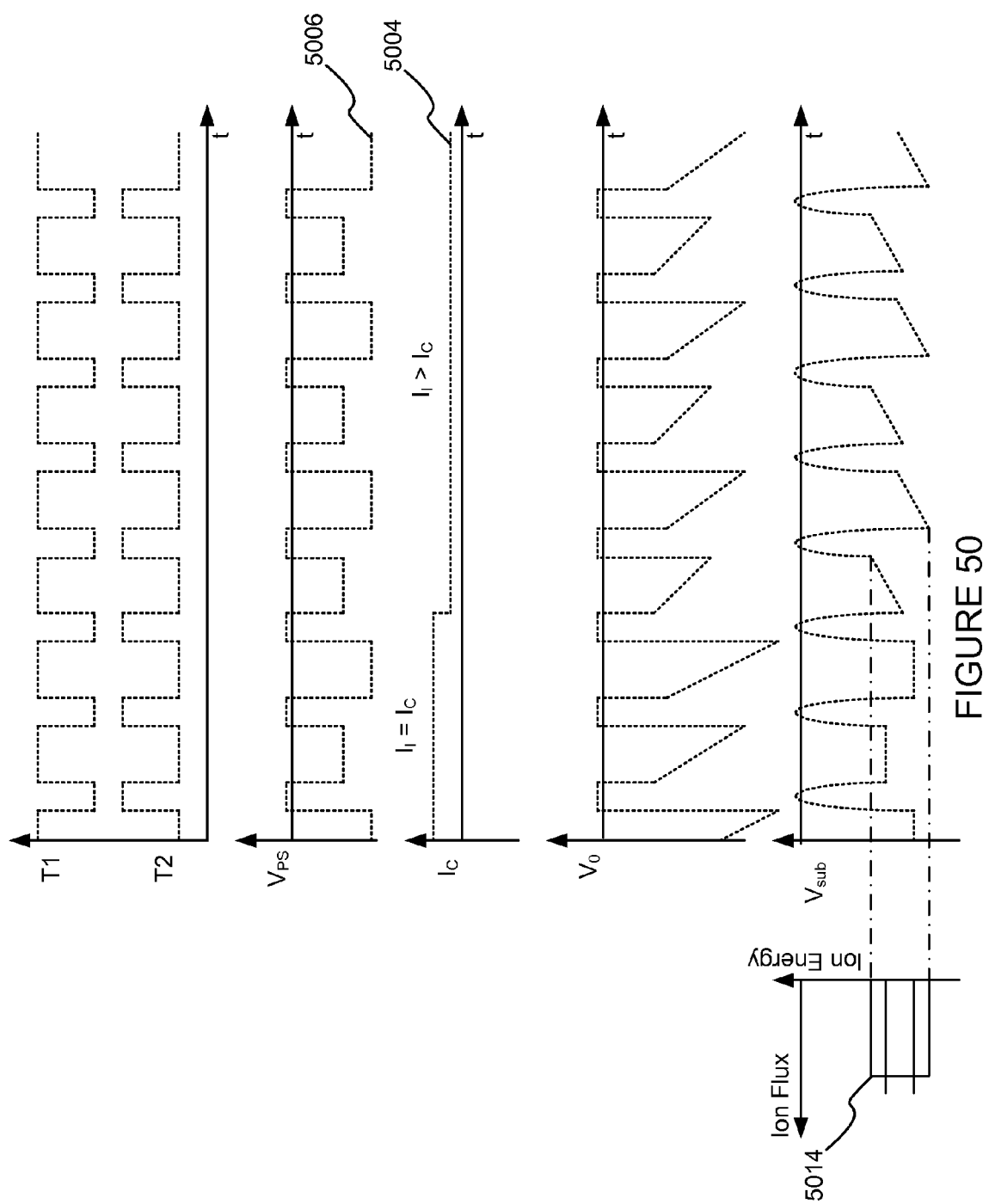
FIG. 50 illustrates one combination of power supply voltages, $V_{PS}$, and ion current compensation, $I_C$, that can be used to create a defined IEDF.

FIG. 50 illustrates one combination of power supply voltages, $V_{PS}$, 5006 and ion current compensation, Ic, 5004 that can be used to create a defined IEDF 5014. Here, alternating power supply voltages 5006 result in two different ion energies. Additionally, by adjusting the ion current compensation 5004 away from the ion current, $I_f$, the IEDF 5014 width for each ion energy can be expanded. If the ion energies are close enough, as they are in the illustrated embodiment, then the IEDF 5014 for both ion energies will overlap resulting in one large IEDF 5014. Other variations are also possible, but this example is meant to show how combinations of adjustments to the $V_{PS}$ 5006 and the $I_C$ 5004 can be used to achieve defined ion energies and defined IEDFs 5014.

Figure 17A:
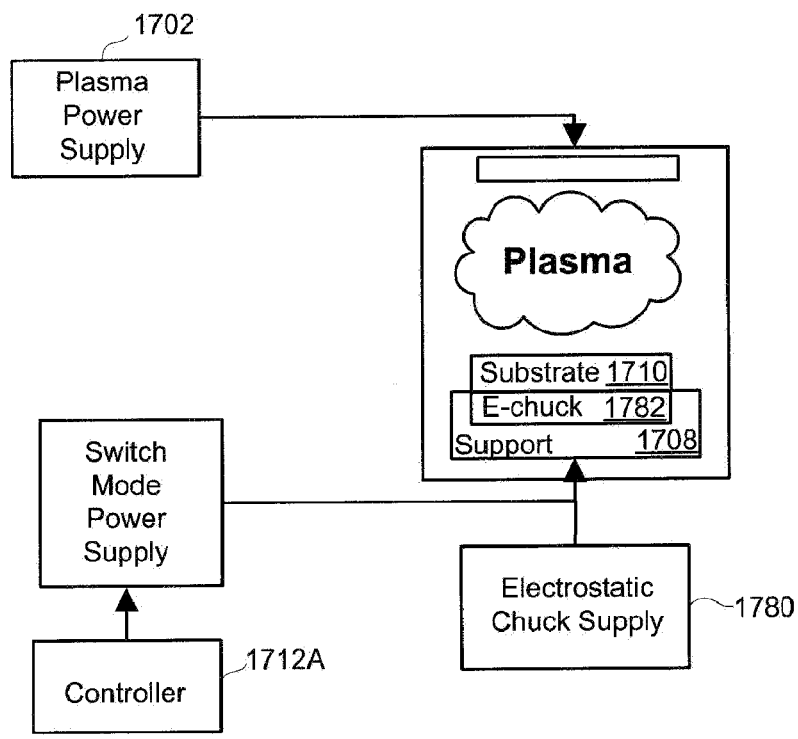
FIGS. 17A and 17B are block diagrams depicting other embodiments of the present invention.
Figure 17B:
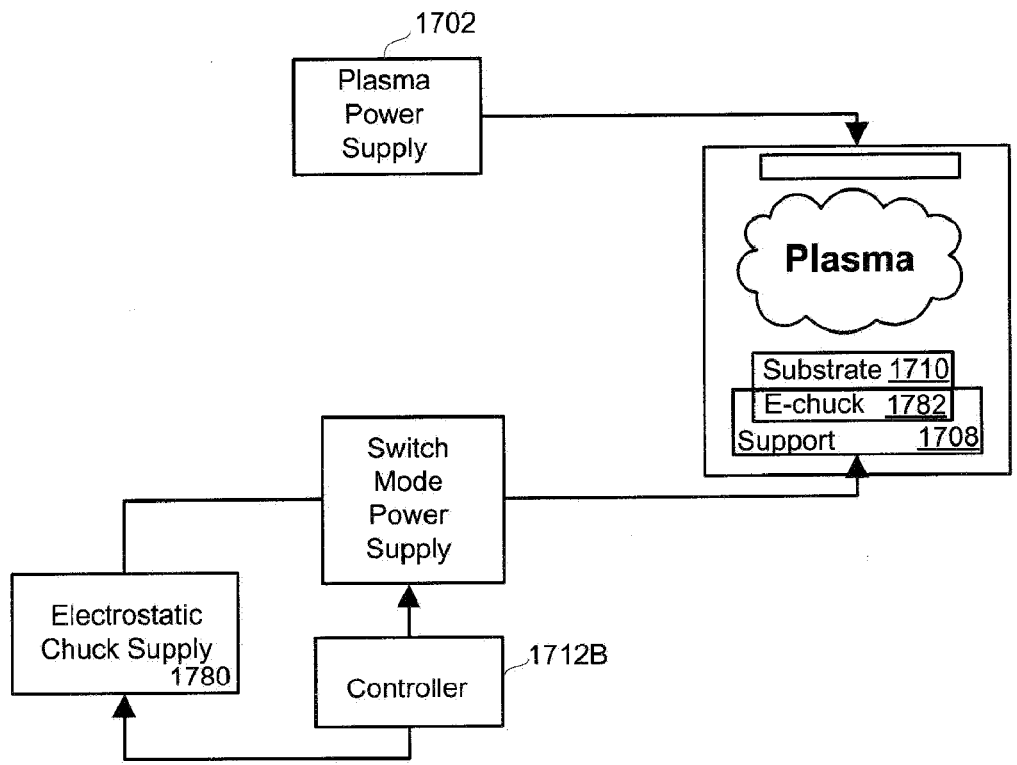

Referring next to FIGS. 17A and 17B, shown are block diagrams depicting other embodiments of the present invention. As shown, the substrate support 1708 in these embodiments includes an electrostatic chuck 1782, and an electrostatic chuck supply 1780 is utilized to apply power to the electrostatic chuck 1782. In some variations, as depicted in FIG. 17A, the electrostatic chuck supply 1780 is positioned to apply power directly to the substrate support 1708, and in other variations, the electrostatic chuck supply 1780 is positioned to apply power in connection with the switch mode power supply. It should be noted that serial chucking can be carried by either a separate supply or by use of the controller to effect a net DC chucking function. In this DC-coupled (e.g., no blocking capacitor), series chucking function, the undesired interference with other RF sources can be minimized.

Figure 18:
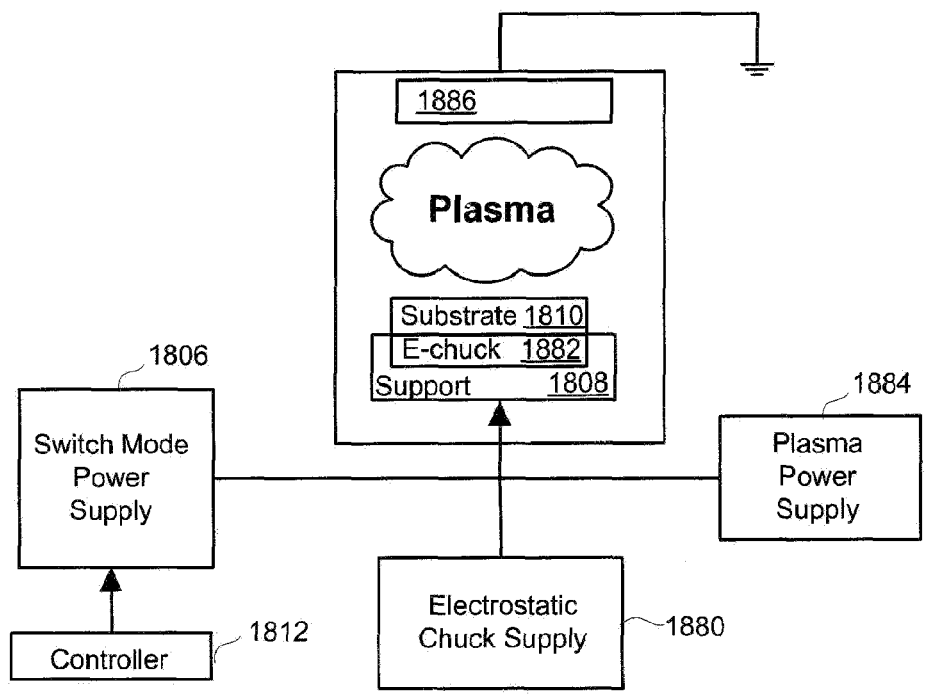
FIG. 18 is a block diagram depicting yet another embodiment of the present invention.

Shown in FIG. 18 is a block diagram depicting yet another embodiment of the present invention in which a plasma power supply 1884 that generally functions to generate plasma density is also configured to drive the substrate support 1808 alongside the switch mode power supply 1806 and electrostatic chuck supply 1880. In this implementation, each of the plasma power supply 1884, the electrostatic chuck supply 1880, and the switch mode power supply 1806 may reside in separate assemblies, or two or more of the supplies 1806, 1880, 1884 may be architected to reside in the same physical assembly. Beneficially, the embodiment depicted in FIG. 18 enables a top electrode 1886 (e.g., shower head) to be electrically grounded so as to obtain electrical symmetry and reduced level of damage due to fewer arcing events.

Figure 19:
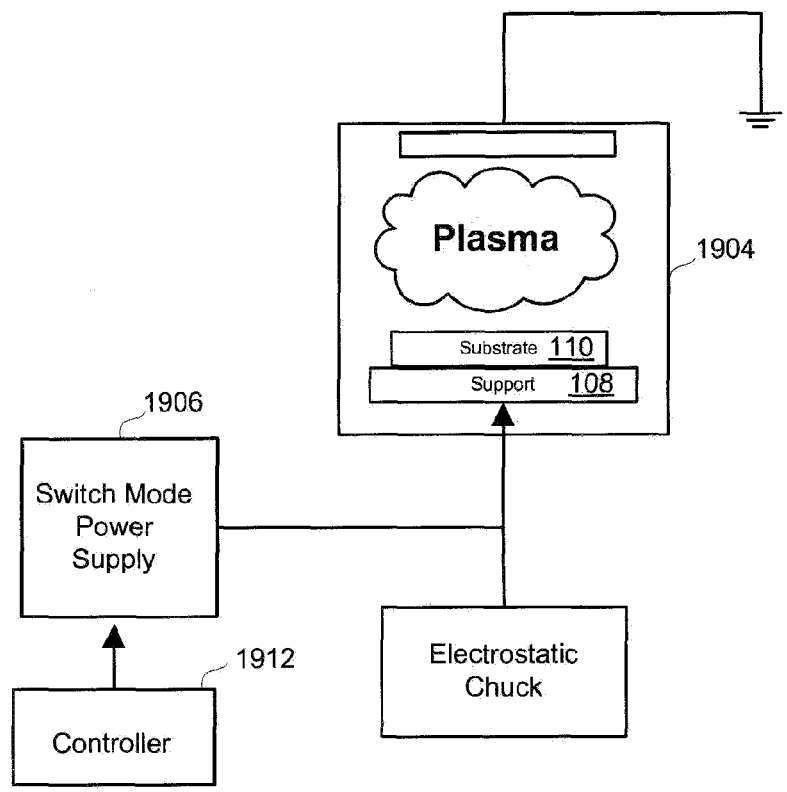
FIG. 19 is a block diagram depicting still another embodiment of the present invention.

Referring to FIG. 19, shown is a block diagram depicting still another embodiment of the present invention. As depicted, the switch mode power supply 1906 in this embodiment is configured to apply power to the substrate support and the chamber 1904 so as to both bias the substrate and ignite (and sustain) the plasma without the need for an additional plasma power supply (e.g., without the plasma power supply 102, 202, 1202, 1702, 1884). For example, the switch-mode power supply 1806 may be operated at a duty cycle that is sufficient to ignite and sustain the plasma while providing a bias to the substrate support.

Figure 20:
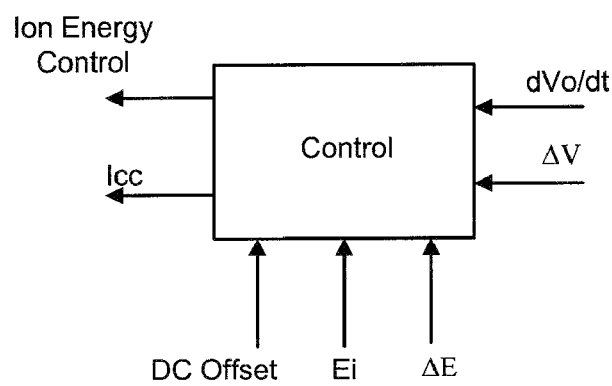
FIG. 20 is a block diagram input parameters and control outputs that may be utilized in connection with the embodiments described with reference to FIGS. 1-19.

Referring next to FIG. 20, it is a block diagram depicting input parameters and control outputs of a control portion that may be utilized in connection with the embodiments described with reference to FIGS. 1-19. The depiction of the control portion is intended to provide a simplified depiction of exemplary control inputs and outputs that may be utilized in connection with the embodiments discussed herein—it is not intended to a be hardware diagram. In actual implementation, the depicted control portion may be distributed among several discrete components that may be realized by hardware, software, firmware, or a combination thereof.

With reference to the embodiments previously discussed herein, the controller depicted in FIG. 20 may provide the functionality of one or more of the controller 112 described with reference to FIG. 1; the controller 212 and ion energy control 220 components described with reference to FIG. 2; the controller 812 and ion energy control portion 820 described with reference to FIG. 8; the ion current compensation component 1260 described with reference to FIG. 12; the current controller 1362 described with reference to FIG. 13; the Icc control depicted in FIG. 16, controllers 1712A, 1712B depicted in FIGS. 17A and 17B, respectively; and controllers 1812, 1912 depicted in FIGS. 18 and 19, respectively.

As shown, the parameters that may be utilized as inputs to the control portion include $dV_o/dt$ and $\Delta V$, which are described in more detail with reference to FIGS. 13 and 14. As discussed, $dV_o/dt$ may be utilized to in connection with an ion-energy-distribution-spread input $\Delta E$ to provide a control signal Icc, which controls a width of the ion energy distribution spread as described with reference to FIGS. 12, 13, 14, 15A-C, and FIG. 16. In addition, an ion energy control input (Ei) in connection with optional feedback $\Delta V$ may be utilized to generate an ion energy control signal (e.g., that affects Vbus depicted in FIG. 3) to effectuate a desired (or defined) ion energy distribution as described in more detail with reference to FIGS. 1-11. And another parameter that may be utilized in connection with many e-chucking embodiments is a DC offset input, which provides electrostatic force to hold the wafer to the chuck for efficient thermal control.

Figure 21:
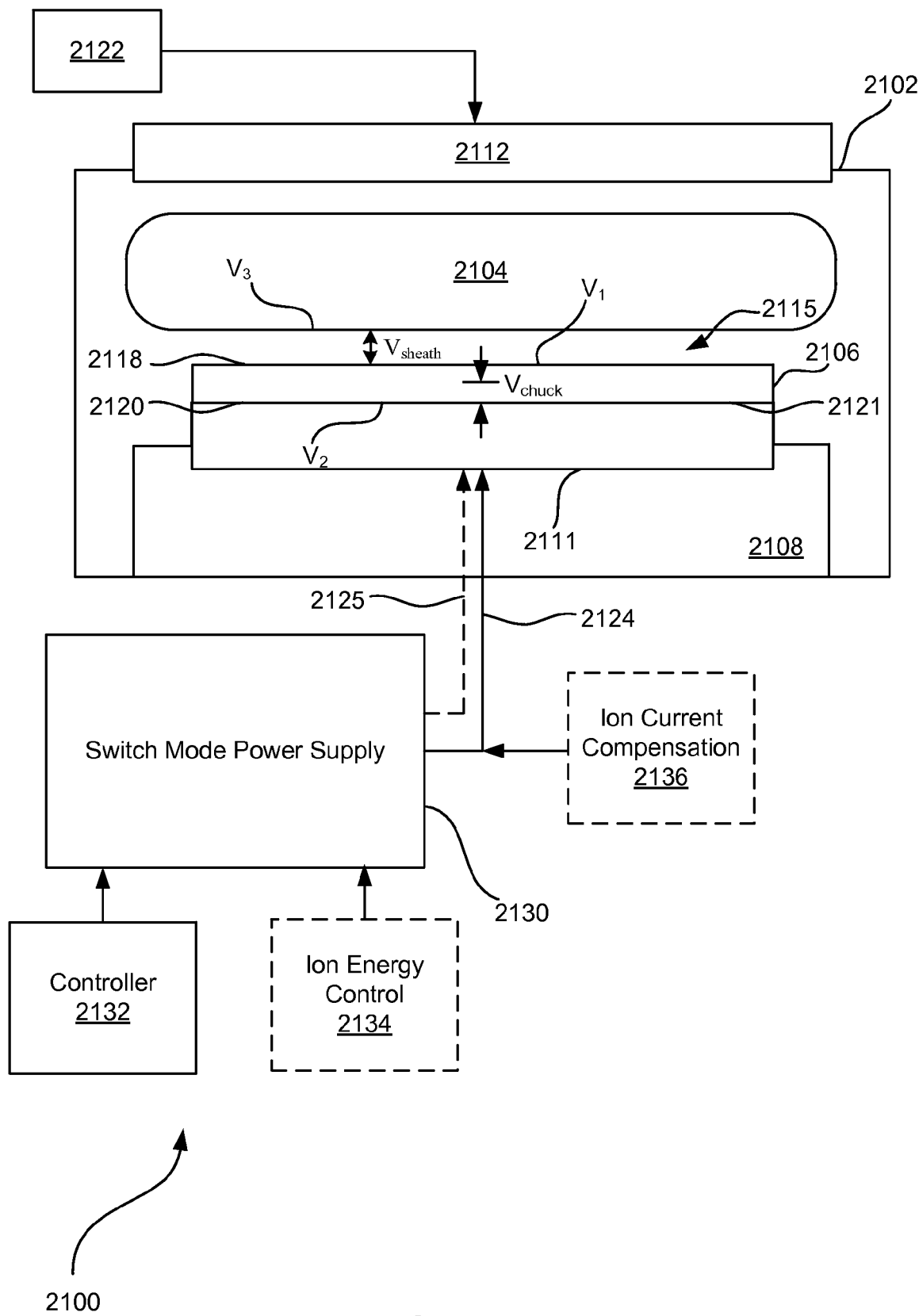
FIG. 21 is a block diagram depicting yet another embodiment of the present invention.

FIG. 21 illustrates a plasma processing system 2100 according to an embodiment of this disclosure. The system 2100 includes a plasma processing chamber 2102 enclosing a plasma 2104 for etching a top surface 2118 of a substrate 2106 (and other plasma processes). The plasma is generated by a plasma source 2112 (e.g., in-situ or remote or projected) powered by a plasma power supply 2122. A plasma sheath voltage $V_{sheath}$ measured between the plasma 2104 and the top surface 2118 of the substrate 2106 accelerates ions from the plasma 2104 across a plasma sheath 2115, causing the accelerated ions to impact a top surface 2118 of a substrate 2106 and etch the substrate 2106 (or portions of the substrate 2106 not protected by photoresist). The plasma 2104 is at a plasma potential $V_3$ relative to ground (e.g., the plasma processing chamber 2102 walls). The substrate 2106 has a bottom surface 2120 that is electrostatically held to a support 2108 via an electrostatic chuck 2111 and a chucking potential $V_{chuck}$ between a top surface 2121 of the electrostatic chuck 2111 and the substrate 2106. The substrate 2106 is dielectric and therefore can have a first potential $V_1$ at the top surface 2118 and a second potential $V_2$ at the bottom surface 2120. The top surface of the electrostatic chuck 2121 is in contact with the bottom surface 2120 of the substrate, and thus these two surfaces 2120, 2121 are at the same potential, $V_2$. The first potential $V_1$, the chucking potential $V_{chuck}$, and the second potential $V_2$, are controlled via an AC waveform with a DC bias or offset generated by a switch mode power supply 2130 and provided to the electrostatic chuck 2111 via a first conductor 2124. Optionally, the AC waveform is provided via the first conductor 2124, and the DC waveform is provided via an optional second conductor 2125. The AC and DC output of the switch mode power supply 2130 can be controlled via a controller 2132, which is also configured to control various aspects of the switch mode power supply 2130.

Ion energy and ion energy distribution are a function of the first potential $V_1$. The switch mode power supply 2130 provides an AC waveform tailored to effect a desired first potential $V_1$ known to generate a desired (or defined) ion energy and ion energy distribution. The AC waveform can be RF and have a non-sinusoidal waveform such as that illustrated in FIGS. 5, 6, 11, 14, 15a, 15b, and 15c. The first potential $V_1$ can be proportional to the change in voltage ΔV illustrated in FIG. 14. The first potential $V_1$ is also equal to the plasma voltage $V_3$ minus the plasma sheath voltage $V_{sheath}$. But since the plasma voltage $V_3$ is often small (e.g., less than 20 V) compared to the plasma sheath voltage $V_{sheath}$ (e.g., 50V-2000 V), the first potential $V_1$ and the plasma sheath voltage $V_{sheath}$ are approximately equal and for purposes of implementation can be treated as being equal. Thus, since the plasma sheath voltage $V_{sheath}$ dictates ion energies, the first potential $V_1$ is proportional to ion energy distribution. By maintaining a constant first potential $V_1$, the plasma sheath voltage $V_{sheath}$ is constant, and thus substantially all ions are accelerated via the same energy, and hence a narrow ion energy distribution is achieved. The plasma voltage $V_3$ results from energy imparted to the plasma 2104 via the plasma source 2112.

The first potential $V_1$ at the top surface 2118 of the substrate 2106 is formed via a combination of capacitive charging from the electrostatic chuck 2111 and charge buildup from electrons and ions passing through the sheath 2115. The AC waveform from the switch mode power supply 2130 is tailored to offset the effects of ion and electron transfer through the sheath 2115 and the resulting charge buildup at the top surface 2118 of the substrate 2106 such that the first potential $V_1$ remains substantially constant.

The chucking force that holds the substrate 2106 to the electrostatic chuck 2111 is a function of the chucking potential $V_{chuck}$. The switch mode power supply 2130 provides a DC bias, or DC offset, to the AC waveform, so that the second potential $V_2$ is at a different potential than the first potential $V_1$. This potential difference causes the chucking voltage $V_{chuck}$. The chucking voltage $V_{chuck}$ can be measured from the top surface 2221 of the electrostatic chuck 2111 to a reference layer inside the substrate 2106, where the reference layer includes any elevation inside the substrate except a bottom surface 2120 of the substrate 2106 (the exact location within the substrate 2106 of the reference layer can vary). Thus, chucking is controlled by and is proportional to the second potential $V_2$.

In an embodiment, the second potential $V_2$ is equal to the DC offset of the switch mode power supply 2130 modified by the AC waveform (in other words an AC waveform with a DC offset where the DC offset is greater than a peak-to-peak voltage of the AC waveform). The DC offset may be substantially larger than the AC waveform, such that the DC component of the switch mode power supply 2130 output dominates the second potential $V_2$ and the AC component can be neglected or ignored.

The potential within the substrate 2106 varies between the first and second potentials $V_1$, $V_2$. The chucking potential $V_{chuck}$ can be positive or negative (e.g., $V_1 > V_2$ or $V_1 < V_2$) since the coulombic attractive force between the substrate 2106 and the electrostatic chuck 2111 exists regardless of the chucking potential $V_{chuck}$ polarity.

The switch mode power supply 2130 in conjunction with the controller 2132 can monitor various voltages deterministically and without sensors. In particular, the ion energy (e.g., mean energy and ion energy distribution) is deterministically monitored based on parameters of the AC waveform (e.g., slope and step). For instance, the plasma voltage $V_3$, ion energy, and ion energy distribution are proportional to parameters of the AC waveform produced by the switch mode power supply 2130. In particular the ΔV of the falling edge of the AC waveform (see for example FIG. 14), is proportional to the first potential $V_1$, and thus to the ion energy. By keeping the first potential $V_1$ constant, the ion energy distribution can be kept narrow.

Although the first potential $V_1$ cannot be directly measured and the correlation between the switch mode power supply output and the first voltage $V_1$ may vary based on the capacitance of the substrate 2106 and processing parameters, a constant of proportionality between ΔV and the first potential $V_1$ can be empirically determined after a short processing time has elapsed. For instance, where the falling edge ΔV of the AC waveform is 50 V, and the constant of proportionality is empirically found to be 2 for the given substrate and process, the first potential $V_1$ can be expected to be 100 V. A proportionality between the step voltage, ΔV, and the first potential $V_1$ (and thus also ion energy, eV) is described by Equation 4. Thus, the first potential $V_1$, along with ion energy, and ion energy distribution can be determined based on knowledge of the AC waveform of the switch mode power supply without any sensors inside the plasma processing chamber 2102. Additionally, the switch mode power supply 2130 in conjunction with the controller 2132 can monitor when and if chucking is taking place (e.g., whether the substrate 2106 is being held to the electrostatic chuck 2111 via the chucking potential $V_{chuck}$).

Dechucking is performed by eliminating or decreasing the chucking potential $V_{chuck}$. This can be done by setting the second potential $V_2$ equal to the first potential $V_1$. In other words, the DC offset and the AC waveform can be adjusted in order to cause the chucking voltage $V_{chuck}$ to approach 0 V. Compared to conventional dechucking methods, the system 2100 achieves faster dechucking and thus greater throughput since both the DC offset and the AC waveform can be adjusted to achieve dechucking. Also, when the DC and AC power supplies are in the switch mode power supply 2130, their circuitry is more unified, closer together, can be controlled via a single controller 2132 (as compared to typical parallel arrangements of DC and AC power supplies), and change output faster. The speed of dechucking enabled by the embodiments herein disclosed also enables dechucking after the plasma 2104 is extinguished, or at least after power from the plasma source 2112 has been turned off.

The plasma source 2112 can take a variety of forms. For instance, in an embodiment, the plasma source 2112 includes an electrode inside the plasma processing chamber 2102 that establishes an RF field within the chamber 2102 that both ignites and sustains the plasma 2104. In another embodiment, the plasma source 2112 includes a remote projected plasma source that remotely generates an ionizing electromagnetic field, projects or extends the ionizing electromagnetic field into the processing chamber 2102, and both ignites and sustains the plasma 2104 within the plasma processing chamber using the ionizing electromagnetic field. Yet, the remote projected plasma source also includes a field transfer portion (e.g., a conductive tube) that the ionizing electromagnetic field passes through en route to the plasma processing chamber 2102, during which time the ionizing electromagnetic field is attenuated such that the field strength within the plasma processing chamber 2102 is only a tenth or a hundred or a thousandth or an even smaller portion of the field strength when the field is first generated in the remote projected plasma source. The plasma source 2112 is not drawn to scale.

The switch mode power supply 2130 can float and thus can be biased at any DC offset by a DC power source (not illustrated) connected in series between ground and the switch mode power supply 2130. The switch mode power supply 2130 can provide an AC waveform with a DC offset either via AC and DC power sources internal to the switch mode power supply 2130 (see for example FIGS. 22, 23, 26), or via an AC power source internal to the switch mode power supply 2130 and a DC power supply external to the switch mode power supply 2130 (see for example FIGS. 24, 27). In an embodiment, the switch mode power supply 2130 can be grounded and be series coupled to a floating DC power source coupled in series between the switch mode power supply 2130 and the electrostatic chuck 2111.

The controller 2132 can control an AC and DC output of the switch mode power supply when the switch mode power supply 2130 includes both an AC and DC power source. When the switch mode power supply 2130 is connected in series with a DC power source, the controller 2132 may only control the AC output of the switch mode power supply 2130. In an alternative embodiment, the controller 2130 can control both a DC power supply coupled to the switch mode power supply 2130, and the switch mode power supply 2130. One skilled in the art will recognize that while a single controller 2132 is illustrated, other controllers can also be implemented to control the AC waveform and DC offset provided to the electrostatic chuck 2111.

The electrostatic chuck 2111 can be a dielectric (e.g., ceramic) and thus substantially block passage of DC voltages, or it can be a semiconductive material such as a doped ceramic. In either case, the electrostatic chuck 2111 can have a second voltage $V_2$ on a top surface 2121 of the electrostatic chuck 2111 that capacitively couples voltage to a top surface 2118 of the substrate 2106 (usually a dielectric) to form the first voltage $V_1$.

The plasma 2104 shape and size are not necessarily drawn to scale. For instance, an edge of the plasma 2104 can be defined by a certain plasma density in which case the illustrated plasma 2104 is not drawn with any particular plasma density in mind. Similarly, at least some plasma density fills the entire plasma processing chamber 2102 despite the illustrated plasma 2104 shape. The illustrated plasma 2104 shape is intended primarily to show the sheath 2115, which does have a substantially smaller plasma density than the plasma 2104.

Figure 22:
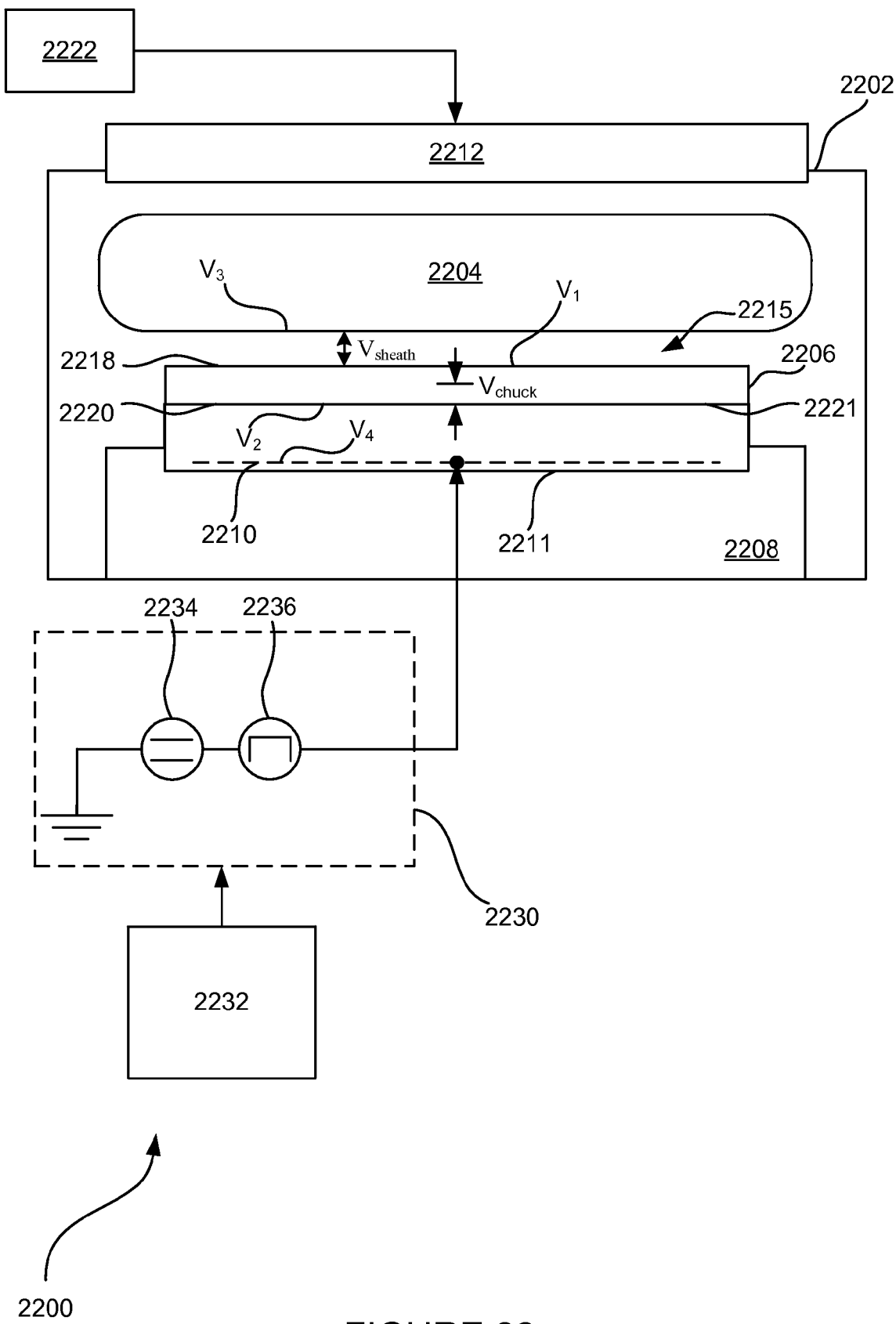
FIG. 22 is a block diagram depicting yet another embodiment of the present invention.

FIG. 22 illustrates another embodiment of a plasma processing system 2200. In the illustrated embodiment, the switch mode power supply 2230 includes a DC power source 2234 and an AC power source 2236 connected in series. Controller 2232 is configured to control an AC waveform with a DC offset output of the switch mode power supply 2230 by controlling both the AC power source 2236 waveform and the DC power source 2234 bias or offset. This embodiment also includes an electrostatic chuck 2211 having a grid or mesh electrode 2210 embedded in the chuck 2211. The switch mode power supply 2230 provides both an AC and DC bias to the grid electrode 2210. The DC bias along with the AC component, which is substantially smaller than the DC bias and can thus be neglected, establishes a third potential $V_4$ on the grid electrode 2210. When the third potential $V_4$ is different than a potential at a reference layer anywhere within the substrate 2206 (excluding the bottom surface 2220 of the substrate 2206), a chucking potential $V_{chuck}$ and a coulombic chucking force are established which hold the substrate 2206 to the electrostatic chuck 2211. The reference layer is an imaginary plane parallel to the grid electrode 2210. The AC waveform capacitively couples from the grid electrode 2210 through a portion of the electrostatic chuck 2211, and through the substrate 2206 to control the first potential $V_1$ on a top surface 2218 of the substrate 2206. Since a plasma potential $V_3$ is negligible relative to a plasma sheath voltage $V_{sheath}$, the first potential $V_1$ and the plasma sheath voltage $V_{sheath}$ are approximately equal, and for practical purposes are considered equal. Therefore, the first potential $V_1$ equals the potential used to accelerate ions through the sheath 2215.

In an embodiment, the electrostatic chuck 2211 can be doped so as to be conductive enough that any potential difference through the body of the chuck 2211 is negligible, and thus the grid or mesh electrode 2210 can be at substantially the same voltage as the second potential $V_2$.

The grid electrode 2210 can be any conductive planar device embedded in the electrostatic chuck 2211, parallel to the substrate 2206, and configured to be biased by the switch mode power supply 2230 and to establish a chucking potential $V_{chuck}$. Although the grid electrode 2210 is illustrated as being embedded in a lower portion of the electrostatic chuck 2211, the grid electrode 2210 can be located closer or further from the substrate 2206. The grid electrode 2210 also does not have to have a grid pattern. In an embodiment, the grid electrode 2210 can be a solid electrode or have a non-solid structure with a non-grid shape (e.g., a checkerboard pattern). In an embodiment, the electrostatic chuck 2211 is a ceramic or other dielectric and thus the third potential $V_4$ on the grid electrode 2210 is not equal to the first potential $V_1$ on a top surface 2221 of the electrostatic chuck 2211. In another embodiment, the electrostatic chuck 2211 is a doped ceramic that is slightly conductive and thus the third potential $V_4$ on the grid electrode 2210 can be equal to the second potential $V_2$ on the top surface 2221 of the electrostatic chuck 2211.

The switch mode power supply 2230 generates an AC output that can be non-sinusoidal. The switch mode power supply 2230 is able to operate the DC and AC sources 2234, 2236 in series because the DC power source 2234 is AC-conductive and the AC power source 2236 is DC-conductive. Exemplary AC power sources that are not DC-conductive are certain linear amplifiers which can be damaged when provided with DC voltage or current. The use of AC-conductive and DC-conductive power sources reduces the number of components used in the switch mode power supply 2230. For instance, if the DC power source 2234 is AC-blocking, then an AC-bypass or DC-blocking component (e.g., a capacitor) may have to be arranged in parallel with the DC power source 2234. If the AC power source 2236 is DC-blocking, then a DC-bypass or AC-blocking component (e.g., an inductor) may have to be arranged in parallel with the AC power source 2236.

In this embodiment, the AC power source 2238 is generally configured to apply a voltage bias to the electrostatic chuck 2211 in a controllable manner so as to effectuate a desired (or defined) ion energy distribution for the ions bombarding the top surface 2218 of the substrate 2206. More specifically, the AC power source 2236 is configured to effectuate the desired (or defined) ion energy distribution by applying one or more particular waveforms at particular power levels to the grid electrode 2210. And more particularly, the AC power source 2236 applies particular power levels to effectuate particular ion energies, and applies the particular power levels using one or more voltage waveforms defined by waveform data stored in a waveform memory (not illustrated). As a consequence, one or more particular ion bombardment energies may be selected to carry out controlled etching of the substrate 2206 (or other plasma-assisted processes). In one embodiment, the AC power source 2236 can make use of a switched mode configuration (see for example FIGS. 25-27). The switch mode power supply 2230, and particularly the AC power source 2236, can produce an AC waveform as described in various embodiments of this disclosure.

One skilled in the art will recognize that the grid electrode 2210 may not be necessary and that other embodiments can be implemented without the grid electrode 2210. One skilled in the art will also recognize that the grid electrode 2210 is just one example of numerous devices that can be used to establish chucking potential $V_{chuck}$.

Figure 23:
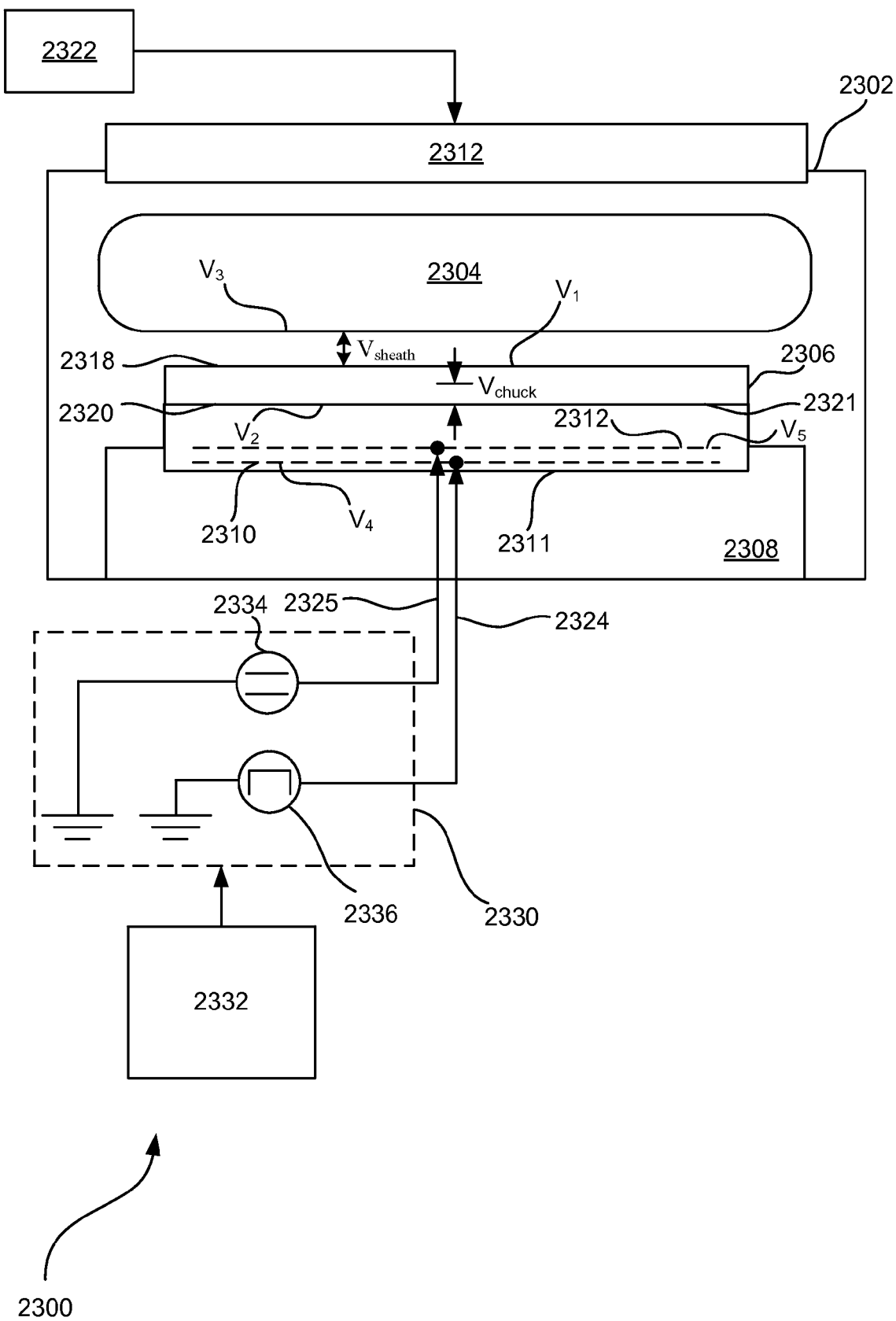
FIG. 23 is a block diagram depicting yet another embodiment of the present invention.

FIG. 23 illustrates another embodiment, of a plasma processing system 2300. The illustrated embodiment includes a switch mode power supply 2330 for providing an AC waveform and a DC bias to an electrostatic chuck 2311. The switch mode power supply 2330 includes a DC power source 2334 and an AC power source 2336, both of which can be grounded. The AC power source 2336 generates an AC waveform that is provided to a first grid or mesh electrode 2310 embedded in the electrostatic chuck 2311 via a first conductor 2324. The AC power source 2336 establishes a potential $V_4$ on the first grid or mesh electrode 2310. The DC power source 2334 generates a DC bias that is provided to a second grid or mesh electrode 2312 embedded in the electrostatic chuck 2311 via a second conductor 2325. The DC power source 2334 establishes a potential $V_5$ on the second grid or mesh electrode 2312. The potentials $V_4$ and $V_5$ can be independently controlled via the AC and DC power sources 2336, 2334, respectively. However, the first and second grid or mesh electrodes 2310, 2312 can also be capacitively coupled and/or there can be DC coupling between the grid or mesh electrodes 2310, 2312 via a portion of the electrostatic chuck 2311. If either AC or DC coupling exists, then the potentials $V_4$ and $V_5$ may be coupled. One skilled in the art will recognize that the first and second grid electrodes 2310, 2312 can be arranged in various locations throughout the electrostatic chuck 2311 including arranging the first grid electrode 2310 closer to the substrate 2306 than the second grid electrode 2312.

Figure 24:
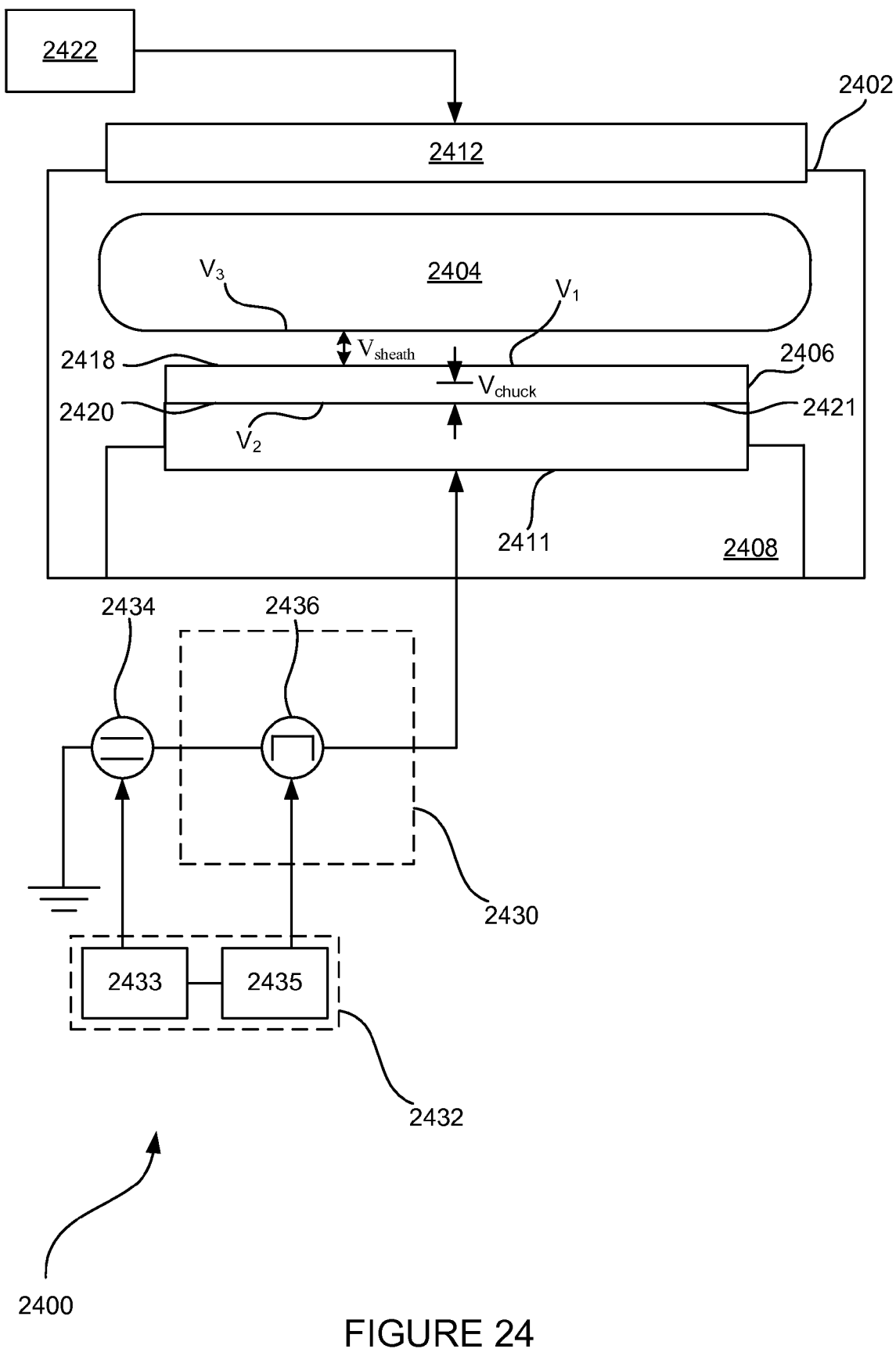
FIG. 24 is a block diagram depicting yet another embodiment of the present invention.

FIG. 24 illustrates another embodiment of a plasma processing system 2400. In this embodiment, a switch mode power supply 2430 provides an AC waveform to an electrostatic chuck 2411, where the switch mode power supply 2430 output is offset by a DC bias provided by a DC power supply 2434. The AC waveform of the switch mode power supply 2430 has a waveform selected by controller 2435 to bombard a substrate 2406 with ions from a plasma 2404 having a narrow ion energy distribution. The AC waveform can be non-sinusoidal (e.g., square wave or pulsed) and can be generated via an AC power source 2436 of the switch mode power supply 2430. Chucking is controlled via the DC offset from the DC power supply 2434, which is controlled by controller 2433. The DC power supply 2434 can be coupled in series between ground and the switch mode power supply 2430. The switch mode power supply 2430 is floating such that its DC bias can be set by the DC power supply 2434.

One skilled in the art will recognize that while the illustrated embodiment shows two independent controllers 2433, 2435, these could be combined into a single functional unit, device, or system such as optional controller 2432. Additionally, controllers 2433 and 2435 can be coupled so as to communicate with each other and share processing resources.

Figure 25:
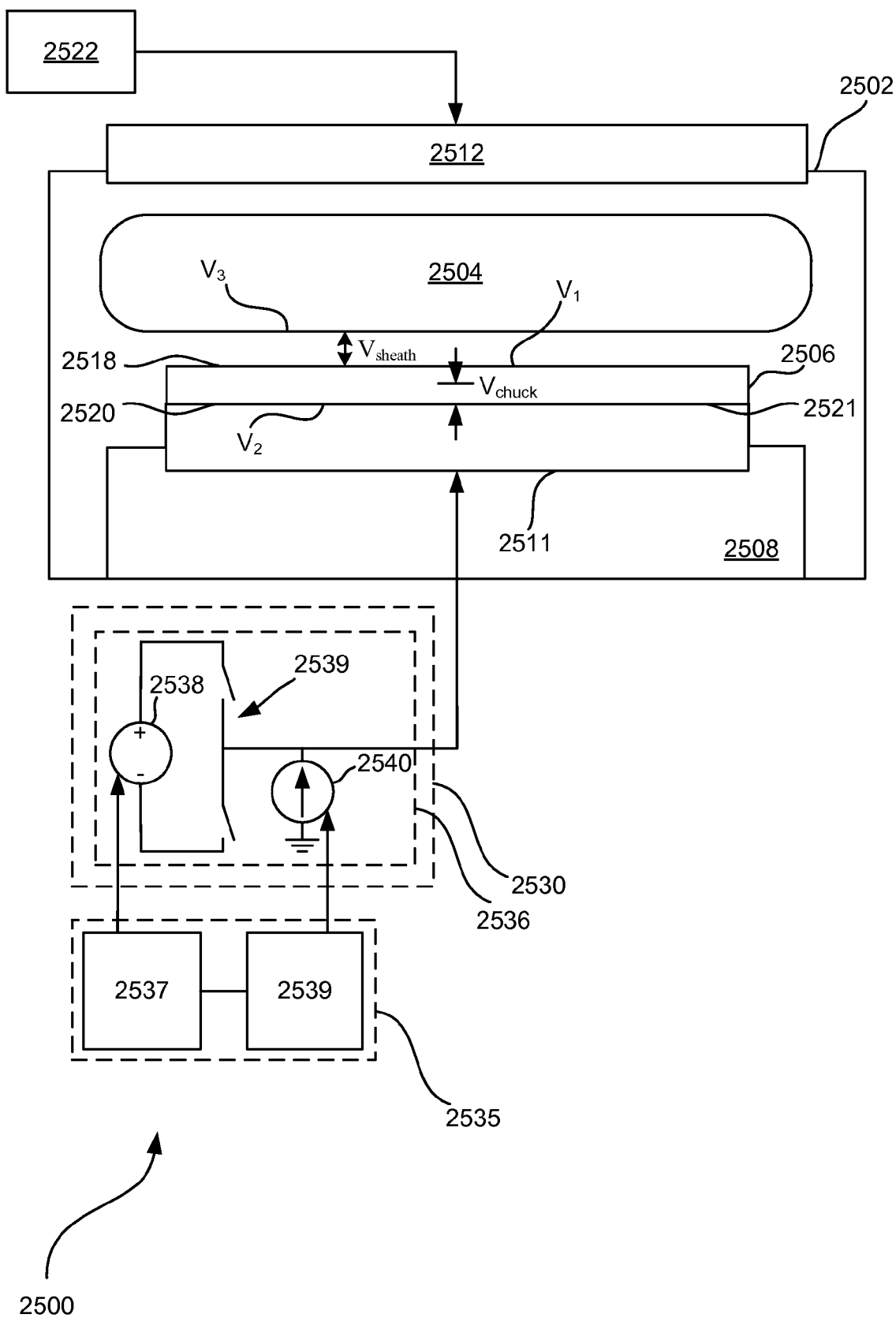
FIG. 25 is a block diagram depicting yet another embodiment of the present invention.

FIG. 25 illustrates a further embodiment of a plasma processing system 2500. The illustrated embodiment includes a switch mode power supply 2530 that produces an AC waveform that can have a DC offset provided by a DC power supply (not illustrated). The switch mode power supply can be controlled via optional controller 2535, which encompasses a voltage and current controller 2537, 2539. The switch mode power supply 2530 can include a controllable voltage source 2538 having a voltage output controlled by the voltage controller 2537, and a controllable current source 2540 having a current output controlled by the current controller 2539. The controllable voltage and current sources 2538, 2540 can be in a parallel arrangement. The controllable current source 2540 is configured to compensate for an ion current between a plasma 2504 and a substrate 2506.

The voltage and current controllers 2537, 2539 can be coupled and in communication with each other. The voltage controller 2537 can also control a switched output 2539 of the controllable voltage source 2538. The switched output 2539 can include two switches in parallel as illustrated, or can include any circuitry that converts an output of the controllable voltage source 2538 into a desired AC waveform (e.g., non-sinusoidal). Via the two switches, a controlled voltage or AC waveform from the controllable voltage source 2538 can be combined with a controlled current output of the controllable current source 2540 to generate an AC waveform output of the switch mode power supply 2530.

The controllable voltage source 2538 is illustrated as having a given polarity, but one skilled in the art will recognize that the opposite polarity is an equivalent to that illustrated. Optionally, the controllable voltage and current sources 2538, 2540 along with the switched output 2539 can be part of an AC power source 2536 and the AC power source 2536 can be arranged in series with a DC power source (not illustrated) that is inside or outside of the switch mode power supply 2530.

Figure 26:
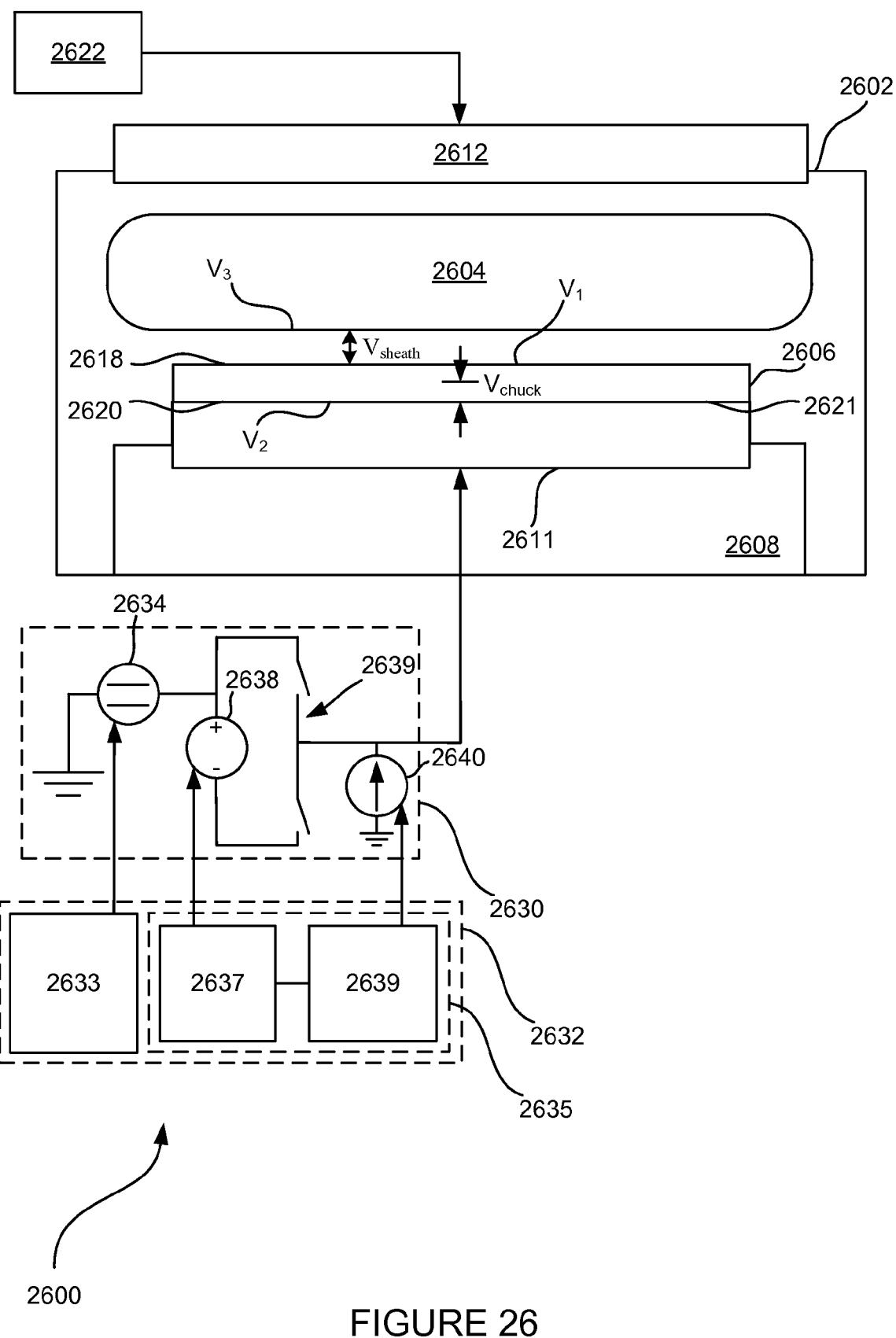
FIG. 26 is a block diagram depicting yet another embodiment of the present invention.

FIG. 26 illustrates yet another embodiment of a plasma processing system 2600. In the illustrated embodiment, a switch mode power supply 2630 provides an AC waveform having a DC offset to an electrostatic chuck 2611. The AC component of the waveform is generated via a parallel combination of a controllable voltage source 2638 and a controllable current source 2640 connected to each other through a switched output 2639. The DC offset is generated by a DC power source 2634 coupled in series between ground and the controllable voltage source 2638. In an embodiment, the DC power source 2634 can be floating rather than grounded. Similarly, the switch mode power supply 2630 can be floating or grounded.

The system 2600 can include one or more controllers for controlling an output of the switch mode power supply 2630. A first controller 2632 can control the output of the switch mode power supply 2630, for instance via a second controller 2633 and a third controller 2635. The second controller 2633 can control a DC offset of the switch mode power supply 2630 as generated by the DC power source 2634. The third controller 2635 can control the AC waveform of the switch mode power supply 2630 by controlling the controllable voltage source 2638 and the controllable current source 2640. In an embodiment, a voltage controller 2637 controls the voltage output of the controllable voltage source 2638 and a current controller 2639 controls a current of the controllable current source 2640. The voltage and current controllers 2637, 2639 can be in communication with each other and can be a part of the third controller 2635.

One skilled in the art will recognize that the embodiments above, describing various configurations of controllers relative to the power sources 2634, 2638, 2640, are not limiting, and that various other configurations can also be implemented without departing from this disclosure. For instance, the third controller 2635 or the voltage controller 2637 can control a switched output 2639 between the controllable voltage source 2638 and the controllable current source 2640. As another example, the second and third controllers 2633, 2635 can be in communication with each other (even though not illustrated as such). It should also be understood that the polarities of the controllable voltage and current sources 2638, 2640 are illustrative only and not meant to be limiting.

The switched output 2639 can operate by alternately switching two parallel switches in order to shape an AC waveform. The switched output 2639 can include any variety of switches including, but not limited to, MOSFET and BJT. In one variation, the DC power source 2634 can be arranged between the controllable current source 2640 and the electrostatic chuck 2611 (in other words, the DC power source 2634 can float), and the switch mode power supply 2630 can be grounded.

Figure 27:
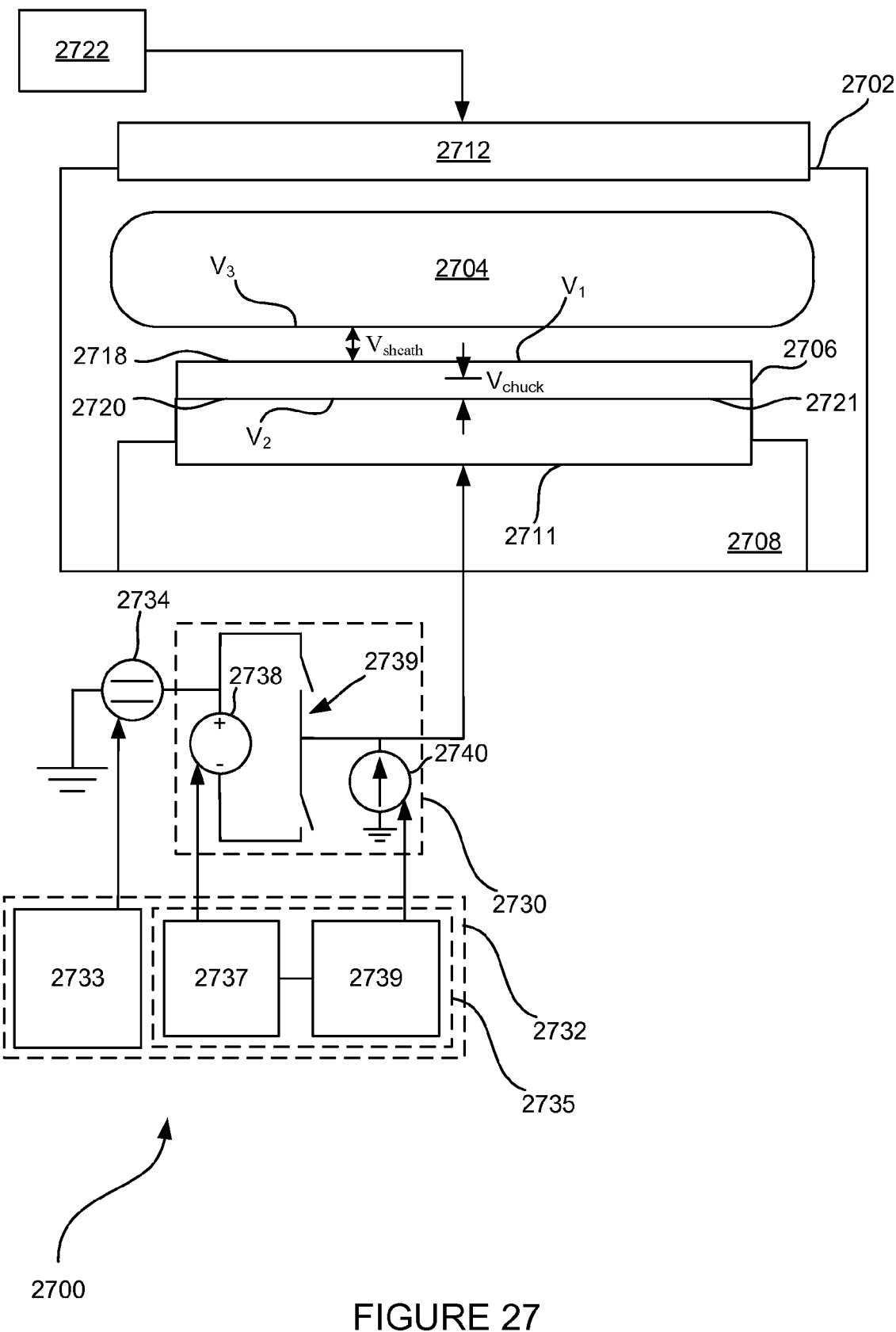
FIG. 27 is a block diagram depicting yet another embodiment of the present invention.

FIG. 27 illustrates another embodiment of a plasma processing system 2700. In this variation, the switch mode power supply 2734 again is grounded, but instead of being incorporated into the switch mode power supply 2730, here the DC power source 2734 is a separate component and provides a DC offset to the entire switch mode power supply 2730 rather than just components within the switch mode power supply 2730.

Figure 28:
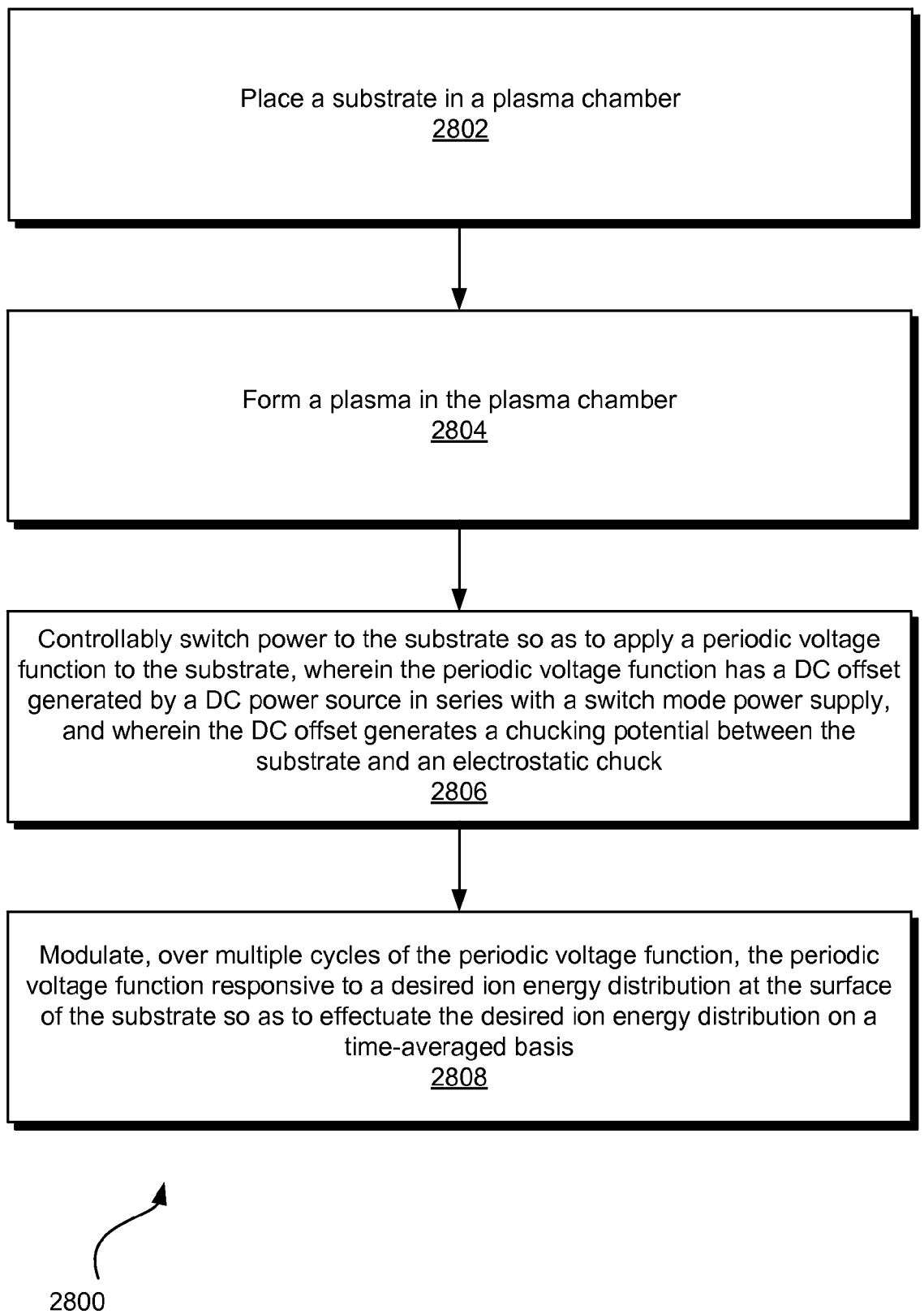
FIG. 28 illustrates a method according to an embodiment of this disclosure.

FIG. 28 illustrates a method 2800 according to an embodiment of this disclosure. The method 2800 includes a place a substrate in a plasma chamber operation 2802. The method 2800 further includes a form a plasma in the plasma chamber operation 2804. Such a plasma can be formed in situ or via a remote projected source. The method 2800 also includes a switch power operation 2806. The switch power operation 2806 involves controllably switching power to the substrate so as to apply a period voltage function to the substrate. The periodic voltage function can be considered a pulsed waveform (e.g., square wave) or an AC waveform and includes a DC offset generated by a DC power source in series with a switch mode power supply. In an embodiment, the DC power source can be incorporated into the switch mode power supply and thus be in series with an AC power source of the switch mode power supply. The DC offset generates a potential difference between a top surface of an electrostatic chuck and a reference layer within the substrate and this potential difference is referred to as the chucking potential. The chucking potential between the electrostatic chuck and the substrate holds the substrate to the electrostatic chuck thus preventing the substrate from moving during processing. The method 2800 further includes a modulate operation 2808 in which the periodic voltage function is modulated over multiple cycles. The modulation is responsive to a desired (or defined) ion energy distribution at the surface of the substrate so as to effectuate the desired (or defined) ion energy distribution on a time-averaged basis.

Figure 29:
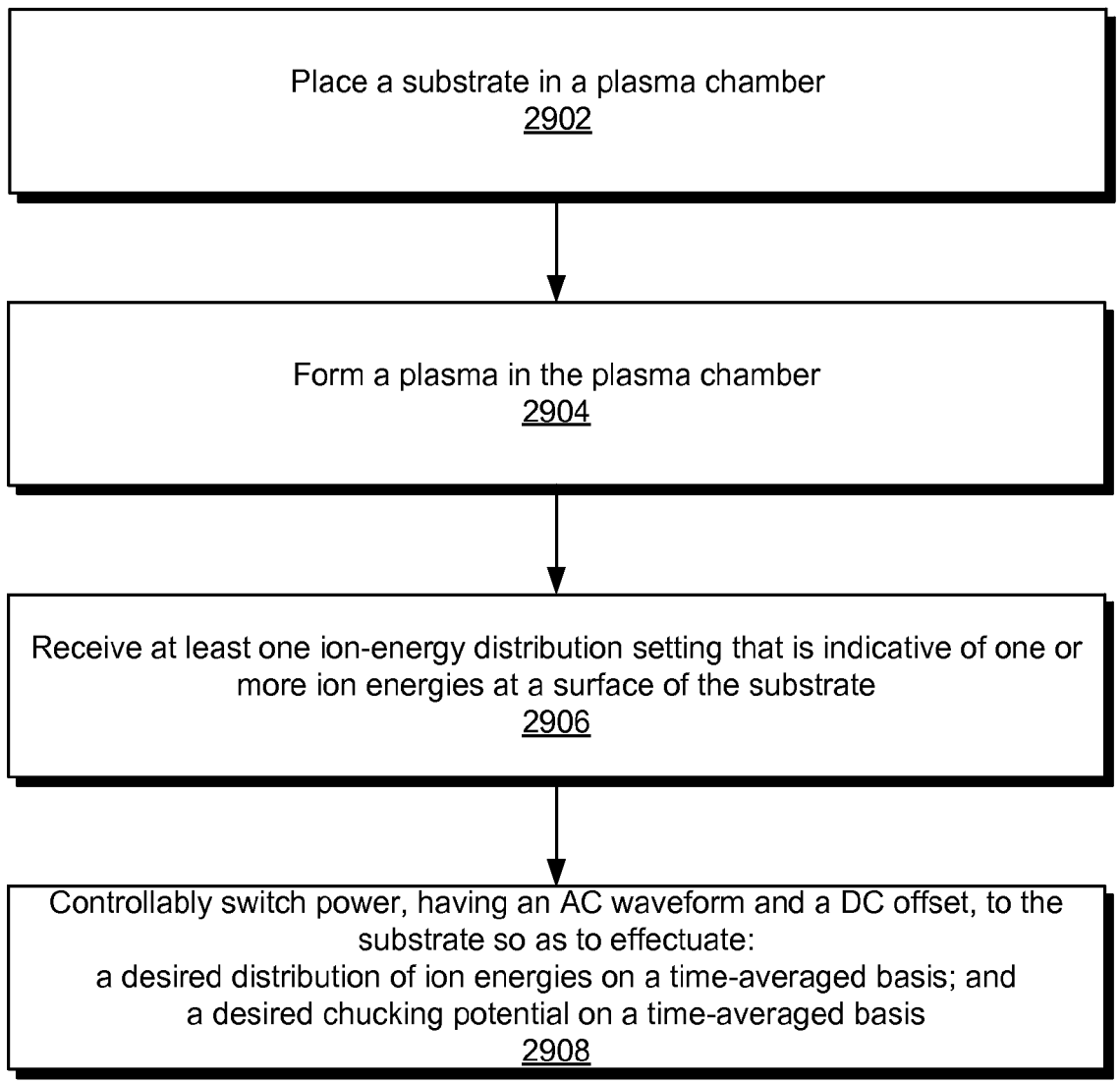
FIG. 29 illustrates another method according to an embodiment of this disclosure.

FIG. 29 illustrates another method 2900 according to an embodiment of this disclosure. The method 2900 includes a place a substrate in a plasma chamber operation 2902. The method 2900 further includes a form a plasma in the plasma chamber operation 2904. Such a plasma can be formed in situ or via a remote projected source. The method 2900 also includes a receive at least one ion-energy distribution setting operation 2906. The setting received in the receive operation 2906 can be indicative of one or more ion energies at a surface of the substrate. The method 2900 further includes a switch power operation 2908 in which power to the substrate is controllably switched so as to effectuate the following: (1) a desired (or defined) distribution of ion energies on a time-averaged basis; and (2) a desired chucking potential on a time-averaged basis. The power can have an AC waveform and a DC offset.

In conclusion, the present invention provides, among other things, a method and apparatus for selectively generating desired (or defined) ion energies using a switch-mode power supply. Those skilled in the art can readily recognize that numerous variations and substitutions may be made in the invention, its use, and its configuration to achieve substantially the same results as achieved by the embodiments described herein. Accordingly, there is no intention to limit the invention to the disclosed exemplary forms. Many variations, modifications, and alternative constructions fall within the scope and spirit of the disclosed invention.

What is claimed is:

1. A system for monitoring a plasma processing chamber, the system comprising:
a power supply configured to provide a periodic voltage function to an output that is configured to couple to the plasma processing chamber, the periodic voltage function having pulses and a portion between the pulses;

an ion current compensation component configured to provide ion current compensation, $I_c$, to the output to modify a slope, $dV_0/dt$, of the portion between the pulses to form a modified periodic voltage function;

a memory to store an effective capacitance value, $C_1$, of at least a substrate support of the plasma processing chamber; and a controller in communication with the power supply, the ion current compensation component, a non-transitory tangible computer readable medium, and the memory, wherein the non-transitory tangible computer readable medium is encoded with instructions, and wherein the controller is configured to execute the instructions, the instructions comprising:

determining the slope, $dV_0/dt$, of the portion between the pulses of the modified periodic voltage function;

adjusting a magnitude of the ion current compensation, $I_C$, until $$\frac{dV_0}{dt} - \frac{I_C}{C_1} = 0; \text{ and}$$

monitoring changes of compensation current, $I_C$, over time to monitor a condition of the processing chamber.

2. A system for monitoring a plasma processing chamber, the system comprising:

a power supply configured to provide a periodic voltage function to an output that is configured to couple to the plasma processing chamber, the periodic voltage function having pulses and a portion between the pulses;

an ion current compensation component configured to provide ion current compensation, $I_C$, to the output to modify a slope of the portion between the pulses to form a modified periodic voltage function, the ion current compensation component including:

a controllable DC current source, controlling for current, that is consistently coupled to the output; and a current controller encoded to maintain a constant rate of change of a voltage of the portion between the pulses by:

determining a slope, $dV_0/dt$, of the portion between the pulses of the modified periodic voltage function;

controlling the controllable DC current source to adjust a magnitude of the ion current compensation, $I_C$, until $$\frac{dV_0}{dt} - \frac{I_C}{C_1} = 0; \text{ and}$$

a controller configured to monitor changes of $I_c$ over time to monitor a condition of the processing chamber.

3. A system for monitoring a plasma processing chamber, the system comprising:

a DC power supply that provides a DC voltage that is fixed at a magnitude responsive to an ion-energy setting, wherein the ion-energy setting is indicative of a monoenergetic distribution of ion energy at the surface of a substrate within the plasma processing chamber;

an output disposed to couple to a substrate support;

two switching components including a first switching component coupled to the DC power supply and a second switching component couple to a ground terminal, the two switching components configured to generate a periodic voltage function at the output by alternately coupling the DC voltage and the ground terminal to the output, the periodic voltage function having pulses and a portion between the pulses; and an ion current compensation component coupled to the output, the ion current compensation component including:

a controllable DC current source, separate from the DC power supply, that is consistently coupled to the output; and a current controller configured to monitor a rate of change of a voltage of the portion between the pulses and maintain an uninterrupted ion current compensation current, $I_C$, which is fixed in magnitude, to maintain a fixed rate of change of the voltage; and a controller configured to monitor changes of $I_c$ over time to monitor a condition of the processing chamber.

4. The system of claim 1, wherein the effective capacitance value, $C_1$, includes capacitances of an electrical path between the output and the substrate support as well as one or more capacitances of the substrate support.

5. The system of claim 4, wherein the effective capacitance value, $C_1$, also accounts for a capacitance of the substrate.

6. The system of claim 5, wherein the effective capacitance value, $C_1$, also accounts for insulation coupled to the substrate support.

7. The system of claim 1, wherein the power supply is configured to be DC-coupled to the plasma processing chamber.

8. The system of claim 1, wherein the controller instructions further include comparing the modified periodic voltage function to a reference waveform, wherein differences between the modified periodic voltage function and the reference waveform are indicative of a fault.

9. The system of claim 1, wherein the controller instructions further include comparing portions of each cycle of the modified periodic voltage function to each other, and if variations between cycles above a threshold are observed, then a fault indication is triggered.

10. The system of claim 1, wherein the controller instructions further include identifying a fourth portion of the modified periodic voltage function, and if this fourth portion has a nonlinear slope, then identifying a nonlinear change in capacitance of the system.

11. The system of claim 2, wherein the controllable DC current source comprises at least a power supply in series with an inductive element.

12. The system of claim 2, wherein the controller instructions further include:

altering an amplitude of voltage of the modified periodic voltage function generated by the power supply; and adjusting the DC current source such that the modified periodic voltage function is altered to a greater extent than if one of the voltage or ion current compensation were altered alone.

13. The system of claim 2, wherein the controller instructions further include comparing the modified periodic voltage function to a reference waveform, wherein differences between the modified periodic voltage function and the reference waveform are indicative of a fault in the system.

14. The system of claim 2, wherein the controller instructions further include comparing portions of each cycle of the modified periodic voltage function to each other, and if variations between cycles above a threshold are observed, then a fault indication is triggered.

15. The system of claim 2, wherein the controller instructions further include identifying a portion of the modified periodic voltage function having a slope $dV_O/dt$, and if this slope is nonlinear, then recognizing that the system is experiencing a nonlinear change in capacitance.

16. The system of claim 3, wherein the controller instructions further include comparing the modified periodic voltage function to a reference waveform, wherein differences between the modified periodic voltage function and the reference waveform are indicative of a fault in the system.

17. The system of claim 3, wherein the controller instructions further include comparing portions of each cycle of the modified periodic voltage function to each other, and if variations between cycles above a threshold are observed, then a fault indication is triggered.

18. The system of claim 3, wherein the controller instructions further include determining slope $dV_O/dt$, and if this slope is nonlinear, then recognizing that the system is experiencing a nonlinear change in capacitance.

19. The system of claim 1, wherein the tangible computer readable medium and the memory are the same.

\* \* \* \* \*